(12) United States Patent
 Gradinaru et al.

(10) Patent No.: US 10,794,802 B2
(45) Date of Patent: Oct. 6, 2020

(54) WHOLE-BODY TISSUE STABILIZATION AND SELECTIVE EXTRACTIONS VIA TISSUE-HYDROGEL HYBRIDS FOR HIGH RESOLUTION INTACT CIRCUIT MAPPING AND PHENOTYPING

(71) Applicant: California Institute of Technology, Pasadena, CA (US)

(72) Inventors: Viviana Gradinaru, La Canada Flintridge, CA (US); Jennifer Treweek, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 247 days.

(21) Appl. No.: 15/239,724

(22) Filed: Aug. 17, 2016

(65) Prior Publication Data

US 2017/0199104 A1    Jul. 13, 2017

Related U.S. Application Data

(63) Continuation-in-part of application No. 14/447,607, filed on Jul. 30, 2014, now Pat. No. 9,778,154.

(60) Provisional application No. 62/205,899, filed on Aug. 17, 2015, provisional application No. 61/992,103, filed on May 12, 2014, provisional application No. 61/880,401, filed on Sep. 20, 2013.

(51) Int. Cl.
| | |
|---|---|
| *A61L 27/24* | (2006.01) |
| *C08L 71/02* | (2006.01) |
| *B82Y 5/00* | (2011.01) |
| *G01N 1/30* | (2006.01) |
| *C12Q 1/6841* | (2018.01) |
| *C12Q 1/68* | (2018.01) |
| *C12Q 1/6806* | (2018.01) |

(52) U.S. Cl.
CPC ............ *G01N 1/30* (2013.01); *C12Q 1/68* (2013.01); *C12Q 1/6841* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 6,007,833 | A | 12/1999 | Chudzik et al. |
| 6,232,092 | B1 | 5/2001 | Rogers |
| 6,465,208 | B1 | 10/2002 | Rogers |
| 6,472,216 | B1 | 10/2002 | Chiang |
| 8,399,207 | B2 | 3/2013 | Liaw et al. |
| 9,778,154 | B2 | 10/2017 | Gradinaru et al. |
| 9,778,155 | B2 | 10/2017 | Gradinaru et al. |
| 2014/0357526 | A1 | 12/2014 | Caprioli et al. |
| 2015/0087001 | A1 | 3/2015 | Gradinaru et al. |
| 2015/0144490 | A1* | 5/2015 | Deisseroth ............... G01N 1/30  204/461 |
| 2016/0123854 | A1 | 5/2016 | Gradinaru et al. |

FOREIGN PATENT DOCUMENTS

| | | |
|---|---|---|
| CN | 103169988 A | 6/2013 |
| EP | 3047271 | 7/2016 |
| JP | 2003-48928 A | 2/2003 |
| JP | 2005-535752 A | 11/2005 |
| KR | 10-2016-0058900 A | 5/2016 |
| WO | 2012/161143 A1 | 11/2012 |
| WO | 2014/025392 A1 | 2/2014 |
| WO | 2015/041755 A1 | 3/2015 |
| WO | 2016/073941 A1 | 5/2016 |
| WO | 2017/031249 A1 | 2/2017 |

OTHER PUBLICATIONS

Chung et al. ("Chung", Nature, May 16, 2013, 497, 332-337).*
D'Andrea ( Biotechnic & Histochemistry, 2009, 79, 55-64).*
Extended European Search Report of EP 14845995.1 dated May 3, 2017, 9 pages.
International Search Report and Written Opinion for PCT/US2014/048985 dated Nov. 25, 2014, 12 pages.
International Preliminary Report on Patentability for PCT/US2014/048985 dated Mar. 22, 2016, 8 pages.
International Search Report and Written Opinion for PCT/US2015/059600 dated May 12, 2016, 8 pages.
International Preliminary Report on Patentability for PCT/US2015/059600 dated May 9, 2017, 5 pages.
International Search Report and Written Opinion for PCT/US2016/047430 dated Nov. 22, 2016, 12 pages.
Albrecht et al., Photo- and Electropatterning of Hydrogel-Encapsulated Living Cell Arrays., Lab on a Chip, 2005, vol. 5(1), pp. 111-118.
Brede et al., Mapping Immune Processes in Intact Tissues at Cellular Resolution, The Journal of Clinical Investigation, 2012, vol. 122(12), pp. 4439-4446.
Chung et al., Structural and Molecular Interrogation of Intact Biological Systems, Nature, 2013, vol. 497, pp. 332-339.
Erturk et al., Three-Dimensional Imaging of the Unsectioned Adult Spinal Cord to Assess Axon Regeneration and Glial Response after Injury, Nature Medicine, 2012, vol. 18(1), pp. 166-171.
Genina et al. Optical Clearing of Cranial Bone. Advances in Optical Technologies (2008); 9 pages.
Greenberg et al., Perilipin, a Major Hormonally Regulated Adipocyte-specific Phosphoprotein Associated with the Peripehery of Lipid Storage Droplets, The Journal of Biological Chemistry, 1991, vol. 266(17), pp. 11341-11346.

(Continued)

*Primary Examiner* — Misook Yu
*Assistant Examiner* — Kauser M Akhoon
(74) *Attorney, Agent, or Firm* — Nixon Peabody LLP

(57) ABSTRACT

In various embodiments, the present application teaches methods for tissue clearing in which tissues are rendered macromolecule-permeable and optically-transparent, thereby exposing their cellular structure with intact connectivity. In some embodiments, the present application teaches ePACT, which is a protocol for enhanced tissue clearing via expansion. In some embodiments, the present application teaches visualizing a tissue that has been expanded via ePACT.

26 Claims, 19 Drawing Sheets

(56) References Cited

OTHER PUBLICATIONS

Hoffman, A.S., Hydrogels for Biomedical Applications, Advanced Drug Delivery Reviews, 2002, vol. 54, pp. 3-12.

Kiviranta et al. The Rate of Calcium Extraction During EDTA Decalcification from Thin Bone Slices as Assessed with Atomic Absorption Spectrophotometry. Histochemistry (1980). 68:119-127.

LEICA HCX PL APO 63X/1.3 GLYC CORR CS (21(degrees)C). Leica technical bulletin for glycerol microscope objectives. (2004) 8 pages.

Lu et al. Modeling of Two-Phase Polymerization of Acrylamide in Aqueous Poly(ethylene Glycol) Solution, AIChE Journal, 2011, vol. 57(9), pp. 2493-2504.

Lund et al. Lipid composition of normal human bone marrow as determined by column chromatography. Journal of Lipid Research (1962). 3(1):95-98.

O'Brien et al. Lipid composition of the normal human brain: gray matter, white matter, and myelin. Journal of Lipid Research (1965). 6:537-544.

Oosthuysen et al., Bioprosthetic Tissue Preservation by Filling with a Poly(acrylamide) Hydrogel, Biomaterials, 2006, vol. 27(9), pp. 2123-2130.

Ott et al., Perfusion-Decellularized Matrix: Using Natures Platform to Engineer a Bioarticial Heart, Nature Medicine, 2008, vol. 14(2), pp. 213-221.

Tainaka et al. Whole-Body Imaging with Single-Cell Resolution by Tissue Decoloization. Cell (2014). 159:911-924.

Tomer et al., Advanced CLARITY for Rapid and High-Resolution Imaging of Intact Tissues., Nat Protoc, 2014, vol. 9 (7), pp. 1682-1697.

Treweek et al. Whole-body tissue stabilization and selective extractions via tissue-hydrogel hybrids for high-resolution intact circuit mapping and phenotyping. Nat Protoc (2015). 10(11)1860-1896.

Wang et al. Long-term outcome of cryopreserved bone-derived osteoblasts for bone regeneration in vivo. Biomaterials (2011). 32:4546-4555.

Washington et al., Frontal Polymerization Synthesis of Temperature-Sensitive Hydrogels., J. Am. Chem., 2001, vol. 123(32), pp. 7933-7934.

Yang et al. Single-Cell Phenotyping within Transparent Intact Tissue Through Whole-Body Clearing. Cell (2014). 158 (4):945-958.

\* cited by examiner

PARS cleared mouse tissues - endogenous fluorescence

PACT cleared human pancreas - immunostaining

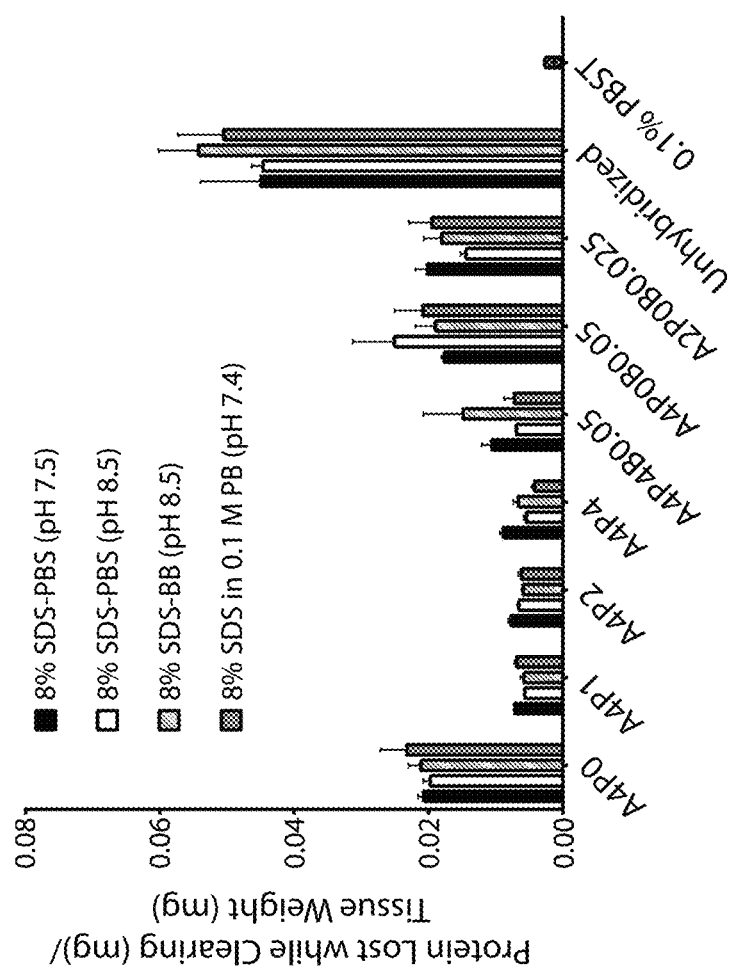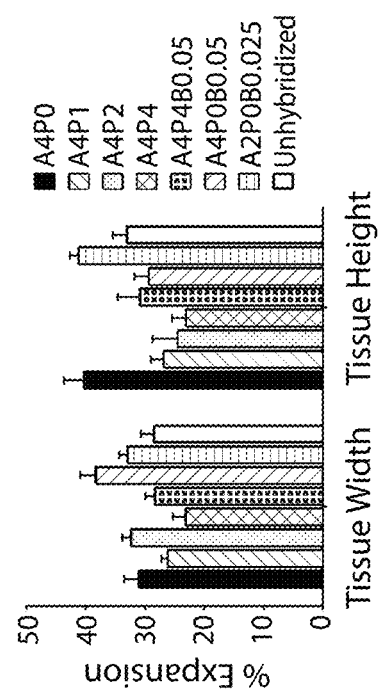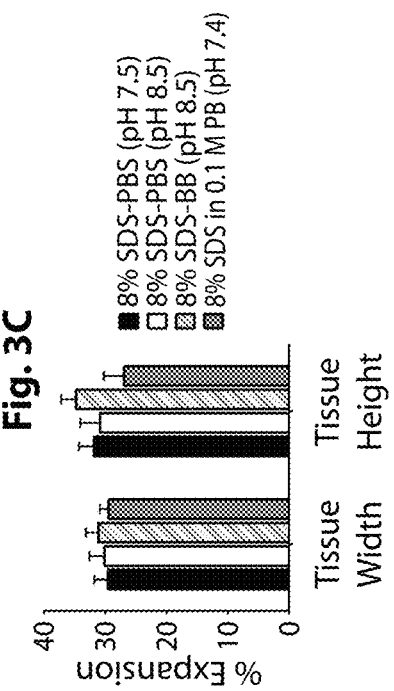

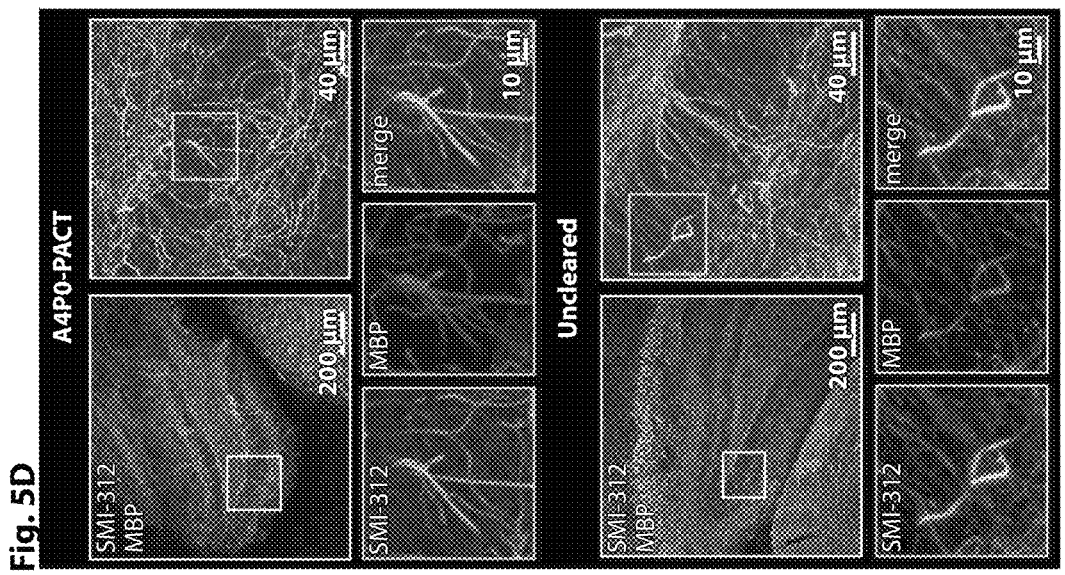
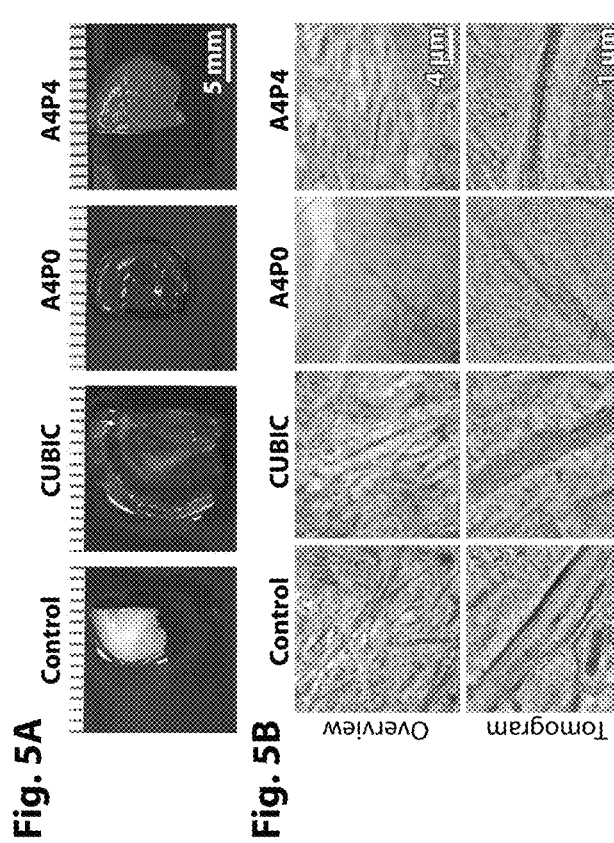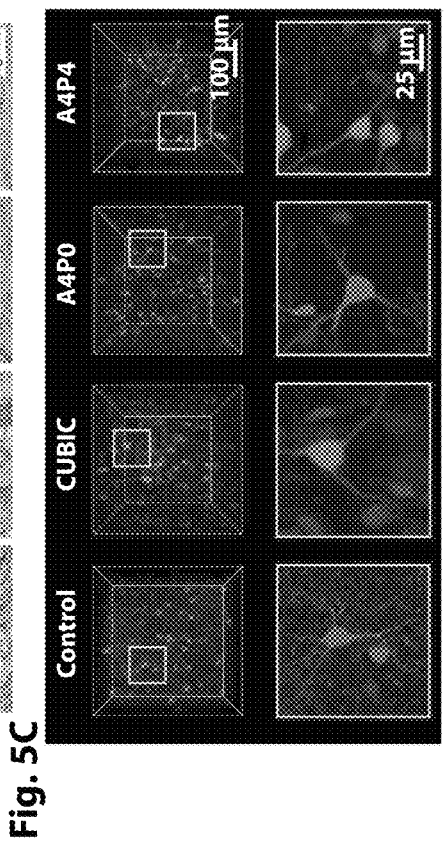

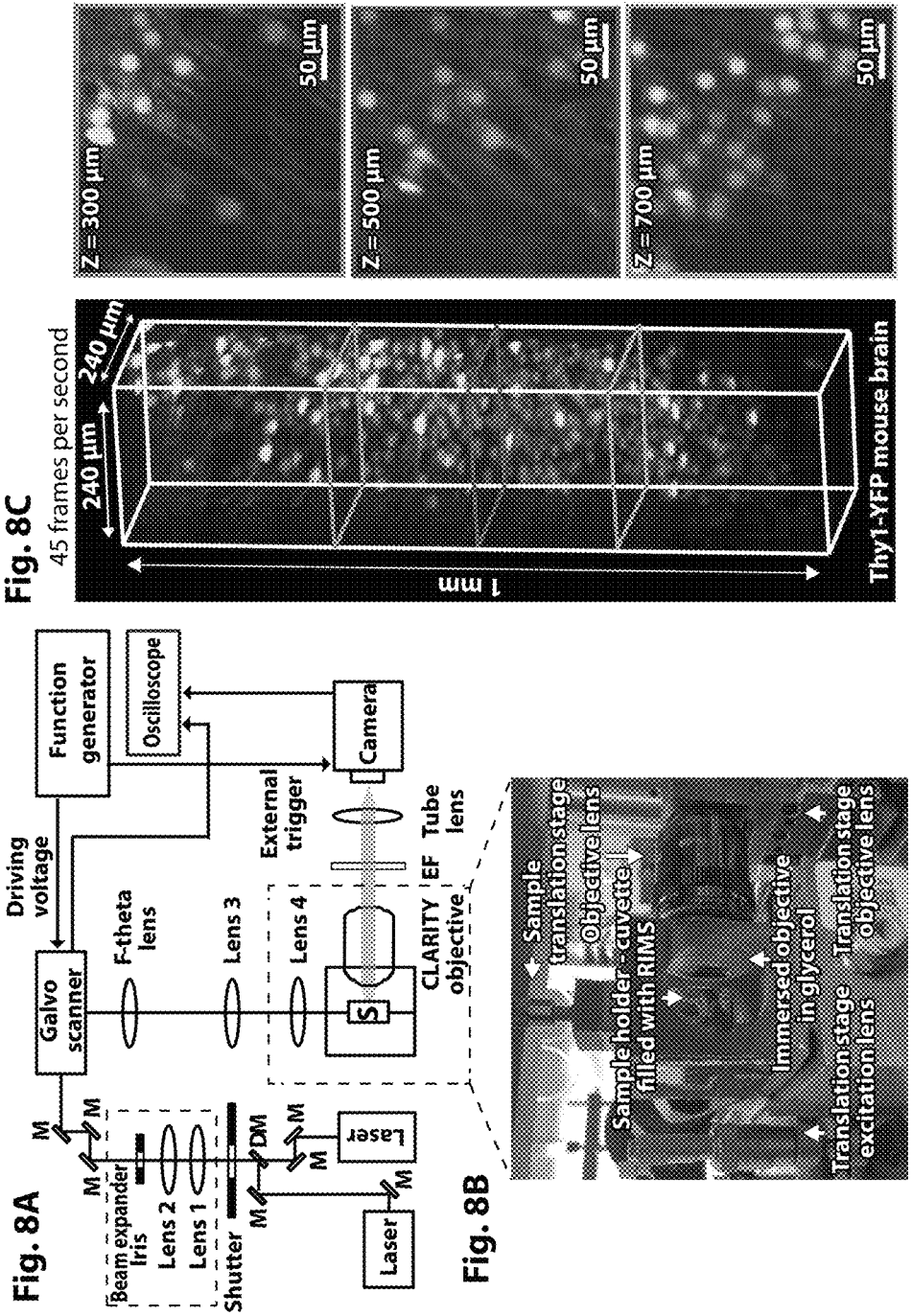

Fig. 10A
PACT clearing progression in 2 mm rat brain slices
Hydrogel polymerization
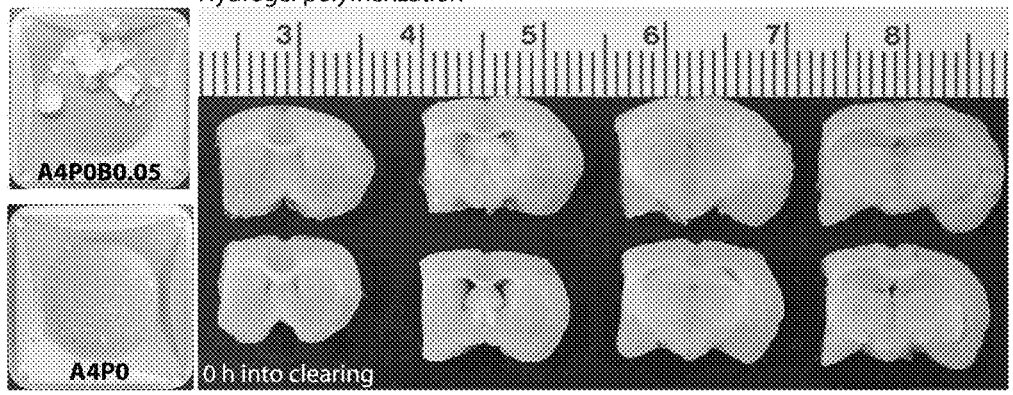
Clearing with 8% SDS in PBS pH 7.5
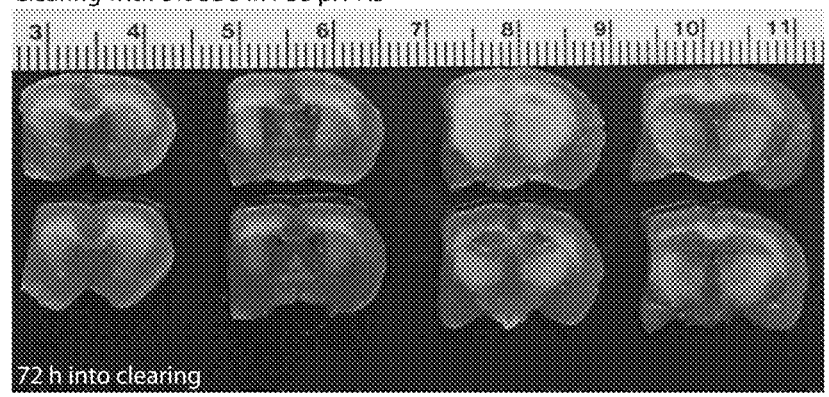
Total average linear expansion: A4P0B0.05 ~ 28%, A4P0 ~ 38%
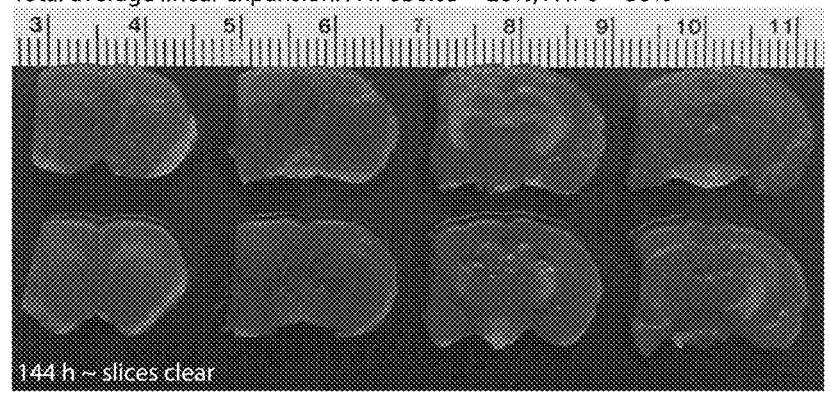

Fig. 10B

RIMS formulation guide to optimize the RIMS RI to that of the cleared sample

| Histodenz (g per 30 mL buffer) | RI | RIMS total volume (mL) | Histodenz (% wt/vol) |
|---|---|---|---|
| 0 | 1.3330 | 30.00 | 0.0 |
| 5 | 1.3575 | 33.00 | 15.0 |
| 10 | 1.3790 | 36.00 | 28.0 |
| 15 | 1.3976 | 38.00 | 39.0 |
| 20 | 1.4134 | 39.50 | 51.0 |
| 25 | 1.4285 | 42.00 | 60.0 |
| 30 | 1.4413 | 45.00 | 67.0 |
| 35 | 1.4536 | 47.00 | 74.0 |
| 40 | 1.4655 | 48.75 | 82.0 |
| 42 | 1.4685 | 50.50 | 83.0 |
| 45 | 1.4741 | 52.00 | 87.0 |
| 47 | 1.4818 | 52.50 | 90.0 |
| 50 | 1.4849 | 53.00 | 94.0 |
| 55 | 1.4917 | 55.00 | 100.0 |

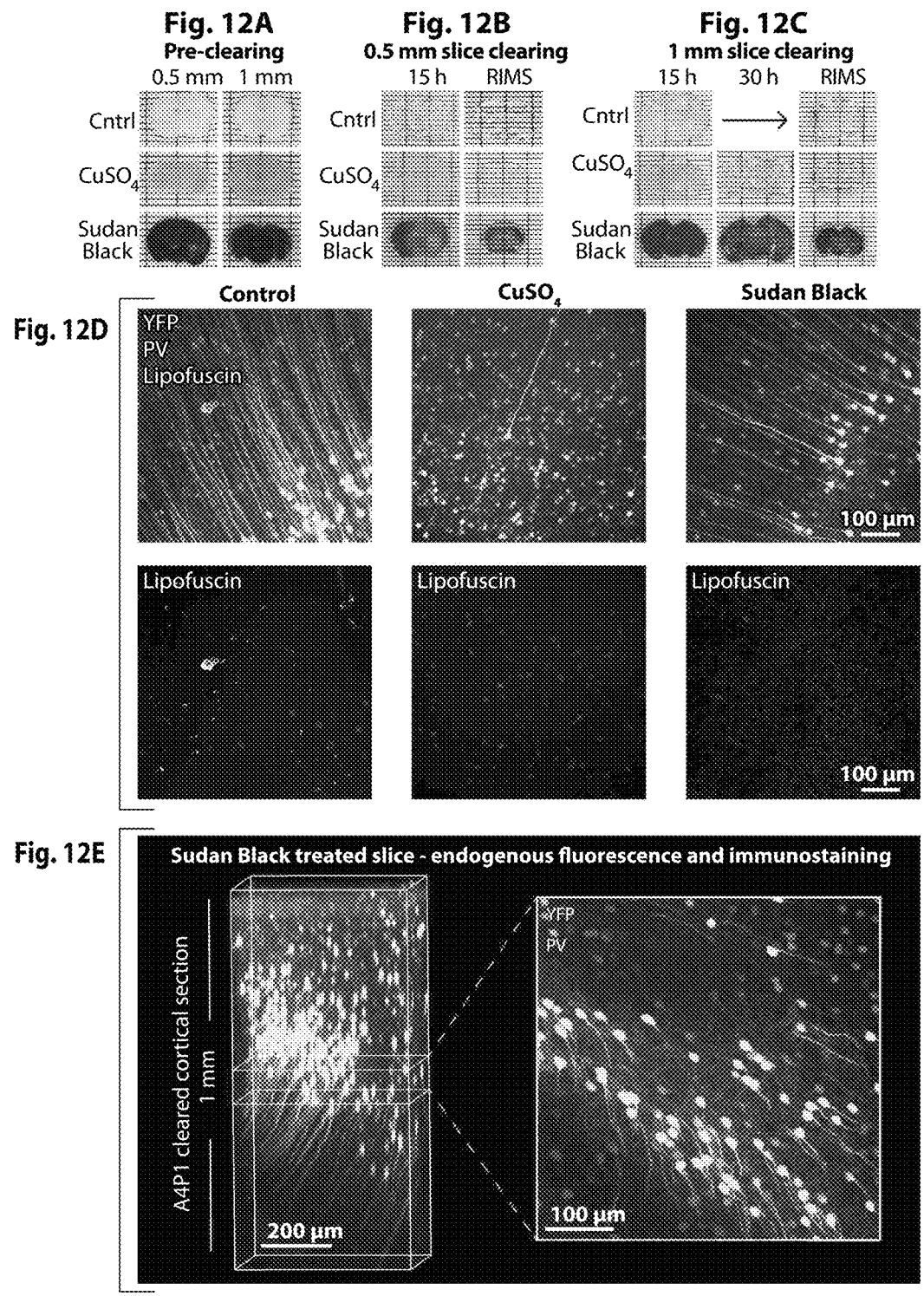

Fig. 13A
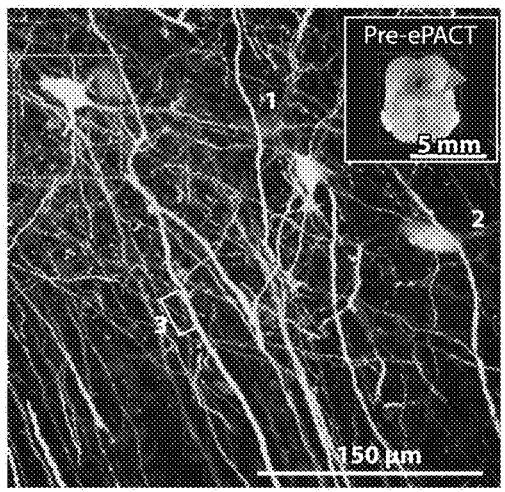
Fig. 13B
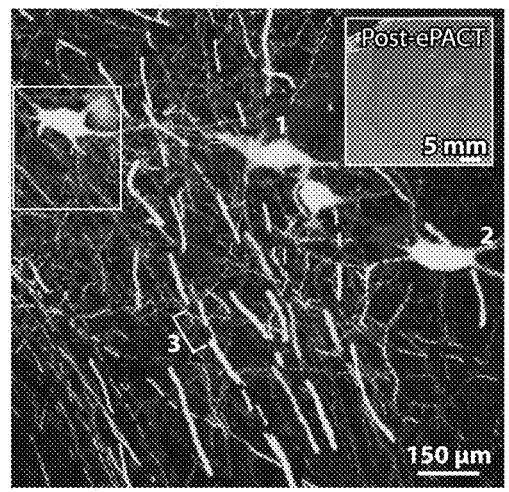
Fig. 13C
Pre-ePACT
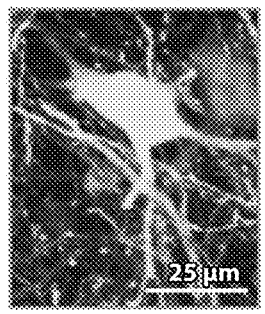
Post-ePACT
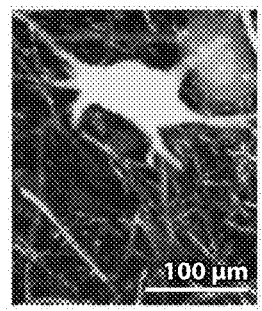
Fig. 13D
ePACT supplies
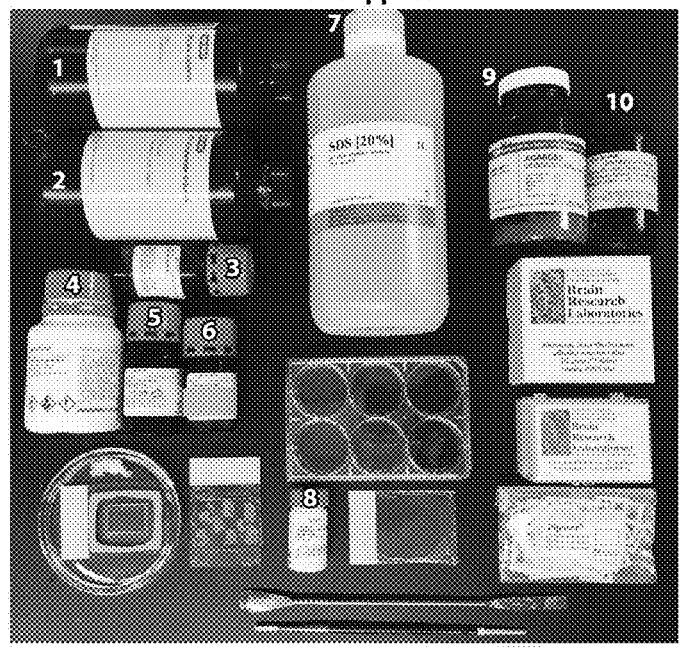

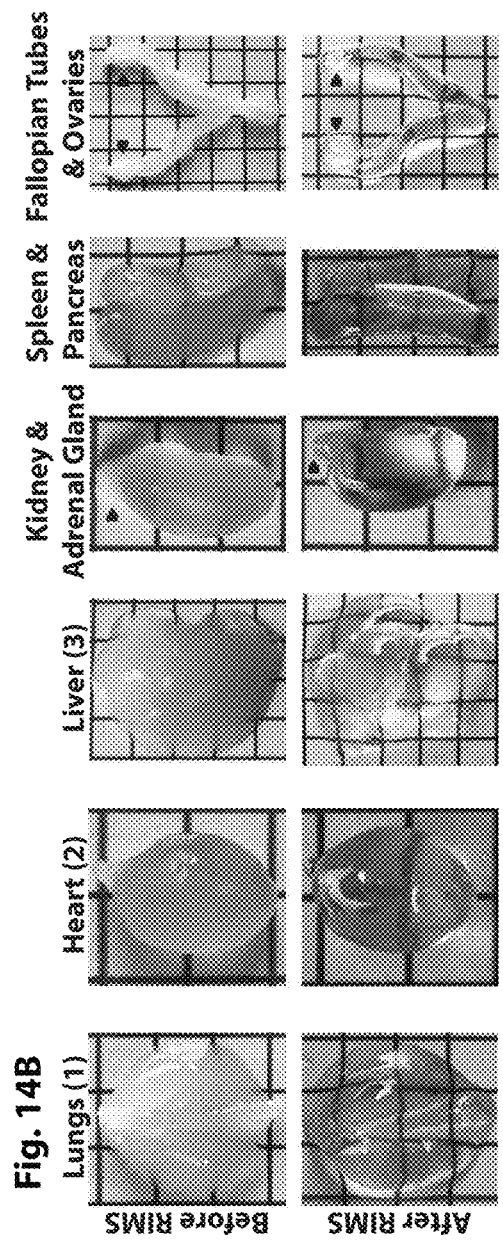
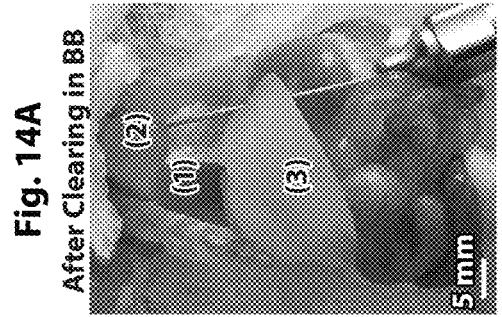
Fig. 14B
Fig. 14A
After Clearing in BB

Fig. 15A

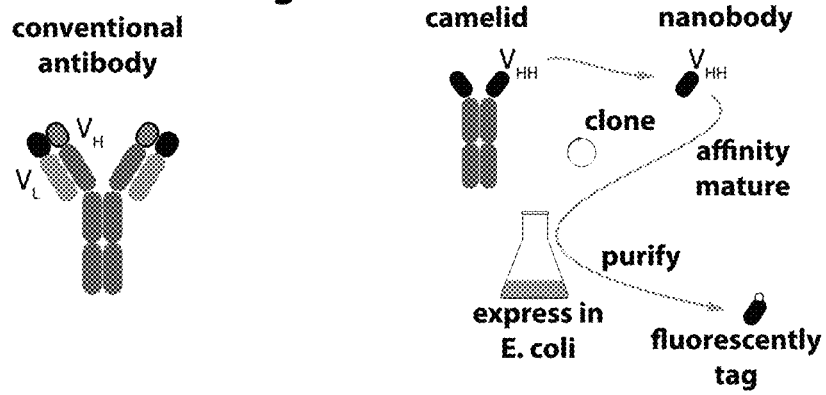

| ANTIBODY | NANOBODY |
|---|---|
| 150 kD, immunogenic | 15 kD, weakly immunogenic |
| Slow tissue penetration | Rapid tissue penetration |
| Nano- to picomolar affinity | Nanomolar, rarely picomolar affinity |
| Risk of aggregation, denaturation | Stable at wide pH, temperature, salt ranges |
| Susceptible to degradation | Resistant to proteases |
| Expensive to obtain | Expensive to develop |
| Expansive, time-tested antibody selection | Limited current selection |

Fig. 15B
GFAP nanobody in 850 μm thick section

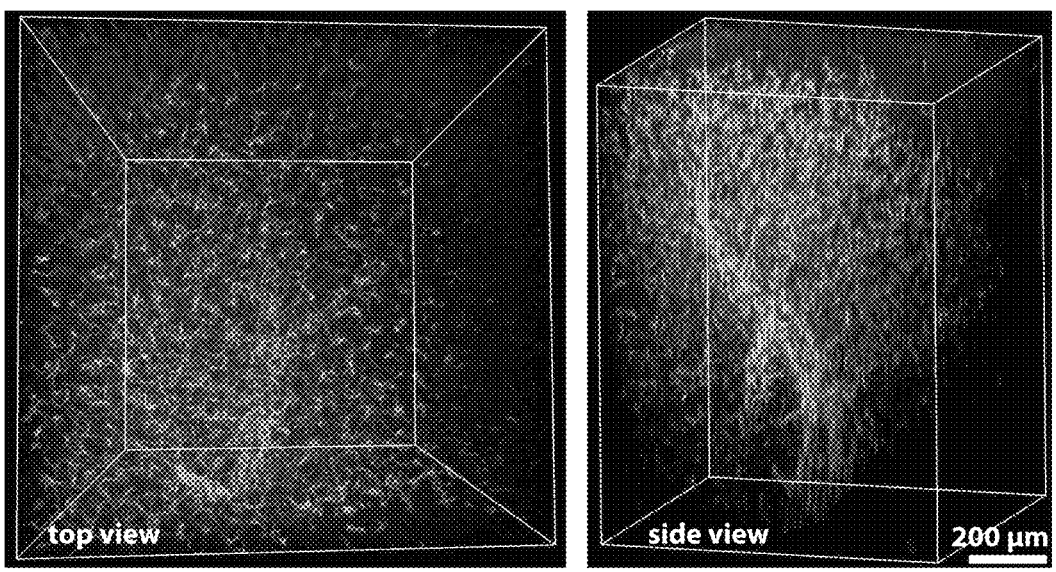

WHOLE-BODY TISSUE STABILIZATION AND SELECTIVE EXTRACTIONS VIA TISSUE-HYDROGEL HYBRIDS FOR HIGH RESOLUTION INTACT CIRCUIT MAPPING AND PHENOTYPING

CROSS-REFERENCE TO RELATED APPLICATION

This application is a continuation-in-part of U.S. patent application Ser. No. 14/447,607 filed on Jul. 30, 2014, currently pending, which claims the benefit of priority to U.S. Provisional Patent Application No. 61/992,103 filed on May 12, 2014, and to U.S. Provisional Patent Application No. 61/880,401 filed on Sep. 20, 2013. This application also claims the benefit of priority under 35 U.S.C. § 119(e) to U.S. Provisional Patent Application No. 62/205,899 filed on Aug. 17, 2015. The contents of all of the aforementioned applications are hereby incorporated herein by reference in their entirety.

GOVERNMENT RIGHTS

This invention was made with government support under Grant Nos. OD017782-01 and AG047664-01 awarded by the National Institutes of Health. The government has certain rights in the invention.

FIELD OF THE INVENTION

The present invention generally relates to the field of tissue preparation and characterization.

BACKGROUND

The following description includes information that may be useful in understanding the present invention. It is not an admission that any of the information provided herein is prior art or relevant to the presently claimed invention.

Owing to their intrinsic transparency, the worm *Caenorhabditis elegans* and the zebrafish *Danio rerio* provide scientists with an unobstructed, organism-wide view of tissue anatomy and cellular activity (e.g. via cell-type specific fluorescent labeling and genetically encoded calcium indicators) using conventional imaging techniques. In combination with their small size and genetic tractability, their whole-body transparency enables rigorous, high throughput investigations into how environmental, cellular, and genetic alterations influence biological processes from cellular signaling and apoptosis, to organism development and survival. By contrast, the comparatively large size and optical opacity of mammalian models generally has limited researchers to imaging snapshots of cellular organization on thin-sectioned tissue samples. However, it was hypothesized that if the bodies of these mammalian model organisms were to acquire the same level of optical transparency as zebrafish embryos, whole-body image datasets would theoretically become available to scientists for study. Certain advancements have been made in the art of rendering various tissues transparent. Nevertheless, additional improvements are needed.

SUMMARY OF THE INVENTION

In various embodiments, the invention teaches a method for clearing and expanding tissue. In some embodiments, the method includes the steps of: (1) applying a fixing solution to the tissue, thereby forming fixed-tissue; (2) applying a surfactant to the fixed-tissue, thereby forming permeabilized-tissue; (3) incubating the permeabilized-tissue in a solution that includes acrylate-acrylamide copolymer (AcAm) and one or more polymerizing agent; (4) incubating the tissue in a solution that includes sodium dodecyl sulfate (SDS), thereby forming SDS-treated cleared tissue; (5) incubating the SDS-treated cleared tissue in a solution that includes collagenase, thereby forming collagenase-treated tissue; and (6) incubating the collagenase-treated tissue in water, thereby forming cleared and expanded tissue. In some embodiments, the fixing solution is comprised of 1-15% paraformaldehyde (PFA) and/or 0.1-5% glutaraldehyde. In some embodiments, the method further includes applying a quenching solution to the fixed tissue. In certain embodiments, the quenching solution includes glycine. In some embodiments, the surfactant includes Triton X-100. In some embodiments, the solution that includes surfactant further includes phosphate buffered saline (PBS). In some embodiments, the solution that includes AcAm includes 0-4% acrylamide, 4-10% sodium acrylate, and 0-1% bis-acrylamide. In certain embodiments, the solution that includes SDS includes SDS at a concentration of 4-10%. In some embodiments, the pH of the solution that includes SDS is 6.5-9.5. In some embodiments, the solution that includes collagenase includes collagenase at a concentration of 1-mg/ml. In certain embodiments, the tissue includes animal tissue. In certain embodiments, the tissue includes mammalian tissue. In certain embodiments, the tissue includes brain tissue. In certain embodiments, the tissue is immunolabeled and/or fluorescently labeled. In some embodiments, the method further includes incubating the tissue in a refractive index matching solution (RIMS).

In various embodiments, the invention teaches a method for visualizing and/or imaging a cleared and expanded tissue. In some embodiments, the invention includes utilizing a microscope to visualize and/or image a tissue treated according to any of the methods described above. In certain embodiments, the tissue includes fluorescently labeled cells. In certain embodiments, the refractive index of the tissue has been homogenized. In some embodiments, the method further includes counting the fluorescently labeled cells. In certain embodiments, the fluorescently labeled cells are automatically counted. In certain embodiments, one or more nucleic acids within the tissue are labeled with a marker that can be visualized and/or imaged with a microscope. In certain embodiments, one or more of the nucleic acids are mRNA. In certain embodiments, the one or more nucleic acids are labeled using single-molecule fluorescence in-situ hybridization (smFISH). In some embodiments, the method further includes quantifying one or more species of mRNA in the tissue based on a unique fluorescent signature.

BRIEF DESCRIPTION OF THE DRAWINGS

Exemplary embodiments are illustrated in the referenced figures. It is intended that the embodiments and figures disclosed herein are to be considered illustrative rather than restrictive.

(FIG. 1A, FIG. 1B, FIG. 1C, FIG. 1D, FIG. 1E) PARS-based whole-body clearing for assessing cellular level AAV tropism (see Supplementary Methods). Three weeks after systemic injection of AAV9: CAG-GFP, mice were PARS-cleared and their organs excised and sectioned for imaging. (FIG. 1A, FIG. 1B), Projection images show GFP+ transduced cells in the adrenal gland. Arrow highlights a GFP+ cell near the surface of the adrenal gland with neuronal morphology, which is shown in higher magnification in FIG. 1B. (FIG. 1C) Projection images show GFP+ cells in the stomach from the surface to the lumen. GFP expression is particularly high in the myenteric plexus. (FIG. 1D, FIG. 1E), AAV9 transduces cells in several layers within the intestine (duodenum). (FIG. 1D) Projection image of GFP fluorescence. Double colored lines correspond to the positions of 50 μm maximum projection images extracted from the data set and presented in FIG. 1E. (FIG. 1E) GFP+ cells in the intestinal crypt (top), submucosal plexus (middle), and myenteric plexus (bottom). (FIG. 1F, FIG. 1G) Islet distribution within human pancreatic tissue. (FIG. 1F) A 2 mm thick section of an adult human pancreas (top) was rendered transparent (bottom) with the PACT method. Briefly, a 2 mm thick section was cut from a 4% PFA-fixed human pancreas, incubated in 0.5% PFA, 4% acrylamide at 4° C. overnight, and then polymerized in fresh A4P0 hydrogel monomer with 0.25% VA-044 thermal initiator for 2 hours at 37° C. The tissue was cleared with 4% SDS-PBS (pH 7.5) for 48 hours, immunostained, and mounted in sRIMS (~50% sorbitol in 0.02 M PB, refractive index of 1.44). (FIG. 1G) The islet distribution was visualized by immunostaining for insulin (red), somatostatin (green) and DAPI (cyan) (see Table 4 for details on antibodies and nuclear stain); panels represent an imaging stack of 70 um. Sparsely distributed islets are easily located with only 5× magnification (middle panel). A group of islets were identified at 10× magnification (right, top) and a 3D image of a single islet was captured with at 25× magnification (right, bottom). All images were collected on a Zeiss LSM 780 confocal with the Fluar 5×0.25 N.A. M27 air objective (w.d. 12.5 mm), Plan-Apochromat 10×0.45 N.A. M27 air objective (w.d 2.0 mm), and the LD LCI Plan-Apochromat 25×0.8 N.A. Imm Corr DIC M27 multi-immersion objective (w.d 0.57 mm).

(FIG. 2A) Supplies for PACT chamber (left): 50 ml conical tube (large sample) or vacutainer (small sample), size 7 stoppers that fit the 50 ml conical tube, PTFE tubing, needles, syringes, and a razor blade or scissors to cut syringe in half. Construct a degassing line that will allow a sample tube to be evacuated of oxygen using the house vacuum and then placed under inert nitrogen atmosphere (FIG. 2A, left to right). (FIG. 2B) The PACT procedure for sample degassing and hydrogel polymerization is as follows (FIG. 2B, top row): prepare the hydrogel monomer solution, taking care to keep all reagents ice-cold; infuse the tissue sample with hydrogel monomer solution at 4° C.; insert the vacuum line needle into the stopper and place the container under house vacuum for 5-10 minutes; remove the vacuum line and insert both a venting needle and the hypodermic needle, which is connected to the nitrogen gas line tubing; bubble nitrogen gas through the sample and solution for 5-10 minutes, ensuring that the venting needle allows excess pressure to escape from the PACT container; quickly remove both needles and place the sample and container in a 37° C. water bath for 1-3 hours. (FIG. 2B, bottom row) Once the hydrogel has polymerized, pour off excess hydrogel, rinse the sample with 1×PBS and/or tissue off with a Kimwipe, section the sample (optional), and place the sample into a 50 ml conical filled with 8% SDS clearing buffer. Incubate at 37° C. in a shaking water bath until the sample is clear. Thoroughly wash the cleared sample, immunostain (optional), and then incubate the sample in RIMS to improve its optical clarity.

FIGS. 3A-3C depict, in accordance with various embodiments of the invention, PACT protein loss and tissue expansion for different hydrogel and clearing conditions. A detailed comparison of the protein loss and tissue expansion for eight different hydrogel matrix compositions: A4P0, A4P1, A4P2, A4P4, A4P0B0.05, A4P4B0.05, A2P0B0.025, and unhybridized, and four different clearing buffers: 8% SDS-PBS (pH 7.5), 8% SDS-PBS (pH 8.5), 8% SDS-BB (pH 8.5), and 8% SDS in 0.1 M PB (pH 7.4). Perfused and fixed mouse brains were sliced into 1 mm thick coronal slices and combinations of all the different hydrogel and clearing conditions were performed on slices from comparable locations. Slices were monitored and imaged every 12 hours, and the clearing buffer was collected for protein loss measurements and replaced. (FIG. 3A) Total protein content within each sample of clearing buffer collected throughout the clearing process was measured by the bicinchoninic acid assay (BCA) by extrapolating the concentration of protein from a standard curve of BSA concentration in each clearing buffer (FIG. 11A). Protein amounts from each time point were summed until each slice was completely clear, resulting in a measure for the total amount of protein lost while clearing for each slice. This total protein loss was then compared to the initial weight of each slice (n=3). A comparison was also made with the protein loss of 100 μm thick slices that were not cleared, but were permeabilized with PBST overnight (n=9). (FIG. 3B) Comparison between total width and height tissue expansion between hydrogel compositions (n=4). (FIG. 3C) Tissue expansion comparisons with different clearing conditions (n=8). Data are presented as mean±s.e.m. Experiments on vertebrates conformed to all relevant governmental and institutional regulations, and were approved by the Institutional Animal Care and Use Committee (IACUC) and by the Office of Laboratory Animal Resources at the California Institute of Technology.

(FIG. 4A) Representative images of two 1-mm thick coronal brain slices (~1.0-0.0 mm anterior to bregma) through the time course for PACT clearing and a comparison of time to clear (mean±s.e.m.) for each PACT hydrogel composition. For the representative images, slices were cleared with 8% SDS-PBS (pH 8.5) and incubated in RIMS for 24 hours. (FIG. 4B) Imaging of antibody penetration through different PACT tissue preparations. Previously cleared and washed 1 mm thick slices were immunostained for parvalbumin (red) and nuclei stained with DAPI (cyan), using 2-day incubations with the primary and Fab format secondary antibodies (for immunostaining reagents, see Table 4), transferred to RIMS for 5 hours, and then RIMS-mounted. Samples from the cortex, traversing the depth of the slice, were imaged on a Zeiss LSM 780 confocal microscope with a Plan-Apochromat 10×0.45 N.A. M27 air objective (w.d 2.0 mm). To ensure even illumination throughout the depth of the slice for fair antibody detection we applied laser power z-correction (Zen software, Zeiss): power was changed linearly for each slice, shown as a gradient next to each image; starting power values at the top were chosen to match the level of fluorescence at the surface across slices while the range of powers varied for different PACT conditions. Shown are images of staining through A4P0, A4P1, and A4P4 hydrogel embedded samples, as well as unhybridized tissue, cleared with 8% SDS-PBS (pH 7.5). Since antibody and small molecule dye diffused through both the top and bottom surfaces of the slice simultaneously, the images show that within 2 days DAPI has fully penetrated in all of the conditions, while antibody labelling has progressed to varying extents, depending on the PACT condition. As slices cleared with the different conditions also swell to different extents during the process (indicated by their difference in height relative to the pre-clearing height of 1 mm, as indicated by the white dotted lines in (FIG. 4B)), penetration of antibody through a more swollen sample will either require longer diffusion time or faster diffusion rate to reach an equivalent anatomical depth as in a less swollen sample. Incomplete detection of the DAPI signal in A4P1 and A4P4 slices is due to the difficulty to achieve similar light penetration in highly cross-linked slices. (FIG. 4C) Depiction of parvalbumin staining through same slices as in (FIG. 4B). DAPI signal has been removed to better show the variable penetration of the antibody over the course of a 2 day period. (FIG. 4D) Quantification of antibody penetration through PACT conditions depicted in (FIG. 4B, FIG. 4C). Antibody fluorescence signal was scaled by the average DAPI intensity for each z-section inside the volume and the average scaled fluorescence along a line perpendicular to the tissue surface produced a final estimate of labelling intensity as a function of tissue depth (see Supplementary Methods). Antibody diffusion was fit to an exponential model, $[f(x)=a*\exp(-tau*x)+b]$ with the exponent tau being inversely proportional to the square-root of the diffusivity, wherein a larger tau indicates slower diffusion. Labeling intensities for A4P0, A4P1, A4P4 and unhybridized samples cleared with 8% SDS-PBS (pH 7.5), as a representative sample of all the different buffers, are plotted on a logarithmic scale. The amount of PFA contained in the hydrogel-tissue matrix is inversely proportional to immunohistochemical staining efficiency.

FIGS. 5A-5D depict, in accordance with various embodiments of the invention, preservation of tissue architecture during delipidation. The differential effects of individual clearing conditions on cellular architecture and endogenous and stained fluorescence imaging. (FIG. 5A, FIG. 5B, FIG. 5C) Mice that received bilateral intracranial injections in the lateral septum of AAV expressing the tdTomato transgene were perfusion-fixed with 4% PFA and a subset of 1 mm thick unhybridized coronal brain sections were prepared for microscopy without clearing (control, first column), or were first rendered transparent via the CUBIC method (second column). The second subset of 1 mm thick sections underwent PACT processing: A4P0- (third column) or A4P4-embedding (fourth column) and clearing with 8% SDS-PBS (pH 7.5), followed by preparation for ultrastructural study or RIMS mounting. (FIG. 5A) Brain sections were photographed after fixation (control) or immediately after clearing (CUBIC, A4P0, A4P4) to illustrate the degree of tissue swelling that occurred for each condition. (FIG. 5B) Control (unhybridized, uncleared), CUBIC, and PACT-cleared (A4P0, A4P4) tissues were then processed identically for ultrastructural examination using electron microscopy and tomography (see Supplementary Methods). Overviews (top row) from each of the four samples illustrate the relative amount of lipid loss attributable to the different clearing methods, in terms of contrast between structures. Tomographic reconstruction (bottom row) of sub-regions of the overviews, each showing a portion of an axon and surrounding cellular structures, indicates the extent of change at the fine-structural level. (FIG. 5C) Control, PACT- and CUBIC-cleared brain sections were mounted in RIMS or CUBIC reagent-2, respectively, and the endogenous expression of tdTomato was imaged on a Zeiss LSM 780 confocal with the LD LCI Plan-Apochromat 25×0.8 N.A. Imm Corr DIC M27 multi-immersion objective (w.d 0.57 mm). Volume renderings (top: x,y,z=300 µm for PACT- and CUBIC-cleared samples and x,y,z=300,300,140 µm for control) and maximum intensity projections (bottom: x,y,z=100,100,50 µm) are shown. In all images except the uncleared control, cells are visualized throughout the volume imaged. In the control image, light is unable to penetrate through the sample to image at depth. (FIG. 5D) Preservation of myelin proteins. 200 µm thick A4P0-PACT cleared mouse brain sections and 50 µm thick uncleared sections were immunostained for SMI-312 and for myelin basic protein (MBP), using Atto 488-conjugated and Atto 647N-conjugated Fab format secondaries (see Table 4 for details). After a 2-hour RIMS incubation, the transparent sections were mounted and imaged on a Zeiss LSM 780 confocal with the Plan-Apochromat 10×0.45 N.A. M27 air objective (w.d 2.0 mm) and the LD LCI Plan-Apochromat 25×0.8 N.A. Imm Corr DIC M27 multi-immersion objective (w.d 0.57 mm). The images correspond to a 50 µm thick maximum intensity projection over the dentate gyms; Top: A4P0-PACT cleared, Bottom: uncleared smaller panels are high magnification images of the boxed areas showing myelinated axons. Experiments on vertebrates conformed to all relevant governmental and institutional regulations, and were approved by the Institutional Animal Care and Use Committee (IACUC) and by the Office of Laboratory Animal Resources at the California Institute of Technology.

(FIG. 6A) A completed PARS chamber used for whole-body tissue clearing. (FIG. 6B) Individual parts to build a PARS chamber: (1) three ⅛"×⅛" barbed connectors, (2) two 3/32" barbed male Luers with locking nut, (3) a 1000 µl pipette tip box, (4) a 1-gallon Ziploc freezer bag, (5) a 3-way stopcock with Luer lock, (6) a 3/32" barbed female Luer with full tread, (7) a roll of lab tape, (8) a 22 G×1" gavage needle, (9) a ⅛" barbed male slip Luer, (10) a female Luer tee with locks, (11) clay, and (12) Tygon E-lab tubing. Ruler shown is 5 cm in length. (FIG. 6C) Three ⅛" holes are drilled into the pipette tip box: two into the box front and one into its side, all approximately 2 cm below the top rim of the box. The three ⅛"×⅛" barbed connectors are placed into the drilled holes. To connect the outflow line (blue tape bands on outflow line tubing), a piece of Tygon tubing is connected from the bottom inside of the pipette box to the single ⅛" barbed connector that was inserted through the box side. To continue the outflow line, a second, longer piece of blue-taped tubing is attached to the outer fitting of this same barbed connector (on the outside of the pipette tip box side) and then the other end of this tubing is threaded through the peristaltic pump, pulled back over toward the pipette box, and finally (FIG. 6D) connected to a 3-way stopcock with a 3/32" barbed male Luer with locking nut (rightmost blue-banded tubing in FIG. 6D). To form the inflow line, a short length of tubing (green tape band) is used to connect the 3-way stopcock to the front right ⅛" barbed connector of the pipette box. The solute flushing line and nitrogen bubbling line, which are subserved by the same tubing (white tape band), are formed by another short length of tubing that joins the third port of the stopcock to the front left ⅛" barbed connector. (FIG. 6E) The inflow line is continued inside the pipette box, with the tubing coiled several times around the base of the box so that the solute will be re-heated before it passes through the feeding gavage into the subject. The solute flushing line and nitrogen bubbling line is continued inside the pipette tip box and taped to the bottom of the chamber (not shown). (FIG. 6F) The tip of the coiled inflow line tubing is threaded up through the tip wafer (see birdseye view of threaded wafer in (FIG. 6A)) and connected to a 22 G×1" gavage needle with a ⅛" barbed male slip Luer. The gavage needle is held into position with a short loop of Tygon tubing (~90 mm) threaded through 2 holes of the wafer. (FIG. 6G) During the polymerization step, the chamber is placed into a 37° C. water bath and sealed in a Ziploc bag. The tubing is attached to the chamber with three ⅛"×⅛" barbed connectors punctured through the Ziploc bag. The Tygon tubing is reconnected from the outside of the bag and surrounded with clay to make an air-tight seal. (FIG. 6H) The animal is placed onto the pipette tip box and the 22 G×1" gavage needle is used to catheterize the heart. (FIG. 6I) The chamber is placed into a 37° C. waterbath. A female Luer tee, which is taped onto the lid of the pipette tip box, is punctured through the Ziploc bag and this joint is sealed with clay to ensure an air-tight seal. Finally, to accelerate polymerization, a vacuum line is connected to the female Luer tee to remove oxygen (orange arrow) and a nitrogen gas line (white arrow) is connected to the ⅛" barbed connector to deliver a steady flow of nitrogen into the bagged system. The solute is continually circulated through the animal from the outflow line (blue arrow, which also indicates the direction of flow through blue-taped tubing) and inflow line (green arrow, which also indicates the direction of flow through green-taped tubing).

(FIG. 7A) A4P0-hybridized organs shown before the start of clearing (left) and after 5 days of clearing with 8% SDS-PBS (pH 8.5) and overnight washing with 1×PBS at pH 7.5 (right). Numbers correspond to the extracted organs in panel (FIG. 7B). (FIG. 7B) Extracted organs from the cleared mouse of panel (FIG. 7A), pictured before (top) and after (bottom) RIMS incubation for 3 days. Black pointers correspond to the adrenal gland on the kidney and to the ovaries on the fallopian tubes. Each square represents 0.5 cm$^2$.

FIGS. 8A-8C depict, in accordance with various embodiments of the invention, light sheet microscopy enables fast and high-resolution imaging of cleared samples. (FIG. 8A) A schematic diagram of the light sheet microscope; M, mirror; DM, dichroic mirror; S, sample; EF, emission filter. The scientific CMOS camera (Zyla 4.2 sCMOS, Andor) is running in a light sheet mode, in which the readout direction of the camera is unidirectional and synchronized with the scanning direction and speed of the light-source. In this configuration, only the pixels that are illuminated will be recorded thus improving the signal to noise ratio of the image. For ease of synchronization, the function generator, the camera, and the oscilloscope are controlled using a custom MATLAB program. (FIG. 8B) An image of the 3D-printed sample holder, where the CLARITY objective (Olympus 25×1.0 N.A. multi-immersion objective (w.d. 8.0 mm)) is immersed in glycerol, while the sample is within a quartz cuvette filled with RIMS. (FIG. 8C) A volume rendering (Imaris, Bitplane) and cross sections at different depths of a cleared Thy1-YFP mouse brain section (1 mm thick), taken with the light sheet microscope, the intensity of the layers was normalized. The images were acquired at 45 frames per second (voxel size: 0.117 µm×0.117 µm×0.25 µm, bit depth: 12). The cross sections at different depths, which are perpendicular to the scan direction, are maximum intensity projections (Imaris) across a 5 µm volume. A parts list for this set-up is available in Table 7.

(FIG. 9A) Tracing using neuTube. (FIG. 9B) Tracing using Imaris 7.1 (Bitplane). Results shown here took 25 minutes for a novice user with ~5 hours of total experience using each tracing tool. Total tracing time to achieve similar results was generally comparable but we found neuTube to be more efficient for quickly tracing isolated neurites. In FIG. 9A top panel, neuTube 3D visualization, FIG. 9A bottom left panel, neuTube semi-automated tracing result, FIG. 9A middle right panel, Tracing error, FIG. 9A bottom right panel, Manual correction. In FIG. 9B, top panel, Imaris ROI selection, FIG. 9B bottom left panel, Imaris Autopath seeding, FIG. 9B middle right panel, Manual correction of tracing error, FIG. 9B bottom right panel, Trace extension using Autopath.

FIGS. 10A-10B depict, in accordance with various embodiments of the invention, effects of bis-acrylamide crosslinker on clearing time and swelling of PACT-cleared sections. (FIG. 10A) Representative images of the time-course for PACT clearing of four 2 mm thick rat coronal brain slices, (displayed anterior to posterior, from left to right). Slices were embedded in either A4P0B0.05 or A4P0 and then cleared with 8% SDS-PBS (pH 7.5). The A4P0 slices were completely clear by 144 hours. Although some heavily myelinated brain sections seemed to resist clearing in A4P0B0.05-embedded sections initially, this effect did not persist, resulting in similar overall clearing time as slices embedded without bis-acrylamide. Likewise, tissue transparency was indistinguishable between conditions after their 48-hour incubation in RIMS. Unlike in 1 mm sections (FIG. 3), bis-acrylamide did limit tissue expansion in 2 mm thick slices (A4P0: 38% total average linear expansion, A4P0B0.05: 28% average linear expansion). (FIG. 10B) RIMS formulation guide to optimize the RI to that of the cleared sample. RIMS formulated with 82% Histodenz™ (RI=1.4655) should be broadly applicable to cleared brain tissue, while RIMS with a higher RI of 1.48-1.49 is suggested for denser cleared tissue such as bone.

(FIG. 11A) A representative case, shown here for BSA concentrations in 8% SDS-PBS (pH 7.5). (FIG. 11B) Graphs show single-trial, representative protein loss measurements for each hydrogel condition in each clearing buffer. Protein content was measured at 12 hours into clearing, at 24 hours, and then every 24 hours until the samples were clear, and normalized to the initial weight of the slice. Experiments were performed in triplicates, representative single trials for each combination are shown. (FIG.

Figure 1A:
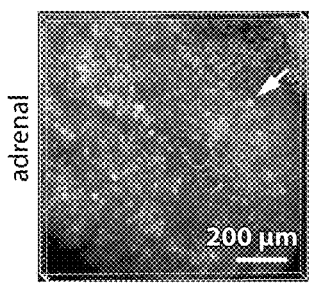
FIGS. 1A-1G depict, in accordance with various embodiments of the invention, applications of whole-organ and whole-organism clearing protocols.
Figure 1C:
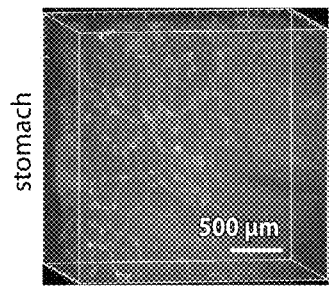
Figure 1E:
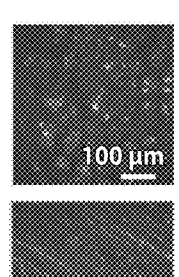
Figure 1B:
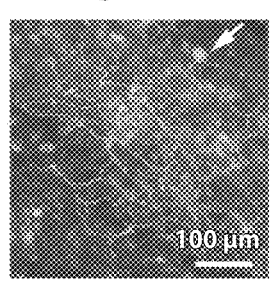
Figure 1D:
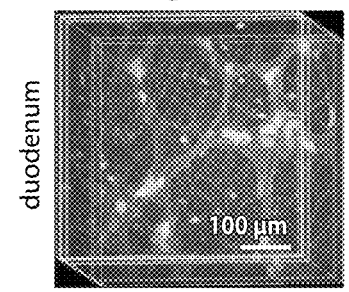

11C) Time to clear for 1 mm sections PACT-processed with all hydrogel embedding and clearing buffer combinations (n=3 for A4P1, A4P2 and Unhybridized. n=4 for all others).

FIGS. 12A-12E depict, in accordance with various embodiments of the invention, PACT compatibility with histological staining. (FIG. 12A, FIG. 12B, FIG. 12C) Representative images of thick section clearing with addition of $CuSO_4$ or 0.2% SB compared to regular PACT. 0.5 mm and 1 mm coronal Thy1-YFP mouse sections are shown after A4P1 hydrogel polymerization (FIG. 12A) and during clearing with 8% SDS-BB (pH 8.5) and subsequent 24 hour incubation in RIMS (FIG. 12B and FIG. 12C for 0.5 mm and 1 mm, respectively). (FIG. 12D) The control, $CuSO_4$, and 0.2% SB treated 0.5 mm slices from (FIG. 12A-FIG. 12B) were immunostained for parvalbumin (see Table 4) and then transferred to RIMS, degassed, and mounted. Shown are 500 μm thick maximum intensity projections of endogenous YFP (cyan) and parvalbumin (red) staining (top) as well as lipofuscin (white) autofluorescence (top and bottom). Red blood cell-derived (e.g. lipofuscin-like) autofluorescence was excited at 561 nm and collected between 562-606 nm. (FIG. 12E) Visualizing endogenous fluorescence and immunostaining deep within thick tissue. A 1 mm thick Thy1-YFP mouse coronal slice was treated with 0.2% SB, A4P1-embedded, cleared with 8% SDS-BB (pH 8.5), immunostained for parvalbumin (see Table 4), and then transferred to RIMS and mounted. Endogenous YFP (cyan) and immunolabeled PV (red) were imaged throughout the slice (left) in a region of the cortex. A 100 μm thick maximum intensity projection (right) was taken at a depth of 500 μm to show representative imaging in the middle of the section. Signal range of the red channel was adjusted for better visualization of PV staining at depth. All sections were imaged on a Zeiss LSM 780 confocal with the Plan-Apochromat 10×0.45 N.A. M27 air objective (w.d 2.0 mm).

FIGS. 13A-13D depict, in accordance with various embodiments of the invention, ePACT: a protocol for tissue clearing through expansion. (FIG. 13A) Fluorescence image of Thy1-YFP expression prior to expansion-clearing. A 70 μm thick maximum intensity projection of five cells expressing YFP represents the standard for imaging pre-expansion. A bright-field image of the pre-expansion 100 μm brain slice is shown in the top right, with the location of the cells being imaged indicated by the red arrowhead. Noteworthy features that may differ between pre- and post-expansion-cleared tissue, such as cell bodies, branching processes, and large projections, are numbered 1, 2, and 3, respectively. (FIG. 13B) Fluorescence image of Thy-YFP expression after 4× expansion-clearing. A 340 μm thick maximum intensity projection of the same five cells in (FIG. 13A) is shown, with the same features labeled again 1, 2, and 3. Of note, a cell body (1) and the neuronal processes of an adjacent cell (2) are both partially obstructed by tissue lipids in (FIG. 13A), but can be easily identified in (FIG. 13B) after clearing and expansion. However, the 4× expansion that contributes to this increased visibility through tissue also causes some tissue destruction, as apparent in the multiple severed processes (such as (2)). A bright-field image of the expanded slice embedded in agarose is shown at the top right. (FIG. 13C) YFP fluorescence from the same cell in pre-expanded (blue box) and post-expanded (yellow box) tissue is shown. (FIG. 13D) Equipment for sample processing: 1) 2% bis-acrylamide, 2) 40% acrylamide, 3) sodium acrylate, 4) ammonium persulfate (APS), 5) N,N,N',N'-Tetramethylethylenediamine (TEMED), 6) 4-hydroxy TEMPO, 7) 20% SDS, 8) collagenase, 9) low gelling temperature agarose, 10) Entellan, and assorted, unlabeled, glass slides, spacers, and plastic dishes. All images were taken on a Zeiss LSM 780 confocal with the Plan-Apochromat 10×0.45 N.A. M27 air objective (w.d 2.0 mm).

FIGS. 14A-14B depict, in accordance with various embodiments of the invention, whole body PARS clearing with borate-buffered detergent. (FIG. 14A) Mice were perfusion-fixed, A4P0-embedded, PARS-cleared for 5 days with 8% SDS-BB (pH 8.5), and washed with 1×PBS at pH 7.5. Numbers correspond to the extracted organs in panel (B). (FIG. 14B) Extracted organs from the cleared mouse in panel (FIG. 14A), pictured before (top) and after (bottom) RIMS incubation for 3 days. Black pointers correspond to the adrenal gland on the kidney and to the ovaries on the fallopian tubes. Each square represents 0.5 $cm^2$. Rodent husbandry and euthanasia conformed to all relevant governmental and institutional regulations; animal protocols were approved by the Institutional Animal Care and Use Committee (IACUC) and by the Office of Laboratory Animal Resources at the California Institute of Technology.

FIGS. 15A-15B depict, in accordance with various embodiments of the invention, small-format antibodies for thick-tissue labeling. (FIG. 15A) For labeling thick tissue sections, camelid nanobodies are a promising alternative to traditional antibodies, either full immunoglobulins or their engineered formats (single-chain variable fragment (scFv), Fab, and F(ab')$_2$). A possible workflow for nanobody production consists of: inoculating 500 ml terrific broth with 5 ml overnight cultures and grow at 37° C. until IPTG induction at OD=0.5, then lowering the temperature to 20° C. for 10 hours for nanobody expression. Cell pellets are then lysed, carried through alternating cycles of freeze-thaw with benzonase addition, followed by a final addition of 0.1% polyethyleneimine to the pellet lysate before pelleting debris and filtering the nanobody-containing fraction. The His-tagged GFAP fusion protein was purified by immobilized metal affinity chromatography on a Ni-NTA column. The His-tag must be removed prior to staining to avoid non-specific binding. (FIG. 15B) To stain for glial fibrillary acidic protein (GFAP) using a GFAP camelid nanobody, 1 mm thick PACT-cleared mouse brain sections were immunostained with 1:500 Atto 488 conjugated GFAP nanobody (see Table 4) at RT overnight with shaking. The stained section was then washed 3 times in PBST over 1 hour, followed by a 1-hour incubation in RIMS. The transparent sections were RIMS-mounted and imaged on a Zeiss LSM 780 confocal with the Plan-Apochromat 10×0.45 N.A. M27 air objective (w.d 2.0 mm). (FIG. 15B, left) 850 μm thick 3D rendering of mouse internal capsule stained with GFAP nanobody. (FIG. 15B, right) Side view showing uniform labeling of GFAP nanobody throughout the entire 850 μm slice.

Figure 9B:
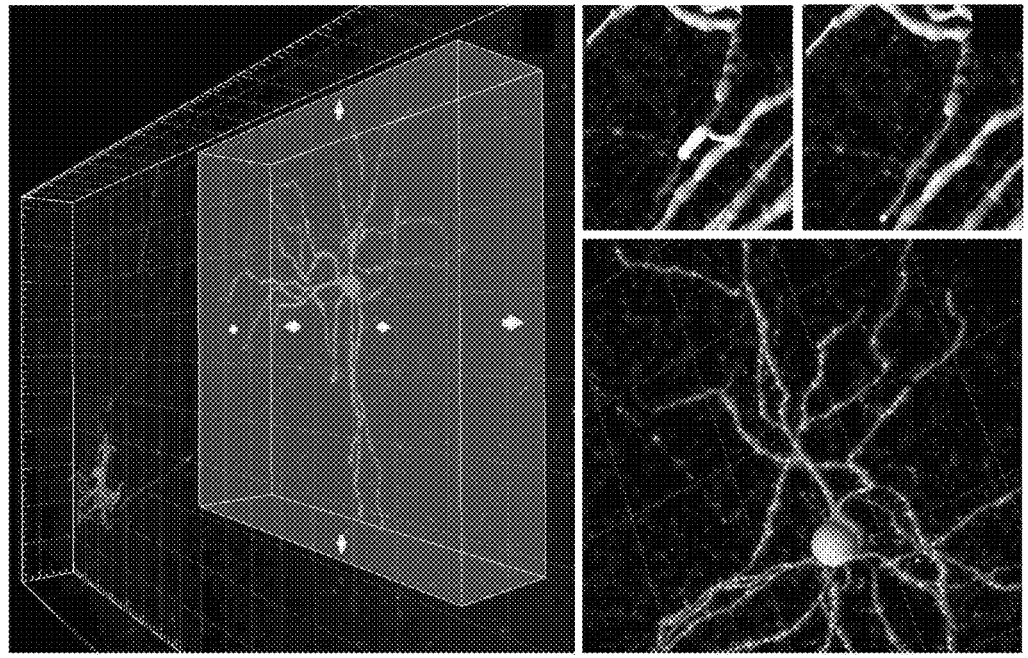
FIGS. 9A-9B depict, in accordance with various embodiments of the invention, two different workflows for cell tracing in neuTube and Imaris.
Figure 9A:
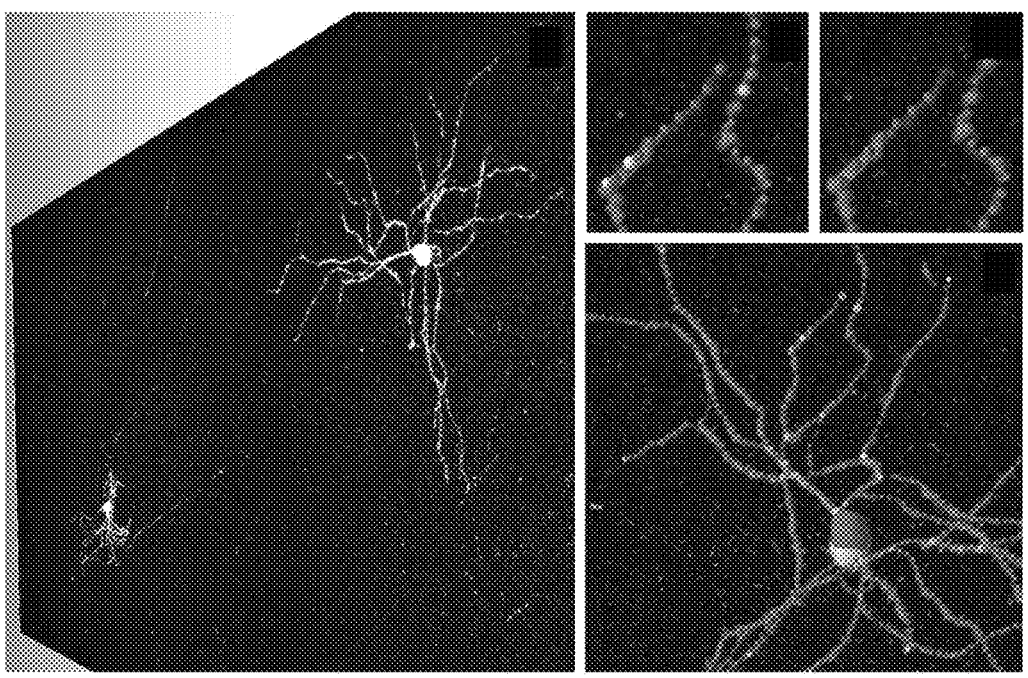
Figure 16A:
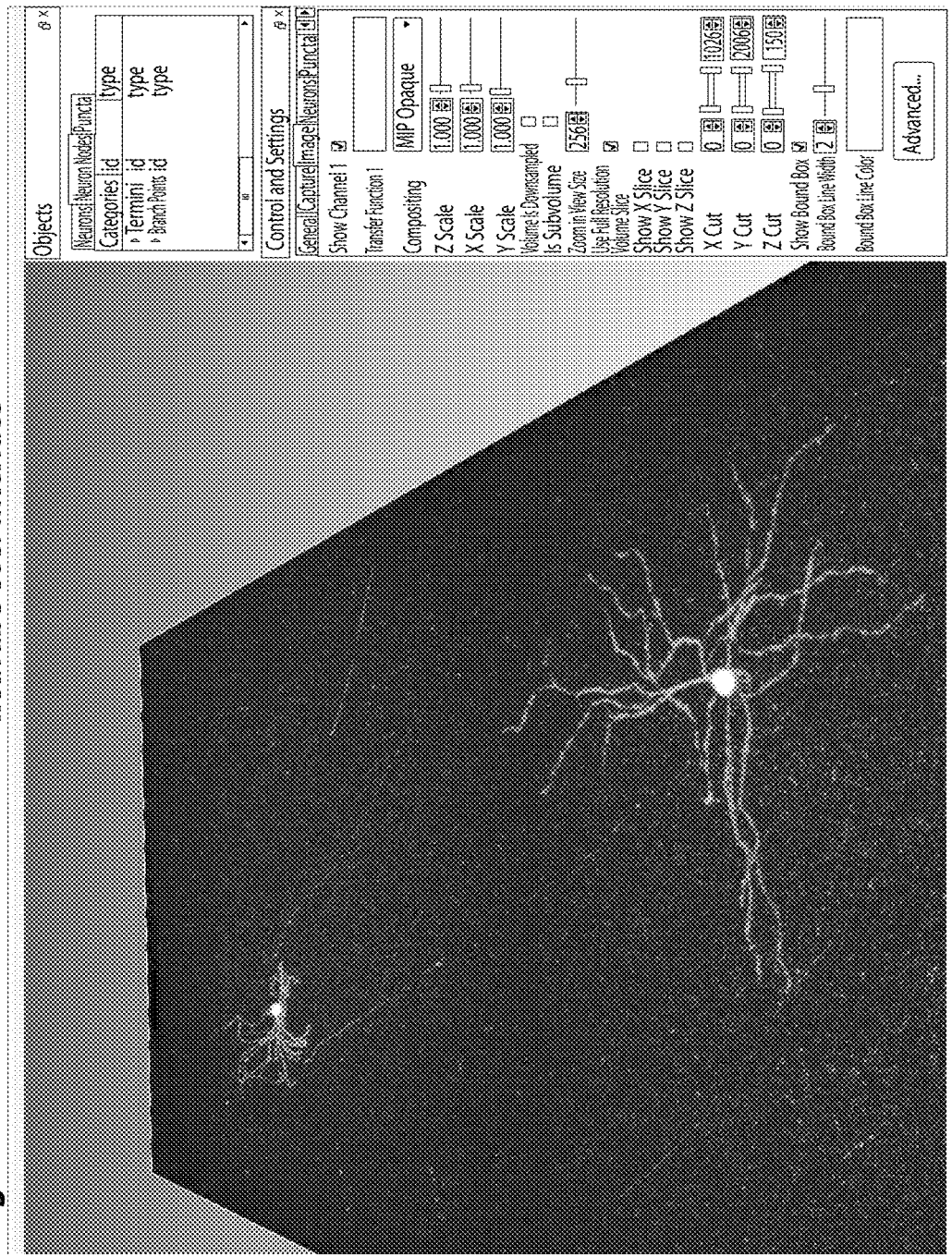
Figure 16B:
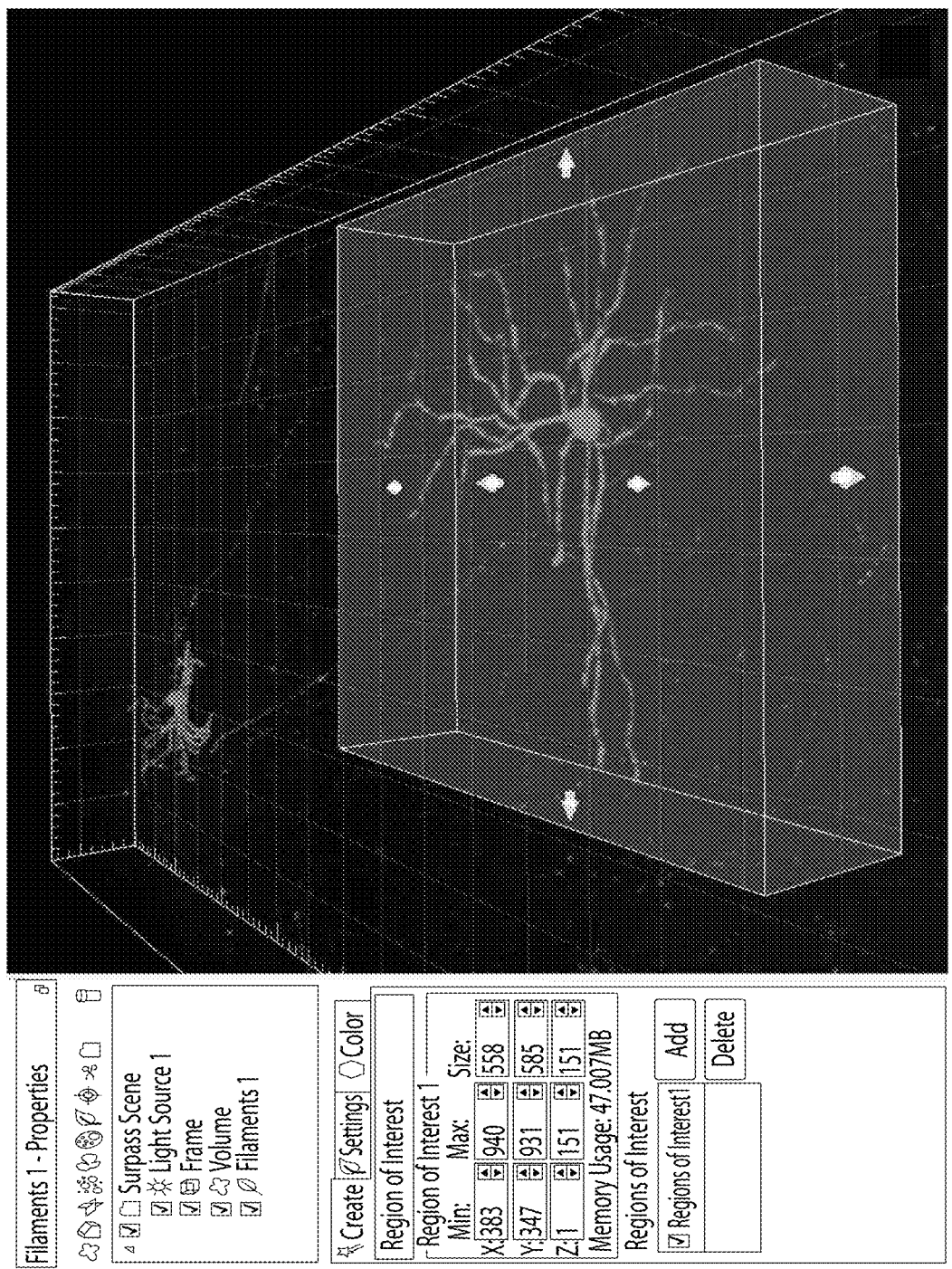

FIGS. 16A-16B depict, in accordance with various embodiments of the invention, user interface elements for image analysis. (FIG. 16A) neuTube. (FIG. 16B) Imaris. Computer screenshots depict the image processing workspace for each software during the 3D visualization of labeled cells in FIGS. 9A-9B.

Figure 17A:
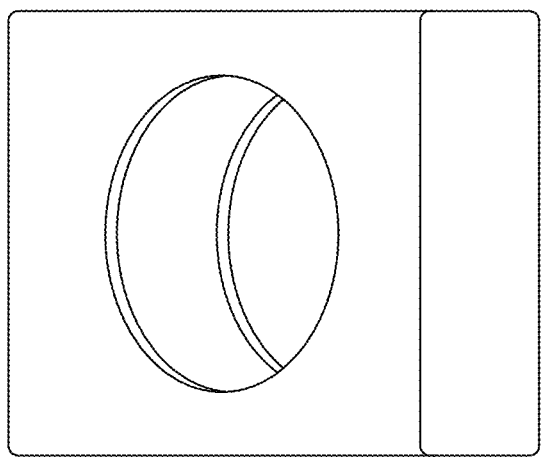
Figure 17B:
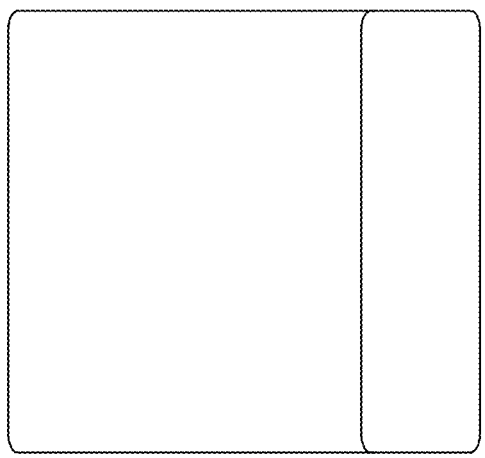

FIGS. 17A-17B depict, in accordance with an embodiment of the invention, (FIG. 17A) an immersion chamber and (FIG. 17B) a sample holder that can be used in conjunction with the light sheet microscope described in FIG. 8.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. March, *Advanced Organic Chemistry Reactions, Mechanisms and Structure* 5$^{th}$ ed.; and Guyton and Hall, *Textbook of Medical Physiology* 12$^{th}$ ed., provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

As used herein, PACT is an acronym for PAssive CLARITY Technique.

As used herein, PARS is an acronym for Perfusion-assisted Agent Release in Situ.

As used herein, RIMS is an acronym for Refractive Index Matching Solution.

As used herein, ePACT is an acronym for expansion-enhanced PACT.

"Mammal," as used herein, refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult, newborn subjects, and unborn subjects whether male or female, are intended to be included within the scope of this term.

"Peripheral organs," as used herein, can include but are in no way limited to muscles, heart, lungs, kidneys, colon, gut, intestines, and the like.

Several methodologies for tissue clearing have been proposed for large-scale 3D mapping of tissue macromolecular content. Each of these protocols offers distinct advantages, such as: preserving tissue architecture, accommodating standard histological techniques, or creating a computational workflow for acquiring and/or reconstructing thick-tissue image stacks. Building on the prior CLARITY technique and concepts for generating extractable tissue-hydrogel hybrids, the trio of PACT (PAssive CLARITY Technique), PARS (Perfusion-assisted Agent Release in Situ), and RIMS (Refractive Index Matching Solution) were developed to offer a user-friendly, rapid approach to rendering whole organs and whole organisms transparent. These methods preserve the macromolecular content of samples, enabling immunohistochemical, single-molecule RNA fluorescence in situ hybridization (smFISH), and small-molecule staining throughout thick tissues, stabilize tissue architecture, complement fluorescent labeling and imaging, and enable long-term storage.

The present application includes additional detailed information about how to implement PACT, PARS, and RIMS. Specific embodiments are set forth below.

ePACT—Enhanced Clearing via Expansion

In various embodiments, the invention teaches a method for clearing and expanding tissue for improved visualization of various constituents of the tissue (e.g., cells, nucleic acids, and other small molecules). In some embodiments, the method includes applying a fixing solution that includes paraformaldehyde (PFA) to the tissue, thereby forming fixed tissue. In some embodiments, the fixing solution includes PFA at a concentration of from 1-15%. In some embodiments, the fixing solution includes glutaraldehyde at a concentration of from 0.1-5%. In some embodiments, the fixing solution includes glutaraldehyde at a concentration of from 0.1-5% and PFA at a concentration from 1-15%. In certain embodiments, the fixing solution includes PFA at a concentration of 4%. In some embodiments, the free aldehydes present in fixed tissue are quenched before subsequent processing steps. In some embodiments, the quenching solution may include glycine. In some embodiments, the tissue is subsequently rinsed with Tris-glycine (0.1-0.3 M glycine with pH adjusted to pH 7.2-8 using Tris-base). In some embodiments, the quenching solution may include ammonium chloride. In some embodiments, the tissue is rinsed for 5 minutes to 5 hours in 0.1 M-1 M glycine and 10 mM-100 mM ammonium chloride in buffer (1×PBS or 1×TBS (tris-buffered saline)). In some embodiments, the quenching solution is 1% sodium borohydride in 1×PBS. In some embodiments, the method further includes permeabilizing the fixed tissue in a solution that includes a surfactant. In some embodiments, the surfactant is a nonionic surfactant. In some embodiments, the nonionic surfactant is Triton X-100. In some embodiments, the solution includes PBST (1×PBS containing 0.1% Triton X-100 (vol/vol)). In some embodiments, the solution may further include 0.1 M-1M glycine. In some embodiments, the solution may include 0.05-5% Triton X-100 and 0.1 M-1 M glycine. In some embodiments, the solution may include 0.1 M-1M lysine in place of glycine. In some embodiments, the tissue is subsequently rinsed with a buffer solution. In some embodiments, the tissue is rinsed with PBS. In some embodiments, the tissue is rinsed with 1×PBS. In some embodiments, once the tissue has been rinsed with a buffer solution, it is incubated in a refractive index matching solution (RIMS). In some embodiments, any appropriate RIMS solution described in the examples set forth herein may be used for this step of the method. In some embodiments, before or after incubation with RIMS, or in the absence of incubation in RIMS, the tissue is incubated in a solution that includes acrylate-acrylamide copolymer (AcAm). In some embodiments, the solution that includes AcAm includes 0-4% acrylamide, 4-10% sodium acrylate, and 0-1% bis-acrylamide. In some embodiments, the solution that includes AcAm includes a buffer. In some embodiments, the solution that includes AcAm is prepared in 1×PBS with 2 M NaCl. In some embodiments, the solution that includes AcAm includes 2.5% acrylamide, 8.625% sodium acrylate, and 0.15% bis-acrylamide in 1×PBS with 2M NaCl. In some embodiments, the solution that includes AcAm further includes a catalyst of polymerization such as TEMED (Tetramethylethylenediamine), and an initiator of polymerization such as the oxidant APS (ammonium persulfate) at approximately equimolar concentrations of 1-10 mM. In some embodiments, a polymerization inhibitor such as 4-hydroxy TEMPO (4-hydroxy-2,2,6,6-tetramethylpiperidin-1-oxyl) is included in the AcAm solution to allow adequate diffusion of hydrogel monomers throughout the sample (i.e., tissue or fixed cells). In some embodiments, the polymerization of the AcAm solution is accomplished via including the following (w/w): 0.01-0.1% 4-hydroxy TEMPO, 0.05-0.2% TEMED, and 0.05-0.2% APS. In some embodiments, potassium persulfate (KPS) or riboflavin (5-10 μg/ml) may be included in the AcAm solution instead of APS. In some embodiments, the solution that includes AcAm further includes the following (w/w): 0.01% 4-hydroxy TEMPO, 0.2% TEMED, and 0.2% APS. In some embodiments, the solution that includes AcAm contains a water-soluble azo initiator such as the thermoinitiator VA-44 (2,2'-Azobis[2-(2-imidazolin-2-yl)propane]dihydrochloride) in place of APS and TEMED. In some embodiments, the solution that includes AcAm further includes 0.5% VA-044. In some embodiments, the tissue is incubated in the solution containing AcAm, polymerization inhibitors (e.g., 4-hydroxy TEMPO) and polymerization initiators for 10-60 minutes or longer at 1-10° C. In some embodiments, immediately following this first incubation, the tissue undergoes a second incubation in fresh solution containing AcAm, polymerization inhibitors (4-hydroxy TEMPO) and polymerization initiators for 10-60 minutes or longer at 1-10° C. In some embodiments, the tissue is incubated in the solution containing AcAm and thermoinitiator for 10-60 minutes or up to 48 hours or longer at 1-10° C. In some embodiments, the tissue is incubated in AcAm and VA-044 for 20-40 minutes at 4° C. In some embodiments, the tissue is further incubated at 35-45° C. until the AcAm is polymerized. In some embodiments, the tissue is purged of free oxygen via degassing under nitrogen for 1-15 minutes at 4-25° C., or incubation in an inert gas atmosphere for 1-24 hours at 4-25° C. In some embodiments, the oxygen-purged tissue is incubated at 37-42° C. until the AcAm is polymerized. In some embodiments, the tissue is incubated for 1-8 hours or longer. In some embodiments, excess gel is removed from around the tissue after polymerization. In some embodiments, after polymerization (and optionally after excess gel has been removed) the tissue is incubated in a 4-10% SDS solution. In some embodiments, the SDS solution is borate-buffered. In some embodiments, the SDS solution includes 4-10% SDS and 0.2 M boric acid buffer. In some embodiments the boric acid buffer is prepared according to the description in the examples set forth herein. In some embodiments, the pH of the SDS solution is 6.5-9.5. In some embodiments, the pH of the SDS solution is 8.5. In some embodiments, the tissue is then incubated in boric acid wash buffer (BBT). In some embodiments, the BBT includes 0.2 M boric acid buffer (prepared as described in the examples set forth herein) and 0.1-0.25% Triton X-100 (vol/vol). In some embodiments, the tissue is incubated in 0.2M boric acid buffer with 0.1% Triton X-100 (vol/vol). In some embodiments, the pH of the BBT is 6.5-9.5. In some embodiments, the pH of the BBT is 8.5. In some embodiments, after incubation in BBT, the tissue is washed in TESCA buffer. In some embodiments, the buffer includes 50 mM TES and 0.36 mM calcium chloride solution. In some embodiments, the TESCA buffer includes 50 mM TES and 0.36 mM calcium chloride solution. In some embodiments, the pH of the buffer is 6.5-9.5. In some embodiments, the pH of the TESCA buffer is 7.4 at 37° C. In some embodiments, the tissue is subsequently incubated in a solution that includes collagenase. In some embodiments, the concentration of collagenase in the solution is 1-10 mg/ml. In some embodiments, the solution that includes collagenase further includes a buffer. In some embodiments, the collagenase is in TESCA buffer. In some embodiments, the tissue is incubated in the solution containing collagenase for 1-48 hours or longer. In some embodiments, the tissue is incubated in a solution that includes collagenase for 12-24 hours. In certain embodiments, after incubation in a solution that includes collagenase, the tissue is soaked in $H_2O$. In some embodiments, the tissue is soaked in dd $H_2O$. In some embodiments, the tissue is soaked in $H_2O$ at a temperature of 20-37° C. for a period of 10-60 minutes, or until expanded to a desired extent. In some embodiments, the tissue is soaked at 23° C. In some embodiments, the tissue is soaked in the absence of light, or with reduced exposure to light. In some embodiments, the tissue used in connection with the aforementioned ePACT methods is animal tissue. In some embodiments, the tissue is mammalian tissue. In certain embodiments, the tissue is brain tissue. In some embodiments, the tissue thickness is 10-2000 μM. In some embodiments, the tissue thickness is 50-150 μM. In certain embodiments, the tissue is 100 μM.

Imaging e-PACT Prepared Tissues

In certain embodiments, the invention teaches imaging a tissue prepared according to the aforementioned ePACT methods. In some embodiments, the tissue embedded in AcAm (described above) is mounted to prevent sample drift during imaging. In some embodiments, the tissue is embedded in agarose. In certain embodiments, the mounted sample is sealed between a coverslip and glass slide, so that the water content of the agarose and of the expanded AcAm tissue-hydrogel remains at a steady-state.

In certain embodiments, one or more cells, cellular components, and other molecules within the tissue are labeled (e.g. with a fluorescent label or by any other means of labeling described in the examples set forth herein) prior to imaging the tissue. In certain embodiments neural circuits are mapped (as described in greater detail in the example section) by imaging the prepared tissue. In some embodiments, one or more nucleic acids (e.g. DNA and/or RNA) within the tissue are visualized. In some embodiments, RNA within the tissue is visualized using single-molecule fluorescence in-situ hybridization (smFISH) (see Skinner, S. O., et al. Measuring mRNA copy number in individual *Escherichia coli* cells using single-molecule fluorescent in situ hybridization. *Nat. Protoc.* 8, 1100-1113 (2013); Lyubimova, A. et al. Single-molecule mRNA detection and counting in mammalian tissue. *Nat. Protoc.* 8, 1743-1758 (2013); Lubeck, E. & Cai, L. Single-cell systems biology by super-resolution imaging and combinatorial labeling. *Nat. Methods* 9, 743-748 (2012); Lubeck, E., et al. Single-cell in situ RNA profiling by sequential hybridization. *Nat. Methods* 11, 360-361 (2014); Ke, R. et al. In situ sequencing for RNA analysis in preserved tissue and cells. *Nat. Methods* 10, 857-860 (2013); Levesque, M. J., et al. Visualizing SNVs to quantify allele-specific expression in single cells. *Nat. Methods* 10, 865-867 (2013); and Levesque, M. J. & Raj, A. Single-chromosome transcriptional profiling reveals chromosomal gene expression regulation. *Nat. Methods* 10, 246-248 (2013)).

In some embodiments, quantitative analysis of multiple transcripts isolated to their subcellular locations, and visualized using smFISH is performed. In certain embodiments, super-resolution microscopy is used to visualize one or more labeled transcripts within tissues that have been prepared according to the ePACT methods described above and in the ensuing examples. Exemplary super-resolution technologies include but are not limited to $I^5M$ microscopy, 4Pi-microscopy, Stimulated Emission Depletion microscopy (STEDM), Ground State Depletion microscopy (GSDM), Spatially Structured Illumination microscopy (SSIM), Photo-Activated Localization Microscopy (PALM), Reversible Saturable Optically Linear Fluorescent Transition (RESOLFT), Total Internal Reflection Fluorescence Microscope (TIRFM), Fluorescence-PALM (FPALM), Stochastical Optical Reconstruction Microscopy (STORM), Fluorescence Imaging with One-Nanometer Accuracy (FIONA), and combinations thereof. Descriptions of relevant techniques can be found in Chi, 2009 "Super-resolution microscopy: breaking the limits, Nature Methods 6(1):15-18; Blow 2008, "New ways to see a smaller world," *Nature* 456:825-828; Hell, et al., 2007, "Far-Field Optical Nanoscopy," *Science* 316: 1153; R. Heintzmann and G. Ficz, 2006, "Breaking the resolution limit in light microscopy," *Briefings in Functional Genomics and Proteomics* 5(4):289-301; Garini et al., 2005, "From micro to nano: recent advances in high-resolution microscopy," *Current Opinion in Biotechnology* 16:3-12; Bewersdorf et al., 2006, "Comparison of I$^5$M and 4Pi-microscopy," 222(2):105-117; and Wells, 2004, "Man the Nanoscopes," *JCB* 164(3):337-340; each of which (including Supplemental Material) is hereby incorporated by reference herein in its entirety. In some embodiments, light sheet microscopy (as described in greater detail in the examples set forth herein) is used to visualize one or more labeled (according to any method described herein) or unlabeled aspect of the tissue or its molecular constituents.

Pre-PACT Tissue Staining to Mask Autofluorescence

In various embodiments, the invention teaches a method for masking autofluorescence of a tissue. In some embodiments, the method includes applying a fixing solution to the tissue, thereby forming fixed tissue, and applying an autofluorescence masking solution to the fixed tissue, thereby forming a masked tissue. In some embodiments, the fixing solution includes PFA. In some embodiments, the autoflouroescence masking solution includes $CuSO_4$ or Sudan Black (SB). In some embodiments, $CuSO_4$ is included at a concentration of 1-10 mM. In some embodiments, the autofluorence masking solution is 10 mM $CuSO_4$. In some embodiments, the autofluorescence masking solution includes 0.01-1.0% SB. In some embodiments, the autofluorescence masking solution is 0.2% SB. In some embodiments, the foregoing autofluorescence masking solution is applied by incubating the tissue in the autoflourosecence masking solution. In some embodiments, the tissue is incubated for 1-72 hours at from 0-23° C. In some embodiments, the tissue is incubated for 48 hours at 4° C. In some embodiments, the masked tissue is then washed or dipped with water to remove excess stain, thereby forming water-treated tissue. In some embodiments, the water-treated tissue is then rinsed in phosphate buffered saline (PBS), thereby forming rinsed tissue. In some embodiments, the PBS is 1×PBS. In some embodiments, the rinsed tissue is then incubated in hydrogel monomer solution that includes acrylamide, thereby forming a hydrogel-treated tissue. In some embodiments, the hydrogel monomer solution includes 1-10% acrylamide and 0-4% paraformaldehyde and 0-1% bisacrylamide. In some embodiments, the hydrogel monomer solution includes 1-10% acrylamide and 1-10% paraformaldehyde. In some embodiments, the hydrogel monomer solution includes 4% acrylamide and 1% paraformaldehyde. In some embodiments, the hydrogel-treated tissue is subsequently incubated in 1-20% sodium dodecyl sulfate (SDS). In some embodiments, the hydrogel-treated tissue is subsequently incubated in 5-15% SDS, thereby forming cleared tissue. In certain embodiments, the hydrogel-treated tissue is incubated in 8% SDS. In some embodiments, the pH of the SDS solution is 6.5-9.5. In some embodiments, the pH of the SDS solution is 8-9. In some embodiments, the pH of the SDS solution is 8.5. In some embodiments, the tissue is brain tissue. In some embodiments, the tissue is any animal tissue. In some embodiments, the tissue is 0.01-5 mm thick. In some embodiments, the hydrogel-treated tissue is incubated in SDS, as described above, for 1-240 hours. In certain embodiments, the hydrogel-treated tissue is incubated in SDS for 12-15 hours. In some embodiments, the hydrogel-treated tissue is incubated in SDS for 24-48 hours. In some embodiments, the hydrogel-treated tissue is incubated in SDS for 72-240 hours. In some embodiments, the cleared tissue is immunostained and/or labeled (before or after clearing) with fluorescent markers, including any immunostains or fluorescent markers described in the examples set forth herein. In some embodiments, the tissue or any component thereof is visualized with microscopy. In some embodiments, the tissue is visualized and/or imaged by any form of microscopy described or referenced herein (e.g. confocal microscopy, light sheet microscopy, super-resolution microscopy, etc.).

In various embodiments, the invention teaches a method for immunostaining tissue prepared according to any of the methods described herein. In some embodiments, the method includes applying a solution that includes a primary antibody to the cleared and washed tissue of the methods described above, thereby forming an antibody-bound tissue. Any suitable antibodies (including small format) and antibody types described or referenced herein can be used in conjunction with the inventive methods. In certain embodiments, the method further includes rinsing the antibody-bound tissue with a buffer solution. In some embodiments, the buffer solution includes PBS. One of skill in the art would readily appreciate that alternative buffer solutions with comparable characteristics could be substituted for PBS. In some embodiments, the method further includes applying a solution that includes a secondary antibody to the antibody-bound tissue that has been washed with buffer solution, wherein the secondary antibody is labeled with a visualizable marker. In certain embodiments, the visualizable marker is fluorescent. One of skill in the art would recognize that any of a number of visualizable markers suitable for labeling antibodies could be used as a substitute for a fluorescent marker. In various embodiments, the primary antibody is labeled with a visualizable marker. In certain embodiments, the tissue is obtained from a biopsy.

In various embodiments, the invention teaches a method for visualizing and/or imaging immunostained tissue. In certain embodiments, the method includes utilizing a microscope to visualize and/or image immunostained tissue prepared according to any of the methods described herein. In certain embodiments, the microscope is utilized to implement a form of microscopy that may include, but is in no way limited to epi-fluorescence microscopy, confocal microscopy, multi-photon microscopy, spinning disk confocal microscopy, light-sheet microscopy, light-field microscopy (including, but not limited to the formats for light sheet microscopy referenced and described in the examples), and Fluorescence Talbot Microscopy (FTM).

The above- and below-described embodiments of immunolabeling with antibodies represent only limited examples of many possible techniques for interrogating tissues and cells that are known in the art. While a number of additional techniques, including utilizing labeled probes of various types, are specifically set forth in the Examples section, they are in no way intended to be limiting. Indeed, any known method for visualizing tissues, cells, or subcellular structures or processes, whether labeled or unlabeled, is intended to be included within the scope of the invention.

PARS, PACT, ePACT, autofluorescence masking, and related methods described herein could be used on any animal, and are in no way limited to those examples specifically set forth herein. Further, the methods described herein can be used for tissues and cells of organisms ranging from embryos to adults.

One skilled in the art will recognize many methods and materials similar or equivalent to those described herein, which could be used in the practice of the present invention. Indeed, the present invention is in no way limited to the methods and materials described herein. Additional non-limiting embodiments of the invention are included in the examples below.

EXAMPLES

Advantages of Tissue Clearing by Tissue-Hydrogel Hybrids

By way of additional background, the tissue stabilization and clearing methods described herein use gentle delivery of structural supportive hydrogels and removal of light obstructing lipids through, importantly, either passive clearing (PACT) or through the vasculature of intact post-mortem organisms (PARS). The hydrogel mesh itself is transparent and secures proteins and nucleic acids into place so they can be later detected with fluorescent labels under a microscope. There are a number of tissue clearing protocols available that combine the use of "chemical" clearing methods (i.e. the modification and/or removal of a tissue components) and "optical" clearing methods (i.e. the homogenization of refractive indices throughout the sample and sample mount, a feat which is usually accomplished through sample hyperhydration, dehydration and/or immersion in specially designed mounting solutions) in order to maximize sample transparency. The inventors experimented with many of these protocols alongside the initial development of PACT and PARS so that they could endeavor to incorporate some of their strengths and avoid major pitfalls. Certain observations are summarized in Table 2 to guide researchers in their selection of a clearing protocol that are suitable for their clearing application.

Emerging from these different approaches to tissue clearing, PACT and PARS are notable for their versatility in preparing a variety of tissue types for high-resolution imaging at depth. The PACT hydrogel formulation and clearing process is modified to render difficult-to-image tissues transparent (e.g. PACT-deCAL, for PACT delipidation and decalcification of bone, as described in PCT/US2015/059600), to expand tissues for better separation of compact structures (e.g. ePACT, for PACT-based expansion clearing of dense cells or projections), and to preserve tissue integrity in fragile samples through varying the degree of paraformaldehyde-tissue crosslinking. Meanwhile, PARS is positioned to tackle a variety of scientific problems that would benefit from a comprehensive, whole-body view of gene expression patterns, cellular organization, and/or structural composition.

Figure 1F:
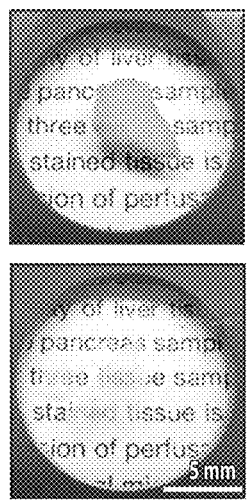
Figure 1G:
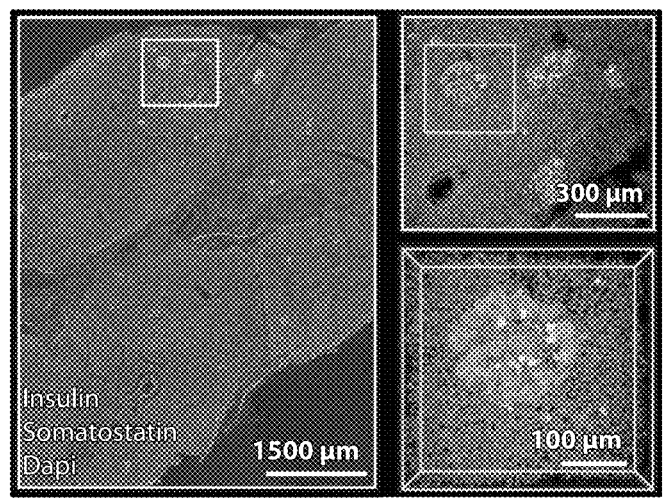
Figure 2A:
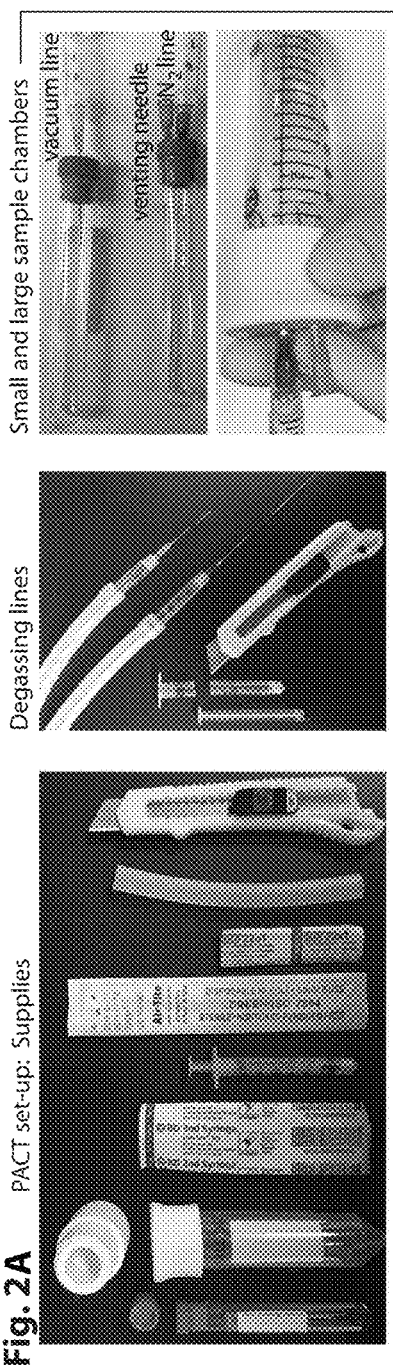
FIGS. 2A-2B depict, in accordance with various embodiments of the invention, PACT set-up and procedure. To successfully hybridize tissue with hydrogel monomers via free-radical polymerization, the sample and hydrogel solution was incubated at 37° C. in an oxygen-depleted environment. This is accomplished within an air-tight container that permits sample degassing.
Figure 2B:
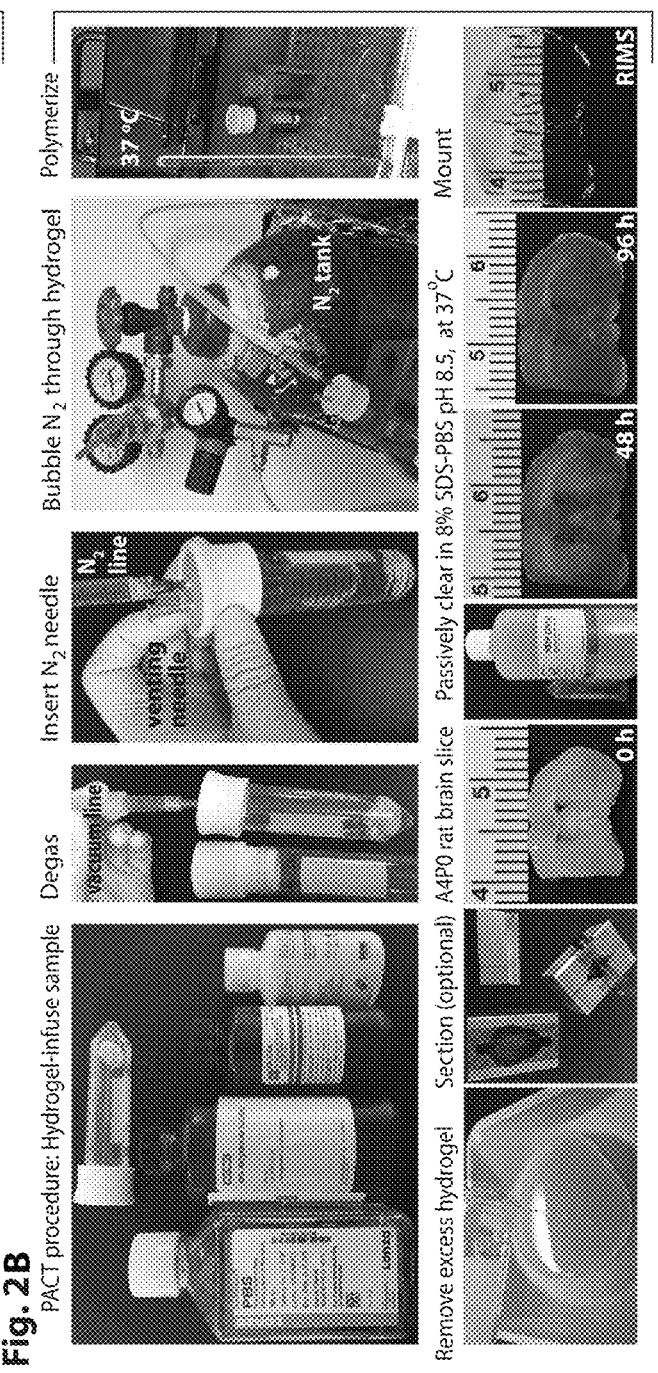

PACT- or PARS-based preparation and clearing of tissue, followed by tissue mounting in RIMS, can preserve the signal from native fluorescent proteins (FIG. 1A) and improve the efficacy of post-clearing immunofluorescent labeling (FIG. 1G). Fluorescence signal intensity is also maintained through month-long storage periods post fixation. Other brain-specific tissue clearing protocols (Table 2) have at least one functional drawback, such as incompatibility with endogenous fluorescent labels. Some of these limitations have been overcome by the use of automated tissue sectioning techniques which have been successfully used in tracking long-range projection axons and sparse cell populations throughout whole-brains in rodents or human brain sections, or adapted to mapping the cellular organization and sensory innervation of peripheral whole-organs in mammalian tissues. These heavily automated imaging systems are not readily available to biology/clinical laboratories with limited resources and budget. Conversely, traditional histology relies on the irreversible sectioning and manual reconstruction of successive slides for image analysis, which is time-consuming and potentially loses molecular information and connectivity in the process. PACT, PARS and RIMS enable deep imaging of large tissue samples without sectioning and reconstruction. Antibody expense aside, these cost-effective techniques generate detailed 3D reconstructions of intact circuits using only mainstream single-photon microscopy.

Experimental Design

In various embodiments, the procedures described below include 7 main stages: tissue preparation (steps 1-5); formation of a tissue-hydrogel matrix (step 6); tissue clearing (step 7-8); staining (steps 9, optional); enhancement of optical clarity using RIMS (refractive index matching solutions; steps 10-13); imaging (step 14); and image visualization and analysis (steps 15-17). Whilst PACT and PARS, including their respective tissue-specific variations (PACT-deCAL, PARS-CSF), each follow the same main stages, the decision to proceed with PACT or PARS is generally made prior to commencing the procedure. If the primary goal is to stabilize soft and/or amorphous samples (e.g. thymus, spleen, pancreas) for experimentation and sectioning, and not to enhance tissue transparency for imaging, users may process samples according to steps 1-6 (PACT or PARS).

Most steps of the procedure can be performed by all members of the research community. Aspects of the PARS set-up (steps 1-5) require that the scientist be approved for working with laboratory animals and/or possess the surgical dexterity to establish an intravascular route for delivery of PARS reagents. For example, to execute PARS-based clearing of whole laboratory animals (e.g. rodents, non-human primates) via transcardial perfusion or cannulation, the researcher should be proficient in conducting animal euthanasia via transcardial perfusion and/or basic animal surgical techniques and practices.

Since whole organ and thick-tissue imaging can generate terra-scale datasets, a computational or informatics background, though not necessary if relying on commercial software with good technical support, is very helpful in managing large datasets (file handling and file storage) and in performing image analysis (steps 15-17).

PACT or PARS

Figure 7B:
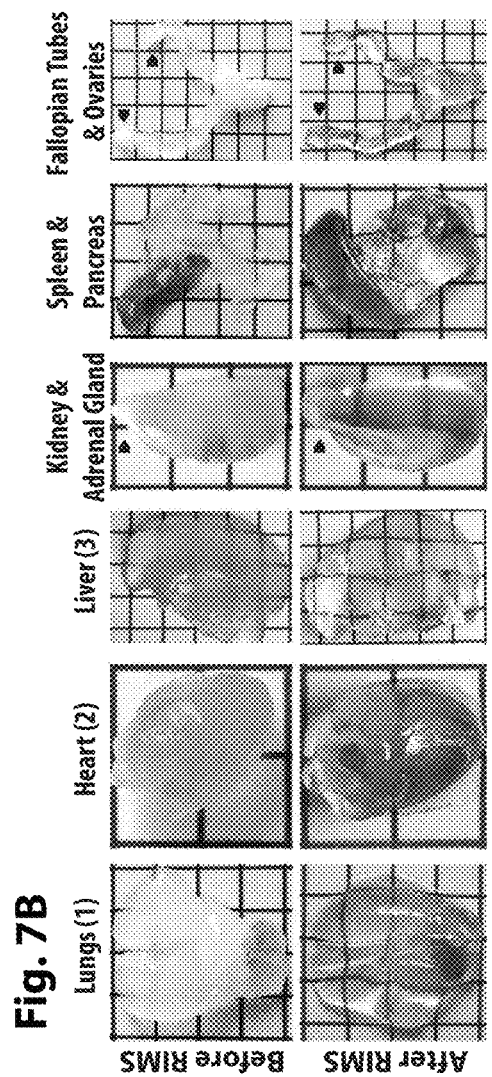
FIGS. 7A-7B depict, in accordance with various embodiments of the invention, whole-body clearing of mice with PARS.
Figure 7A:
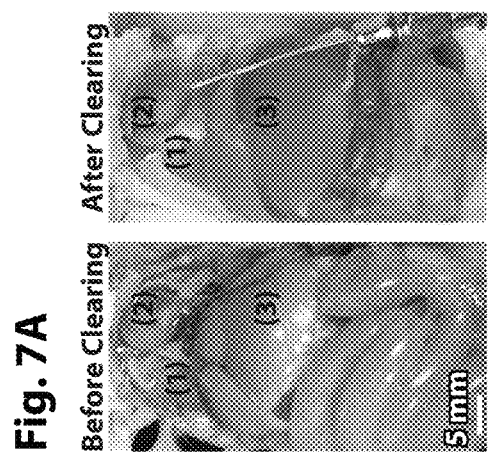

Without the use of organic solvents, passively clearing and immunostaining larger tissue volumes (e.g. whole organs) can be very slow. In terms of clearing efficiency, PACT (FIG. 1F-G, FIG. 2-5, FIG. 10-13) is well-suited for the quick clearing of small tissue sections (e.g. up to 1-3 mm thick-sectioned organs (FIG. 10) or tissue biopsies (FIG. 1F-G)). For whole organ screening or profiling tissues throughout the entire organism, PARS greatly accelerates and simplifies the clearing process. All hydrogel monomer solutions, wash buffers, buffered detergents, and phenotypic labels are driven throughout tissue vasculature via a perfusion-based pressure gradient (FIG. 6), which under whole-mouse or whole-rat PARS clearing, renders most organs transparent within four days (FIG. 7, FIG. 14). To achieve these PARS clearing rates via PACT, excised organs would need to be thick-sectioned and processed individually or in batches, as for most other tissue-clearing protocols. Although the PARS set-up is more involved than PACT, with the PARS tubing and reagent levels requiring attentive, daily monitoring, all organs are processed simultaneously and cleared rapidly and consistently via a single perfusion line. Also, the basic PARS system can be obtained through the repurposing of common laboratory items (see FIG. 6) and standard protocols (transcardial perfusion) within biomedical research.

Tissue Stabilization by the Formation of a Tissue-Hydrogel Matrix

Figure 4A:
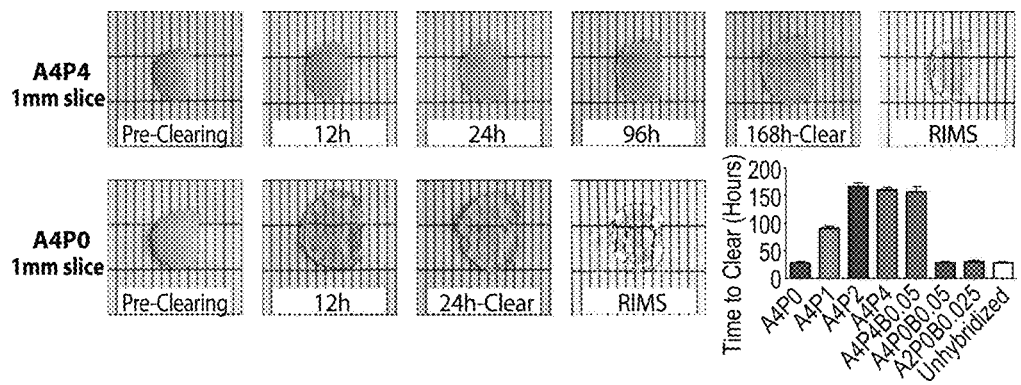
FIGS. 4A-4D depict, in accordance with various embodiments of the invention, clearing time course and antibody penetration of PACT-processed samples. Quantitative comparison of the effect of different hydrogel embedding conditions and clearing buffers on time to clear and antibody penetration during immunostaining. 1 mm thick mouse coronal slices were hybridized and cleared with the array of previously used PACT conditions (FIG. 3). Slices were monitored for the time they took to become transparent. Once cleared, slices were washed and then immunostained.
Figures 11A, 11B, 11C:
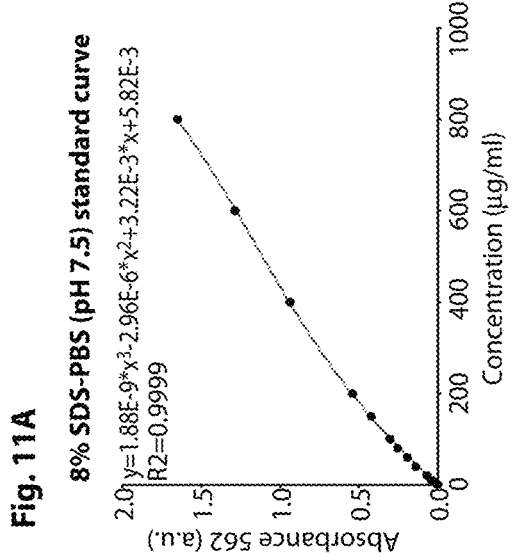
FIGS. 11A-11C depict, in accordance with various embodiments of the invention, protein loss over the course of PACT clearing. The amount of protein lost while clearing was measured by performing a BCA on the clearing buffer, which was collected and replaced periodically while 1 mm tissue samples were undergoing PACT. A standard curve of BSA protein concentration in each of the four different clearing buffers was generated. Standard curves were fit with a third order polynomial and used to extrapolate all protein loss measurements.

In unstabilized tissue, the prolonged incubation in detergent at 37° C. required for PACT and the perfusive force used in PARS would be detrimental to tissue integrity. Thus, the hybridization of amine-containing and paraformaldehyde (PFA)-crosslinked biomolecules to a hydrogel scaffold serves to stabilize tissue architecture and non-lipid content throughout all aspects of PACT and PARS tissue processing. During PARS, the rodent's intact connective tissue and inflexible skeleton provide an additional degree of structural support. To support rapid delipidation in the absence of potentially tissue damaging electrophoretic clearing (ETC), the composition of the PARS/PACT hydrogel monomer solution bares a few major changes from the originally proposed CLARITY hydrogel, which consists of 4% acrylamide, 4% PFA, and 0.05% bis-acrylamide (A4P4B0.05). First, the crosslinker bis-acrylamide should be excluded from the PARS hydrogel formulation to prevent hydrogel blockages in vasculature and perfusion lines. Its exclusion from the PACT hydrogel as well, and the reduced exposure of tissues to PFA in both protocols accelerates clearing and immunolabeling steps. With a final composition of 4% acrylamide and 0% PFA (A4P0), the resulting minimal polymeric scaffold of the PARS and PACT tissue-hydrogel matrices suffices not only to retain tissue proteins (FIG. 3A, FIG. 11) and stabilize tissue macrostructure during clearing, but it also allows SDS micelles to diffuse more freely through tissue for efficient clearing (FIG. 4A, FIG. 11C, FIG. 7). Similarly, a lower crosslink density ensures that antibodies can better access tissue epitopes during immunolabeling (FIG. 4B-D, FIG. 12E).

Tissue Clearing

Traditionally, tissue clearing protocols have aimed to render samples transparent via homogenizing the refractive indices (RI) of the various tissue components, and matching their RI with the lens and mounting set-up (e.g. glass coverslip interfaces). This has often been accomplished via exchanging the aqueous fraction of tissue (RI~1.33) with a mounting medium of higher refractive index, which includes organic solvents such as BABB (RI~1.53-1.57), dibenzyl ether (RI~1.56), methyl salicylate (RI~1.52-1.54), and 2,2'thiodiethanol (RI~1.52); polyol and saturated sugar solutions such as glycerol (RI~1.43-1.47), sucrose and fructose (RI~1.49-1.50); and amides such as formamide (RI~1.44) and urea (RI~1.38). Aside from passive CLARITY and PACT, few passive clearing protocols endeavor to alter the chemical composition of tissue, removing major tissue components from samples so that they become less light-scattering (see "chemical clearing" in Table 2). One notable example is CUBIC which also combines the use of passive delipidation and refractive index matching to achieve transparency. Thus, the inventors sought to compare the level of delipidation that was achieved with PACT-based clearing (A4P0 and A4P4 hydrogels) and CUBIC-based clearing. To examine the efficacy of tissue delipidation, transmission electron microscopy (TEM) was used (FIG. 5B, Supplementary Methods). Indeed, as illustrated by membrane permeabilization and extraction, lipid removal was noticed in all conditions and was highest in A4P0, where a high degree of fine structure loss is evident. In contrast, A4P4 tissue, although extracted, still retains enough contrast for identifying fine structural detail, such as membrane-bound organelles and small neurites. With respect to structural preservation, the CUBIC samples are between the two PACT conditions, showing nearly complete lipid extraction but with some cytoskeletal elements in the axon preserved. Although samples embedded in A4P0 hydrogel showed adequate protein and nucleic acid retention for imaging endogenous fluorescence (FIG. 5C) and detecting myelin binding proteins (FIG. 5D), if an enhanced level of tissue preservation is desired, it is helpful to embed samples in a hydrogel with a higher order of tissue crosslinking by including PFA. Alternatively, samples can be processed in parallel, and adjacent areas can be directed either to TEM or to A4P0-4 clearing to obtain both ultrastructural and volume information respectively.

The denaturing anionic detergent sodium dodecyl sulfate (SDS) used for lipid removal in PACT/PARS is also very effective in dissociating DNA from proteins (e.g. for cell nuclei removal) and disrupting extracellular matrices to facilitate protein removal (e.g. ionic interactions of SDS with membrane proteins allow for their removal and purification). For example, retrograde perfusion of a cadaveric rat heart with 1% SDS for 12 hours results in its complete decellularization. By contrast, SDS solubilization of lipid bilayers via a micellar mechanism, is a slower process. Thus, to guard against the extraction of peptide and nucleic acid content during SDS clearing, it is important that non-lipid tissue components have been hybridized to a hydrogel scaffold.

The CLARITY protocol featured a hydrogel monomer solution composed of 4% acrylamide, 4% PFA and 0.05% bis-acrylamide (A4P4B0.05), which confers dense tissue-hydrogel crosslinking. The advanced CLARITY protocol suggests decreasing acrylamide concentrations to as low as 0.5% (A0.5P4B0.0125) when clearing is performed passively rather than with ETC-based rate enhancement. Following the initial, thorough perfusion-fixation step with 4% PFA, PACT and PARS tissues are infused with A4P0 monomer. The inventors have not found the addition of bis-acrylamide to be beneficial in preventing protein loss (FIG. 3A) in either A4P0-hybridized (A4P0B0.05) or A4P4-hybridized (A4P4B0.05) tissues. Furthermore, although protein retention is similar for all A4P0-A4P4 formulations (FIG. 3A), higher concentrations of PFA, which anchors tissue to the hydrogel mesh and increases tissue crosslinking, results in enhanced fine structure preservation (FIG. 5B) and limits anisotropic tissue-hydrogel expansion (FIG. 3B-C). The resulting less porous tissue-hydrogel matrix curtails protein solubilization by SDS (FIG. 3A, FIG. 11B), however clearing speed (FIG. 4A, FIG. 11C), overall tissue transparency (FIG. 4A), and the efficiency of antibody labeling (FIG. 4B-D) are all reduced. Thus, PFA-containing hydrogel formulations are especially useful for samples that will be used for in-depth profiling of fine structures, where protein and nucleic acid retention is of maximum importance.

The Importance of pH and Temperature in Clearing

In the procedure, the inventors describe two modes of detergent-based tissue clearing: passive lipid removal (PACT: step 6 option A for hydrogel permeation and embedding, step 7 option A for PACT clearing), and active delipidation (PARS: step 6 option B for hydrogel perfusion and embedding, step 7 option C for PARS clearing). Several factors, including the chemical properties of the detergent solution, the pH of the detergent solution, and the tissue components to be extracted (i.e., peptide, lipid, nucleic acid), affect micelle formation and composition, and hence clearing efficiency. The role of pH is elevated in scenarios, such as tissue clearing, where relatively high SDS concentrations (4-8% SDS) are employed. A slightly basic clearing solution will help to counteract proton build-up at the negatively charged surface of SDS micelles. Conversely, a clearing solution that becomes too acidic has the potential to impair lipid extraction via disrupting the structure of the ionic micelles, as well as to encourage protein extraction via their denaturation and release from membranes. For these reasons, and to avoid damage to tissue and to endogenous fluorescent proteins, it is helpful to maintain a physiological to slightly basic pH during tissue clearing. Merely by way of non-limiting examples, among the alkaline buffers well suited for PACT and PARS are 0.2 M boric acid (pH=8.5) and 0.01 M PBS (pH=7.5, 8.5), with the more basic 8% SDS solutions offering a slight rate enhancement to delipidation (FIG. 11C).

Temperature represents a second important factor that influences the solubilization process, and in particular, the micellular composition. For SDS in aqueous medium, the average micelle volume decreases but the total number of micelles increases as the temperature rises. It is hypothesized that smaller micelles may more readily diffuse through the tissue-hydrogel matrix, and so increasing the temperature of the clearing bath will accelerate lipid extraction. Higher temperatures (~50° C.), which may enhance clearing efficiency will promote protein denaturation, which has the potential to damage relevant protein epitopes or incur fluorescent protein signal loss. Thus, both PACT and PARS clearing steps are performed at 37° C. To accelerate lipid extraction, the concentration of SDS is raised from 4% to 8% SDS relative to CLARITY, which has a similar effect as raising the clearing temperature.

Labeling

PACT and PARS-prepared tissues are amenable to most standard histological techniques, including those which employ immunohistochemical, small-molecule, and fluorescent protein-based labels, as well as brightfield stains. Small-molecule dyes such as nuclear stains rapidly distribute throughout thick tissue sections, such that hour-long to overnight incubations are sufficient for most samples. The slow diffusion of full-format antibodies (150 kDa) through thick samples, and their tendency to denature and degrade over time, necessitates the use of, on average, 10-fold more concentrated antibody dilutions in primary and secondary incubations of thick sections than in 40 μm thin sections. The use of smaller antibody formats (fragment antigen-binding (Fab): 55 kDa, Fab dimer (F(ab')$_2$): 110 kDa,) for secondary antibody labeling is suggested, particularly given their commercial availability. Herein, we can achieve adequate labeling of 1 mm thick sections by Fab format antibodies within 48 hours. Even smaller formats, most notably camelid nanobodies (15 kDa) are well suited for labeling thick tissue (FIG. 15) since at 10× smaller than full IgGs, they penetrate tissue rapidly and thoroughly. Also, their stability (e.g. over a wide pH range, at high concentrations, and at temperatures of up to 90° C.) and protease resistance allows them to remain intact throughout long incubations conducted at room temperature (RT) (FIG. 15B).

Enhancement of Optical Clarity

Infusing and mounting cleared tissues in RIMS helps to minimize the mismatch between the refractive indices of the sample and the microscope objective. This so-called "optical clearing", which is detailed in steps 10-13, greatly enhances the optical clarity of cleared samples (see FIG. 1A-E, FIG. 2B, FIG. 4, FIG. 5A, FIG. 5C-D, FIG. 7, FIG. 8C, FIG. 12, FIG. 14, FIG. 15B). One could substitute a different mounting solution for RIMS (e.g. sRIMS (see FIG. 1F-G), cRIMS, glycerol dilution, FocusClear, Cargille Labs optical liquids, 2,2'-thiodiethanol). Optional: measure the RI of the chosen mounting media using a refractometer; dilute glycerol with dd H$_2$O to the same RI, and use this glycerol dilution as the immersion media for dipping objectives.

Imaging

To use tissue clearing to its best advantage, the microscope set-up must be capable of acquiring high-resolution image stacks through thick, cleared samples. Of utmost importance are the detection optics. A high numerical aperture (N.A.~1.0) and long-working distance (w.d.=5-10 mm) objective will provide high resolving power even when viewing deep tissue structures. In addition, since objectives are designed according to the optical properties of a target sample and sample mount, an objective that has been optimized to the RI range of the RIMS-mounted tissue and immersion media (RI~1.46-1.49) will minimize spherical aberrations, maximize lateral and axial resolution, and help to preserve fluorescent signal intensity while imaging through thick, cleared tissues. To this end, numerous manufacturers have developed specialized multi-immersion and air objectives well-suited to imaging PACT- and PARS-cleared fluorescent samples at depth: e.g. Olympus CLARITY-optimized 25×0.95 N.A. objective (w.d. 6.0 mm), Olympus 10×0.6 N.A. UIS2-XLPLN10XSVMP and 25×0.95 N.A. UIS2-XLSLPLN25XGMP objectives (w.d. 8.0 mm) for samples with RI~1.33-1.52 and RI~1.41-1.52, Leica HC FLUOTAR L 25×1.0 N.A. IMM motCORR VISI (w.d. 6.0 mm) for samples with RI=1.457, Zeiss Scale-optimized 20×1.0 N.A. objective (w.d. 5.6 mm) for samples with RI=1.38, Zeiss CLARITY/CUBIC-optimized EC Plan-NEOFLUAR 5×0.16 N.A. objective and LSFM Clearing 20×1.0 N.A. objective (w.d. 5.6 mm) for samples with RI=1.45.

Imaging cleared tissues via two-photon or confocal microscopy can generate extremely high resolution data sets. However, these imaging modalities are time-consuming, particularly when scanning a large field of view at depth. Light sheet fluorescence microscopy (LSFM) permits rapid scanning through comparatively large sample volumes, which alleviates the imaging bottleneck that can occur with the high-throughput preparation of cleared samples. Also, because image acquisition requires only brief plane-illumination, LSFM minimizes sample photobleaching, a major drawback in using point-scanning confocal systems to image large fluorescently labeled samples. Given the widespread availability of confocal microscopes but the obvious benefits of LSFM, imaging guidelines are provided for each system as well as design schematics for a cost-efficient LSFM system.

Data Analysis

Following on the heels of the "OME" focus of the last few decades and spurred by the efforts of the BRAIN Initiative (http://www<dot>braininitiative<dot>nih<dot>gov/index<dot>htm), the Human Brain Project (https://www<dot>humanbrainproject<dot>eu), and the Allen Brain Institute, the quest to map the human connectome has recently taken center stage. It is unlikely that the connectome project can be tackled by a select few taking a top-down approach, as was possible in the elucidation of the human genome. Instead, by tasking multiple groups with mapping discrete neural circuits, one can envision the draft of a connectome gradually emerging through stitching together these individual wiring diagrams (e.g. www<dot>openconnectomeproject<dot>org). When combined with long-working-depth objectives and high-throughput imaging (LSFM, e.g. CLARITY Optimized Light sheet Microscopy (COLM); and the custom-made, economical system (presented here in FIG. 8)), PACT and PARS provide a means for efficiently acquiring information on the spatial position of neurons within large tissue volumes at high resolution. For this information to be applied to mapping the connectome, however, these gigabytes or even terabytes of raw image data (e.g. for a whole mouse brain at 25× magnification) must be converted into a complex network of neuron projection pathways and neural contacts, a feat that poses significant demands on both storage hardware and image analysis software. Many available software tools and image file formats were not designed with terra-scale datasets in mind and assume that entire image volumes fit in computer RAM.

To this end, a range of software packages were evaluated for processing, visualization and analysis of cleared brain volumes, including both general image processing platforms and more specialized tools focused on stitching or filament tracing. Table 3 includes a summary list of those tools that were found to be stable, functional, user friendly and well supported. For general image analysis Fiji (see Schindelin, J. et al. Fiji: an open-source platform for biological-image analysis. *Nat. Methods* 9, 676-682 (2012).) is recommended (a distribution of ImageJ (see Schneider, C. A., Rasband, W. S. & Eliceiri, K. W. NIH Image to ImageJ: 25 years of image analysis. *Nat. Methods* 9, 671-675 (2012)) and Vaa3D (see Peng, H., Bria, A., Zhou, Z., Iannello, G. & Long, F. Extensible visualization and analysis for multidimensional images using Vaa3D. *Nat. Protoc.* 9, 193-208 (2014); and Peng, H., Ruan, Z., Long, F., Simpson, J. H. & Myers, E. W. V3D enables real-time 3D visualization and quantitative analysis of large-scale biological image data sets. *Nat. Biotechnol.* 28, 348-353 (2010)) which are open source, extensible platforms for image analysis and visualization that have a rich collection of plugins for carrying out specific tasks including stitching and fiber tracing (see Longair, M. H., Baker, D. A. & Armstrong, J. D. Simple Neurite Tracer: open source software for reconstruction, visualization and analysis of neuronal processes. *Bioinformatics* 27, 2453-2454 (2011); Dercksen, V. J., Hege, H. C. & Oberlaender, M. The Filament Editor: an interactive software environment for visualization, proof-editing and analysis of 3D neuron morphology. *Neuroinformatics* 12, 325-339 (2014); and Peng, H. et al. Virtual finger boosts three-dimensional imaging and microsurgery as well as terabyte volume image visualization and analysis. *Nat. Commun.* 5, 4342 (2014)).

neuTube (see Feng, L., Zhao, T. & Kim, J. neuTube 1.0: a New Design for Efficient Neuron Reconstruction Software Based on the SWC Format. eneuro, DOI: 10.1523/ENEURO.0049-1514.2014 (2015)) is recommended for semi-automated tracing of neurites (FIG. 9). Commercial software packages Imaris (Bitplane) (see Feng, L., Zhao, T. & Kim, J. neuTube 1.0: a New Design for Efficient Neuron Reconstruction Software Based on the SWC Format. eneuro, DOI: 10.1523/ENEURO.0049-1514.2014 (2015)) and Neurolucida (see Glaser, J. R. & Glaser, E. M. Neuron imaging with Neurolucida—a PC-based system for image combining microscopy. *Comput. Med. Imaging Graph.* 14, 307-317 (1990)) provide similar functionality, currently offer better support for very large image files, and can be more stable and user friendly (FIG. 9, FIG. 16)—making them a good starting point for laboratories with less image processing expertise.

Image Stitching

Confocal and light sheet microscopes equipped with motorized stages usually support tiled acquisition, which is essential for imaging large volumes at cellular resolution. These tiles can then be aligned to pixel accuracy and blended together using microscope acquisition software: e.g. Leica Application Suite (Leica Microsystems) (see Bria, A. & Iannello, G. TeraStitcher—a tool for fast automatic 3D-stitching of teravoxel-sized microscopy images. *BMC Bioinformatics* 13, 316 (2012).), Zen (Zeiss) (see Glaser, J. R. & Glaser, E. M. Neuron imaging with Neurolucida—a PC-based system for image combining microscopy. *Comput. Med. Imaging Graph.* 14, 307-317 (1990), cellSense (Olympus) (see Yu, Y. & Peng, H. Automated high speed stitching of large 3D microscopic images in 2011 *IEEE International Symposium.* 238-241 (2011)), NIS Elements (Nikon Instruments) (see Peng, H. et al. Virtual finger boosts three-dimensional imaging and microsurgery as well as terabyte volume image visualization and analysis. *Nat. Commun.* 5, 4342 (2014)) or offline using open-source tools such as the TeraStitcher (see Bria, A. & Iannello, G. TeraStitcher—a tool for fast automatic 3D-stitching of teravoxel-sized microscopy images. *BMC Bioinformatics* 13, 316 (2012)), Vaa3D iStitch plugin (see Yu, Y. & Peng, H. Automated high speed stitching of large 3D microscopic images in 2011 *IEEE International Symposium.* 238-241 (2011)), ImageJ stitching plugin (see Preibisch, S., Saalfeld, S. & Tomancak, P. Globally optimal stitching of tiled 3D microscopic image acquisitions. *Bioinformatics* 25, 1463-1465 (2009)), XuvTools (see Emmenlauer, M. et al. XuvTools: free, fast and reliable stitching of large 3D datasets. *J. Microsc.* 233, 42-60 (2009)), or μManager Multi Channel Shading plugin (see https://micro-manager<dot>org/wiki/MultiChannelShading and see the Vale laboratory's "How to Acquire Flat Field Correction Images" at http://nic<dot>ucsf<dot>edu/dokuwiki/doku.php?id=flatfieldimageacquisition).

When stitching together multiple tiles, systematic variations in brightness across the image field caused by non-uniform illumination, vignetting, or imprecise optical alignment often result in significant variations in image brightness that can make downstream visualization and processing difficult. One solution is to capture smaller tiles from the central field of view where illumination tends to be more uniform. However, this increases capture time since, for example, reducing the field of view to the center ⅓ requires capturing and stitching 9× as many tiles. An alternate approach is to directly measure the illumination profile using a uniform calibration slide (e.g. see protocols (see Model, M. A. & Blank, J. L. Concentrated dyes as a source of two-dimensional fluorescent field for characterization of a confocal microscope. *J. Microsc.* 229, 12-16 (2008)) and "How flat is your confocal illumination profile? Want to find out?" at http://www<dot>spectral<dot>ca/Downloads?f=2745809748.pdf) or CIDRE (see Smith, K. et al. CIDRE: an illumination-correction method for optical microscopy. *Nat. Methods* 12, 404-406 (2015), and then to apply the estimated correction to each acquired image tile. This so-called "flat field" or shading correction from a reference image is often supported by acquisition software: e.g. μManager Multi Channel Shading plugin (see http://nic<dot>ucsf<dot>edu/dokuwiki/doku.php?id=flatfieldimageacquisition and), shading reference in NIS Elements (Nikon Instruments), Leica Application Suite (Leica Microsystems) (see Bria, A. & Iannello, G. TeraStitcher—a tool for fast automatic 3D-stitching of teravoxel-sized microscopy images. *BMC Bioinformatics* 13, 316 (2012)), Zen (Zeiss) (see Glaser, J. R. & Glaser, E. M. Neuron imaging with Neurolucida—a PC-based system for image combining microscopy. *Comput. Med. Imaging Graph.* 14, 307-317 (1990)), cellSense (Olympus) (see Yu, Y. & Peng, H. Automated high speed stitching of large 3D microscopic images in 2011 *IEEE International Symposium.* 238-241 (2011)); or can be carried out using an offline workflow: e.g. with ImageJ ImageCalculator, see "How to correct background illumination in brightfield microscopy" by G. Landini at http://imagejdocu<dot>tudor<dot>lu/doku.php?id=howto:working:how_to_correct_background_illumination_in_ brightfield_microscopy.

Visualization

Image stacks can be visualized using commercial software such as Imaris (Bitplane), Amira (FEI), MetaMorph (Molecular Devices) and others (Zen (Zeiss), Leica Application Suite (Leica Microsystems), NIS Elements (Nikon Instruments), cellSense (Olympus), MetaMorph (Molecular Devices), Velocity (PerkinElmer), Huygens (SVI), Arivis (see http://vision<dot>arivis<dot>com/en/arivis-Vision4D) (see Dominguez, E. et al. Non-invasive in vivo measurement of cardiac output in C57BL/6 mice using high frequency transthoracic ultrasound: evaluation of gender and body weight effects. *Int. J. Cardiovasc. Imaging* 30, 1237-1244 (2014)), or using free or open-source tools such as Fiji 3D Viewer (see Schmid, B., Schindelin, J., Cardona, A., Longair, M. & Heisenberg, M. A high-level 3D visualization API for Java and ImageJ. *BMC Bioinformatics* 11, 274 (2010)), Vaa3D (see Peng, H., Bria, A., Zhou, Z., Iannello, G. & Long, F. Extensible visualization and analysis for multidimensional images using Vaa3D. *Nat. Protoc.* 9, 193-208 (2014)), Icy (see de Chaumont, F. et al. Icy: an open bioimage informatics platform for extended reproducible research. *Nat. Methods* 9, 690-696 (2012)), BioImageXD (see Kankaanpaa, P. et al. BioImageXD: an open, general-purpose and high-throughput image-processing platform. *Nat. Methods* 9, 683-689 (2012)), VolView (Kitware, see http://www<dot>kitware<dot>com/opensource/volview<dot>html), or Bioview3D (see Kvilekval, K., Fedorov, D., Obara, B., Singh, A. & Manjunath, B. S. Bisque: a platform for bioimage analysis and management. *Bioinformatics* 26, 544-552 (2010)). These tools all support 3D volumetric rendering of image data that can be interactively rotated and zoomed by the user, as well as functionality for selecting sub-volumes, virtual 2D sectioning, image contrast and other color-map adjustments and manual annotation.

Stitching very large acquisition volumes can easily produce image files that are too slow to load and display directly on machines with limited memory. Table 3 indicates which software tools support "out of core" visualization, utilizing read on demand, caching and multi-resolution representations to process and visualize datasets that are too large to fit in memory while preserving interactivity. In particular, TeraFly (see Bria, A. & Iannello, G. TeraStitcher—a tool for fast automatic 3D-stitching of teravoxel-sized microscopy images. *BMC Bioinformatics* 13, 316 (2012)), Imaris (BitPlane) (see Ascoli, G. A., Donohue, D. E. & Halavi, M. NeuroMorpho.Org: A central resource for neuronal morphologies. *J. Neurosci.* 27, 9247-9251 (2007)), and BigDataViewer (see Benmansour, F. & Cohen, L. D. Tubular Structure Segmentation Based on Minimal Path Method and Anisotropic Enhancement. *Int. J. Comput. Vis.* 92, 192-210 (2011)) (Fiji, see http://fiji<dot>sc/BigDataViewer) use custom multi-resolution, tiled file formats for storing image data on disk. This aids interactive visualization (even on machines with significant RAM) since low-resolution views can be displayed quickly with higher-resolution detail filled in as soon as it can be read from disk.

Morphometric Analysis

Tracing of neurites can be carried out using plugins provided in general processing tools: e.g. Imaris Filament Tracer (BitPlane) (see Myatt, D. R., Hadlington, T., Ascoli, G. A. & Nasuto, S. J. Neuromantic—from semi-manual to semi-automatic reconstruction of neuron morphology. *Front. Neuroinform.* 6, 4 (2012)), Amira Skeletonization Plugin (FEI) (see Gleeson, P. et al. NeuroML: a language for describing data driven models of neurons and networks with a high degree of biological detail. *PLoS Comput. Biol.* 6, DOI: 10.1371/journal.pcbi.1000815 (2010)), Metamorph NX Neurite Tracing (Molecular Devices) (see Parekh, R. & Ascoli, G. A. Neuronal morphology goes digital: a research hub for cellular and system neuroscience. *Neuron* 77, 1017-1038 (2013)), Fiji Simple Neurite Tracer (see Longair, M. H., Baker, D. A. & Armstrong, J. D. Simple Neurite Tracer: open source software for reconstruction, visualization and analysis of neuronal processes. *Bioinformatics* 27, 2453-2454 (2011); and Benmansour, F. & Cohen, L. D. Tubular Structure Segmentation Based on Minimal Path Method and Anisotropic Enhancement. *Int. J. Comput. Vis.* 92, 192-210 (2011)), Vaa3D-Neuron2 (see Peng, H. et al. Virtual finger boosts three-dimensional imaging and microsurgery as well as terabyte volume image visualization and analysis. *Nat. Commun.* 5, 4342 (2014)); or via special purpose software: e.g. Neurolucida (see Glaser, J. R. & Glaser, E. M. Neuron imaging with Neurolucida—a PC-based system for image combining microscopy. *Comput. Med. Imaging Graph.* 14, 307-317 (1990)), neuTube (see Feng, L., Zhao, T. & Kim, J. neuTube 1.0: a New Design for Efficient Neuron Reconstruction Software Based on the SWC Format. eneuro, DOI: 10.1523/ENEURO.0049-1514.2014 (2015)), Neural Circuit Tracer (see Chothani, P., Mehta, V. & Stepanyants, A. Automated tracing of neurites from light microscopy stacks of images. *Neuroinformatics* 9, 263-278 (2011)), flNeuron-Tool (see Ming, X. et al. Rapid reconstruction of 3D neuronal morphology from light microscopy images with augmented rayburst sampling. *PLoS One* 8, DOI: 10.1371/journal.pone.0084557 (2013)), Farsight trace editor (see Luisi, J., Narayanaswamy, A., Galbreath, Z. & Roysam, B. The FARSIGHT trace editor: an open source tool for 3-D inspection and efficient pattern analysis aided editing of automated neuronal reconstructions. *Neuroinformatics* 9, 305-315 (2011)), Neuron Studio (see Luisi, J., Narayanaswamy, A., Galbreath, Z. & Roysam, B. The FARSIGHT trace editor: an open source tool for 3-D inspection and efficient pattern analysis aided editing of automated neuronal reconstructions. *Neuroinformatics* 9, 305-315 (2011)), Neuromantic (see Myatt, D. R., Hadlington, T., Ascoli, G. A. & Nasuto, S. J. Neuromantic—from semi-manual to semi-automatic reconstruction of neuron morphology. *Front. Neuroinform.* 6, 4 (2012)). Several of these tools provide automated or semi-automated workflows that allow a user to trace neurites by clicking on a few points along a given neurite which can greatly accelerate initial tracing of long-range projections. The 3D Image Analysis workflow below gives estimates of time required to produce a rough-draft trace for a test image. For reference, estimated processing times are given based on tests with a large tiled image, 144 fields of view taken on an LSM 780 at 5× magnification, stitched in ZEN (Zeiss) (see Glaser, J. R. & Glaser, E. M. Neuron imaging with Neurolucida—a PC-based system for image combining microscopy. *Comput. Med. Imaging Graph.* 14, 307-317 (1990)) to produce a single channel, 8-bit, 30 GB image stack of size $3.3 \times 10^{10}$ voxels (16384×9216×220) covering approximately 1.165 $mm^3$ (2.72×1.53×0.28 mm) of tissue. Semi-automated tracing tools are computationally intensive and currently have slow performance on volumes larger than a few gigabytes. Efficient use of these tools thus requires manual selection or cropping of regions-of-interest during annotation and the resulting traces merged in a post-processing step.

Morphology of traced neurites can be saved in SWC (standard file format developed by the Southampton Neurosciences Group; see SWC file format specifications on the Computational Neurobiology and Imaging Center of the Mount Sinai School of Medicine website: http:// research<dot>mssm<dot>edu/cnic/swc<dot>html), NeuroML (see Gleeson, P. et al. NeuroML: a language for describing data driven models of neurons and networks with a high degree of biological detail. *PLoS Comput. Biol.* 6, DOI: 10.1371/journal.pcbi.1000815 (2010)), or NEURON .hoc file formats which in turn can be used with a wide range of downstream neuroinformatic tools (see Parekh, R. & Ascoli, G. A. Neuronal morphology goes digital: a research hub for cellular and system neuroscience. *Neuron* 77, 1017-1038 (2013); and Meijering, E. Neuron tracing in perspective. *Cytometry A.* 77, 693-704 (2010)) including statistical morphometry (see Scorcioni, R., Polavaram, S. & Ascoli, G. A. L-Measure: a web-accessible tool for the analysis, comparison and search of digital reconstructions of neuronal morphologies. *Nat. Protoc.* 3, 866-876 (2008)), assembly and simulation of biophysical models (see Gleeson, P., Steuber, V. & Silver, R. A. neuroConstruct: A tool for modeling networks of neurons in 3D space. *Neuron* 54, 219-235 (2007)) and deposition in online searchable databases (e.g. http://www<dot>neuromorpho<dot>org/).

Applications of the Methods

PACT, PARS, and RIMS clear a variety of tissues, from laboratory mice and rats (organs and adult whole-bodies) to human primates (FIG. 1F-G, tumor biopsy) and are compatible with endogenous-fluorescence, immunohistochemistry, long-term sample storage, smFISH, and microscopy with cellular and subcellular resolution. Furthermore, the potential exists to apply PARS to the clearing and staining of large, isolated whole-organs when the vasculature is preserved during organ excision. Akin to paraffin embedding, the increased rigidity of hydrogel-embedded, uncleared samples can allow unstructured soft tissues (e.g. pancreas, thymus) and amorphous biological samples (e.g. sputum) to be stabilized for manual sectioning as well as for automated slicing and imaging systems, such as serial two-photon tomography. When these tissue-hydrogel hybrids are PACT- or PARS-cleared rather than thin-sectioned for imaging, whole organs and thick tissue blocks become amenable to visualization with modern microscopy methods such as light sheet fluorescence microscopy (LSFM, which rapidly scans large sample volumes, thereby minimizing photobleaching but maximizing the phenotypic content within the image stack) and super-resolution microscopy. Bridging these microscale and nanoscale imaging modalities, the recent method of expansion microscopy (ExM) recruits a byproduct of CLARITY and PACT hydrogel-embedding, namely the capacity to absorb water, to great advantage. By deliberately swelling tissue-hydrogel hybrids, isotropically expanded tissues can be mined for qualitative information of subcellular structures at synaptic resolution using only a conventional confocal microscope.

Accelerating Biomedical Discovery with Tissue Clearing

The current and potential biomedical applications of PARS and PACT are summarized in Table 1. PARS and PACT enable detailed structural information from peripheral tissue and organ samples to be obtained, aiding in the study of distinct cellular populations/environments within their unsevered tissue milieu. For example, stem cell niches that are embedded within relevant tissue environments can be studied, such as the intestinal stem cells located in small intestinal crypts and within the bone marrow niche. Tumor architecture and morphology can be mapped, including tumor margins, tumor vascularization, cellular heterogeneity, and metastatic foci across the entire organism, for both research and diagnostic purposes. Whole-body optical clearing by PARS and imaging could facilitate obtaining better peripheral nerve maps which can then facilitate understanding of the neural processing that accompanies peripheral nerve/organ function and dysfunction.

Importantly, PARS may also facilitate whole-body screening of therapeutics for off-target and on-target binding, and for imaging the biodistribution of administered agents as a method for the qualitative determination of their pharmacokinetic-pharmacodynamic (PK/PD) properties. Similarly, PARS can be employed to expedite the slow, labor-intensive process of screening novel viral vector variants for specific tropism characteristics. Typically researchers perform conventional tissue slicing and histology on numerous tissues across multiple samples, an exceedingly laborious process. Whole-body screening through PARS can improve throughput and reduce the risk of sampling errors.

The described protocols for tissue stabilization and lipid removal allow for rapid phenotyping of whole-organs and whole-organisms and therefore could advance biomedical research with respect to the study of changing tissue pathology during aging or during disease progression. One obstacle to studying the progression of cell death that occurs during neurodegeneration (e.g. in Parkinson's, Alzheimer's, epilepsy, stroke) is the inability to visualize cells that have already died and have been removed by macrophages before the tissue was dissected for histological analysis. A similar cellular mapping confound exists in ablation experiments, wherein toxins are used to damage cells for studies that aim to causally link the function of a defined neuronal population (compact or sparsely distributed) to brain activity and behavior. The post-quantification is rarely accurate since it relies on inferring the exact distribution of ablated cells based on their representative distribution in placebo treated brains. By combining PARS with TEMPEST—a precursor to CLARITY—the in vivo expression of long-lasting keratin filaments (that outlive the cells themselves while keeping a loyal blueprint of the morphology) within populations of interest can facilitate accurate post-mortem quantification and brain-wide mapping of long-degenerated cells.

Size Fluctuations in Tissue-Hydrogel Hybrids: Challenge and Opportunities

Most protocols that render tissues transparent cause notable sample volume fluctuations. In general, clearing protocols that entail dehydration steps for clearing with organic solvents or some concentrated refractive index-matching solutions cause tissue shrinkage, whereas protocols that involve prolonged incubations in aqueous detergent-based solutions tend to cause gradual tissue expansion (Table 2). In part a consequence of the water-absorbing properties of polyacrylamide, a nitrogen-containing derivative of the super-absorber polyacrylic acid, tissue-hydrogel expansion has previously been reported with CLARITY and PACT processing (FIG. 3B-C), and indeed, has been used to great advantage in ExM. Several factors have been shown to influence the swelling properties of water-absorbing hydrogels. Most notable are pH, the dissolved ion content of the aqueous swelling media (i.e., clearing buffer), and the tissue-hydrogel microstructure, including the ordering of monomeric units within a polymerized hydrogel, the degree of crosslinking, and the mechanical rigidity of the embedded tissue. With respect to tissue clearing, as detergent gradually solubilizes and extracts tissue biomacromolecules, not only can water migrate into this additional space in the tissue-hydrogel matrix, but also there is less mechanical resistance from tissue components to polymer swelling as water continues to diffuse in.

For neuron tracing and brain mapping purposes (i.e., connectomics), expansion-contraction cycles should be minimized so as not to sever fine processes, distort the spatial arrangement of cells within local niches, or alter cellular connectivity. Similarly, gross size changes, particularly when anisotropic, complicate image registration with existing atlases such as the Allen Brain Atlas. A few modifications to passive CLARITY-based protocols have been previously proposed in order to counteract tissue expansion that occurs during clearing and to minimize the occurrence of morphological artifacts that could be introduced with fluctuating tissue size. They include: using in-skull clearing protocols (e.g. PARS-CSF and PARS, see FIG. 6-7, FIG. 14); extending the post-fixation step for perfused, excised organs, including the brain, prior to the start of any clearing protocol; and/or performing PACT with a hydrogel monomer formulation that contains increasing amounts of PFA (e.g. A4P1-4). With respect to the latter, the inclusion of PFA in hydrogel monomer compositions not only combats hydrogel swelling, but also, the expansion becomes increasingly isotropic (FIG. 3B). Thus, for improved tissue preservation it is advisable to supplement the A4P0 hydrogel recipe with PFA (1-4% PFA in the monomer solution).

The inclusion of PFA in monomer solutions also curtails tissue size changes in mounting media. Upon their initial immersion in RIMS, tissue samples contract during the first hour (~20% for A4P0-embedded coronal rodent brain sections), followed by a gradual rebound back to their pre-RIMS size. Imaging during this time window should be avoided as these slight size fluctuations could introduce apparent tissue deformities or sample drift issues during image acquisition. With adequate equilibration in RIMS (e.g. hours to days, depending on sample size, tissue permeability, etc.), sample size and transparency will reach a steady-state for high-resolution, deep imaging.

It follows that a motivating factor behind the development of PARS was to neutralize this potential risk of tissue expansion during clearing. Although the tissue becomes more permissive to hydrogel swelling as lipid membranes are permeabilized and extracted, the skin encasing, bone structure, and connective tissue will continue to restrict water absorption by the hydrogel and thus minimize size changes of the internal organs. Consequently, the addition of PFA to the PARS monomer solution is not necessary.

However, swelling—if isotropic, can be advantageous. By expanding hydrogel-embedded tissue uniformly, dense cell populations can be distributed spatially for cell counting or for analyzing local cell contacts (FIG. 13, Supplementary Methods); likewise, dense cell and/or fiber tracts, such as the corpus callosum, the spinal cord, and individual muscles may be expanded for easier anatomical study. Through altering the monomer components and concentration, scientists may quickly adjust the overall volume occupied by the hydrogel-embedded tissues, shrinking tissues to fit within the working distance of an objective, or swelling tissues for facile high-resolution imaging of diffraction-limited spots (see Dodt, H. U. Microscopy. The superresolved brain. *Science* 347, 474-475 (2015)).

Additional Considerations of the Method

As discussed in the previous section, some tissue deformation is expected with all tissue clearing protocols (see examples in Table 2), wherein the tendency for tissue to expand and/or shrink moderately during sample clearing and/or mounting is frequently noted. Whether these volume changes cause structural damage that would confound the interpretation of sample images is widely debated. Although some tissue swelling has been observed during PACT and PARS clearing, tissues subsequently contract to approximately their original size in RIMS media. Although difficult to test exhaustively by individual efforts, the net impact of these changes on overall cellular architecture appears to be minimal, as demonstrated by the preservation of fine cellular morphology, including that of fragile dendritic processes, across a range of tissue types. However, such changes in tissue volume do potentially complicate the process of image registration. To compare an image stack of an experimental sample to a representative dataset or to a reference atlas, it will be necessary to use structural landmarks or tissue stains rather than the sample size to align images. Validated tissue stains that can help with registration include: nissl or Golgi stain for the brain; membrane and organelle stains such as H&E stain for dual hematoxylin-based nucleic acid staining and eosin-labeling of red blood cells, cytoplasmic material, cell membranes, and extracellular structures and protein; fuchsin to stain collagen, smooth muscle, or mitochondria.

To image whole organs or thick tissue sections, the image data file sizes will be tera-scale; thus, it is important to employ a computational workstation with substantial RAM (this will be highly dependent on the individual software requirements, user-specific variables such as the average file size and the desired image analysis capabilities. Our experience showed that as much as 64-256 GB might be needed, depending on data and analysis type), multi-core CPUs and an excellent graphics card (e.g. Windows platform: AMD Radeon R9 290X 4.0 GB; MAC platform: AMD FirePro D700 6 GB).

Materials

Reagents

Sample to be imaged. This protocol describes imaging of brain and body samples prepared from wild-type mice (C57BL/6N and FVB/N, both males and females), Thy1-YFP mice (line H), and TH-cre rats.

1. Euthasol (Virbac, cat. no. 710101)

Perfusion Solutions

1. Paraformaldehyde (PFA, 16% and/or 32% PFA in aqueous solution (wt/vol) Electron Microscopy Sciences, cat. no. 15710-S)
2. 1× Phosphate-buffered saline (1×PBS)
3. Sodium nitrite (Sigma-Aldrich, cat. no. 237213-500G). As a vasodilator, 0.5% sodium nitrite is added to the heparinized saline perfusion buffer to facilitate thorough blood removal from vasculature and perfusion ease. Alternatively, nitroglycerin may be substituted for sodium nitrite.
4. Heparin sodium salt from porcine intestinal mucosa (Sigma-Aldrich, cat. no. H3149)

Hydrogel Monomer (HM) Solution

1. Acrylamide solution (40% wt/vol; Bio-Rad, cat. no. 161-0140)
2. Bis-acrylamide (2% wt/vol; Bio-Rad, cat. no. 161-0142)
3. Polymerization thermal initiator VA044: 2,2'-Azobis[2-(2-imidazolin-2-yl)propane]dihydrochloride (Wako, cat. no. VA-044)
4. 10×PBS Clearing Solutions 1. Boric acid (Sigma-Aldrich, cat. no. B7901 or B6768)
2. Sodium hydroxide pellets (EMD, cat. no. SX0590-3)
3. Sodium dodecyl sulfate (Sigma-Aldrich, cat. no. L3771) or 20% SDS solution in water (Sigma-Aldrich, cat. no. 05030)
4. 10×PBS "homemade" PBS or PBS from a variety of suppliers has been used with success.
5. 0.5 M EDTA solution (Lonza AccuGENE, cat. no. 51234; or Sigma-Aldrich, cat. no. 03690)

Refractive Index Matching Solution (RIMS)
1. Histodenz™ (Sigma-Aldrich, cat. no. D2158)
2. 0.02 M Phosphate buffer
3. Sodium azide (Fisher Scientific, cat. no. 71448-16) To prevent microbial growth, sodium azide should be added to all mounting medias (RIMS and sRIMS), as well as to all immunostaining dilutions and wash buffers that are used in extended incubations.

Sorbitol-Based Refractive Index Matching Solution (sRIMS)
1. 70% Sorbitol (Sigma-Aldrich, cat. no. 309532)
2. 0.02 M Phosphate buffer
3. Sodium azide (Fisher Scientific, cat. no. 71448-16)

Refractive Index Matching Solution for Cold Storage (cRIMS)
1. Histodenz™ (Sigma-Aldrich, cat. no. D2158)
2. 0.005 M Phosphate buffer
3. Sodium azide (Fisher Scientific, cat. no. 71448-16)

Immersion Media and Alternative Mounting Media
There are numerous commercial and home-made RIMS alternatives, including FocusClear, Cargille Labs optical liquids, 2,2'-thiodiethanol, and diluted glycerol. A glycerol-based mounting media recipe is described here.
1. Glycerol (87%, vol/vol): Prepare 80-90% (vol/vol) glycerol (Sigma-Aldrich, cat. no. G5516) in $dH_2O$.

Immunostaining Reagents
1. 1×PBS with Triton X-100 (0.1%, vol/vol)
2. Primary and secondary antibodies (see Table 4 for examples of antibodies used in this and related work)
3. Normal donkey serum (NDS, Jackson ImmunoResearch Laboratories, cat. no. 017-000-121)
4. Agarose, low melt temperature (Research Products International Corp., cat. no. 9012-36-6)

FISH Reagents (Optional, see Supplementary Methods)
1. 10×PBS pH 7.4, RNase-free (Life Technologies, cat. no. AM9625)
2. Ethanol, absolute (J.T. Baker, cat. no. 8025)
3. RNase free sterile $H_2O$ (Life Technologies, cat. no. 10977-015)
4. 10% dextran sulfate (wt/vol, Sigma-Aldrich, cat. no. D8906)
5. Formamide, deionized, nuclease-free (EMD Millipore, cat. no. 344206; or Life Technologies, cat. no. AM9342)
6. 20× Saline sodium citrate buffer (SSC), RNase-free (Life Technologies, cat. no. AM9763)
7. Slowfade Gold+DAPI (Life Technologies, cat. no. S-36938)
8. Aminosilane-treated coverslips ((3-Aminopropyl) triethoxysilane, Sigma-Aldrich, cat. no. 440140)
9. Sodium borohydride (Sigma-Aldrich, cat. no. 213462; or Santa Cruz biotechnology, cat. no. CAS 16940-66-2)

Equipment
Hydrogel Polymerization
1. House vacuum line or vacuum pump
2. Nitrogen gas supply (any)
3. PTFE tubing (McMaster-Carr) and/or Masterflex L/S 14 tubing (Cole Palmer), for connection to vacuum line and inert gas supply PACT Equipment
1. Sample vials, either commercially available vacutainers (10 ml Vacutainer serum blood collection tubes, BD, cat. no. 366430) or 50 ml conical tubes with commercially available rubber stoppers for hydrogel embedding step
2. Commercially available stoppers for 50 ml conical tubes: Folding Skirt Rubber Stopper 30.7 mm diameter (Cole-Parmer, cat. no. EW-62995-87) or Saint Gobain Folding Skirts Rubber Stoppers 31.4 mm diameter (Spectrum Chemical Mfg. Corp, cat. no. 142-55179) or Twistit™ Rubber stopper size 6 (Fisher Scientific, cat. no. 14-131D; Sigma-Aldrich, cat. no. Z164364; eBay, various)
3. Air-Tite Vet premium hypodermic needles, 22 G×4", (Air-Tite Products Co., Lot: 14-11563, SKU N224)
4. 1-1.5" needles for venting sample containers during hydrogel embedding (16-22 G)
5. 3-5 ml syringes (BD syringes)

PARS Equipment
1. Masterflex Tygon E-Lab tubing (Cole Palmer, cat. no. EW-06460-48), or Tygon S3™ Laboratory Tubing E-3603 (VWR, 0.125" ID: cat. no. 89403-854, 0.09375" ID: 89404-000
2. 3-way stopcock with Luer lock (World Precision Instruments, cat. no. 14035-10)
3. Luer-to-tubing coupler kit (World Precision Instruments, cat. no. 500895)
4. Barbed fitting assortment kit (World Precision Instruments, ca. no. 500890)
5. 22 G×1" gavage needle (any, e.g. 22 G 1.25 mm tip diameter straight feeding needle; Fine Science Tools, cat. no 18061-22; Braintree Scientific Inc., cat. no. N-PK 002)
6. Pipette tip boxes; we use empty 1000 µl racked filter tip boxes (USA Scientific)
7. Optional: 20 G blunt needle (BD, cat. no. 305183) and tubing (PlasticsOne) for PARS-CSF[18]
8. C & B Metabond (Parkell Inc., cat. no. 5380)
9. Tape (any)
10. Modeling clay (any, e.g. Sargent Art Inc, cat. no. 22-4400)
11. Peristaltic pump or circulator (any, e.g. Cole Palmer Masterflex L/S, cat. no. 77800-60; or Cole Palmer Masterflex L/S Easy Load II head and pump drive, cat. nos. 77200-62 and 7557-12)
12. 1 gallon freezer bags (Ziploc, or equivalent reusable and re-sealable airtight freezer bags made of durable plastic with a zipper closure).

General Equipment and Supplies
1. Silicon aquarium sealant (any, e.g. 3M™ Marine Grade Silicone Sealant Clear, PN08019)
2. Platform shaker (VWR, Rocking Platform model 200) and/or nutating mixer (VWT, cat. no. 82007-202)
3. Bath incubator (Fisher Scientific, Isotemp model 2223) or 37° C. warm room
4. Shaking Water Bath (Thermo Forma, cat. no. 003-8830)
5. Razor blades and/or scissors (any)
6. mColorpHast™ pH Test Strips (EMD Millipore, cat. no. 1.09543.0001, 1.09584.0001)

Sample Mounting and Imaging for Confocal Microscopy
1. 7.0 mm or 3.0 mm spacers (iSpacer, SunJin Lab Co.), or 0.5 mm or 2.5 mm spacers (Silicone Isolator, Electron Microscopy Sciences; or GRACE Bio-Labs), or silicone rubber sheet (any)
2. Putty (any, e.g. Bostik Blu-Tack adhesive putty)
3. Clear nail polish or Entellan (Electron Microscopy Sciences, cat. no. 14800)
4. Microscope slides (Thermo Scientific, cat. no. 10143352; VWR, cat. no. 48382-173; Brain Research Laboratories, cat. no. 5075-plus)
5. Cover slips (VWR, cat. no. 48404-452, 16004-344, 16004-322; Brain Research Laboratories, cat. no. 4860-1-½)
6. Vacuum grease (Sigma-Aldrich, cat. no. Z273554)
7. Optional: Refractometer (Reichert AR200 Digital Hand-held Refractometer, cat. no. 13950000)
8. Confocal or light sheet microscope—any as available; data here were obtained with a Zeiss LSM 780 single-photon microscope or a custom made light sheet fluorescent microscope (LSFM) system (see supplies listed in Table 7)
9. Microscope objectives for thick-section imaging, such as the CLARITY-optimized objectives now produced by major microscopy companies, including Leica and Olympus. Images presented here were obtained using the following Zeiss objectives: Fluar 5×/0.25 M27 objective (working distance 12.5 mm), Plan-Apochromat 10×/0.45 M27 objective (working distance 2.0 mm), LD SC Plan-Apochromat 20×/1.0 Corr M32 85 mm scale-immersion objective (working distance 5.6 mm), LD LCI Plan-Apochromat 25×/0.8 Imm Corr DIC M27 multi-immersion objective (working distance 0.57 mm), and Olympus 25×1.0 N.A. multi-immersion objective (working distance 8.0 mm)
10. Image handling software, such as Imaris (Bitplane) (see Uygun, B. E. et al. Decellularization and Recellularization of Whole Livers. *J. Vis. Exp.*, e2394 (2011))

Reagent Setup 0.1M Phosphate Buffer (PB)

Add 3.1 g $NaH_2PO_4$ (monohydrate) and 10.9 g $Na_2HPO_4$ (anhydrous) in $dH_2O$ to a total volume of 1 L at pH 7.4; sterile filter and store at room temperature (18-25° C., RT) or 4° C. for up to several months. For RIMS, dilute five-fold to 0.02 M phosphate buffer, and adjust the final RIMS pH to 7.5.

0.01 M Phosphate-Buffered Saline (1×PBS)

Combine 8 g NaCl, 0.2 g KCl, 1.42 g $Na_2HPO_4$, 0.245 g $KH_2PO_4$ in distilled $H_2O$ ($dH_2O$) to a total volume of 1 L; pH to 7.4, sterile filter or autoclave, and store at RT or 4° C. for up to several months. Alternatively, purchase 1×PBS mix (Sigma Aldrich, cat. no. P5368) or pre-made solution (Lonza, cat. no. 04-409R) from a commercial supplier; adjust the final pH when necessary. Use 1×PBS at pH 7.4 unless otherwise noted (e.g. in clearing buffers).

10×PBS Stock

For 10 L of the 10× stock, dissolve 800 g NaCl, 20 g KCl, 144 g $Na_2HPO_4$ dihydrate, 24 g $KH_2PO_4$ in 8 L of distilled water. Add additional water to a total volume of 10 L; sterile filter or autoclave. Upon dilution to 1×PBS, the pH should approach 7.4. The pH may be adjusted with hydrochloric acid or sodium hydroxide, as needed. The resultant 1×PBS should have a final concentration of 10 mM $PO_4^{3-}$, 137 mM NaCl, and 2.7 mM KCl. Alternatively, purchase 10× PBS pre-made solution (any, such as Lonza, cat. no. 17-517Q) from a commercial supplier.

Heparinized PBS (hPBS)

For flushing vasculature of blood at the start of perfusion, prepare 1×PBS with 0.5% sodium nitrite (wt/vol) and 10 units/ml heparin, pH 7.4. Place on ice until use or refrigerate up to a few weeks.

4% PFA (for Perfusion-Fixation)

To prepare 40 ml of 4% PFA (vol/vol), combine 4 ml of 10×PBS, 5 ml of 32% PFA solution and 31 ml ice-cold water. Adjust the pH to 7.4 and keep on-ice or refrigerate until use (same day).

1×PBS Containing 0.1% Triton X-100 (vol/vol) (PBST)

Add 1 ml Triton X-100 to 1×PBS for a total volume of 1 L, pH to 7.4. PBST may be stored at RT for a few months when sterile-filtered; vortex or stir on a stirplate for several minutes prior to use.

Boric Acid Buffer (BB)

Prepare a 1 M boric acid buffer stock solution through stirring 61.83 g boric acid and 10 g NaOH in 900 ml water with gentle heating. Once sodium hydroxide pellets and boric acid are fully dissolved, adjust the pH to 8.5 with NaOH and add water to a total volume of 1 L; store at RT for up to a few months. To prepare fresh borate-buffered clearing solutions, such as 8% SDS in 0.2 M BB at pH 8.5 (8% SDS-BB) for PACT and PARS, dilute 400 ml 20% SDS and 200 ml 1 M boric acid buffer stock to 1 L with distilled and deionized water (dd $H_2O$); adjust the pH to 8.5, if necessary. To make a boric acid wash buffer (BBT, 0.2 M boric acid buffer with 0.1% Triton X-100 (vol/vol), pH 8.5), dilute the 1 M boric acid stock to 0.2 M boric acid in dd $H_2O$, adding 1 ml of Triton X-100 per litre of BBT and stirring on a stirplate for 10 minutes. BBT may be stored at RT for several weeks, barring contamination; vortex or stir on a stirplate for several minutes prior to use.

PACT Monomer Solution

For rapid preparation of samples that are amenable to both standard immunohistochemistry and fluorescence imaging as well as smFISH, prepare an A4P0 hydrogel: 4% Acrylamide (0% PFA) in 1×PBS. For 200 ml of hydrogel monomer solution, add 20 ml of 40% (wt/vol) acrylamide and 20 ml of 10×PBS to 160 ml ice-cold $dH_2O$. Stir 500 mg thermoinitiator 2,2'-Azobis[2-(2-imidazolin-2-yl)propane] dihydrochloride into ice-cold monomer solution (0.25% wt/vol final concentration). Hydrogel monomer solutions must remain cold prior to use to prevent premature polymerization; we generally prepare solutions fresh on ice, but they may be stored short-term (several hours) at 4° C. or on ice, or long-term (several months) at −20° C., protected from light.

Various hydrogel monomer formulations have been tested, including combinations of 2% or 4% acrylamide with 0% or 4% PFA and/or 0.05%-0.25% bis-acrylamide. It was determined that A4P0 without bis-acrylamide granted rapid clearing and good antibody penetration during IHC without compromising the macromolecular content and cellular structure of tissue samples. In comparison to CLARITY, 4% PFA was eliminated from the hydrogel monomer solution, however, thorough PFA-mediated crosslinking of tissue proteins was ensured prior to hydrogel monomer incubation via 4% PFA transcardial perfusion and 4% PFA post-fixation steps.

To enlarge the hydrogel pores for faster sample clearing and immunolabeling, bis-acrylamide and PFA were excluded from the hydrogel recipe proposed in CLARITY. Although tissue proteins and overall tissue architecture was preserved during PACT and PARS processing, specific native and non-native biomolecules, (e.g. non-membrane associated proteins, cytoplasmic signaling molecules, commensal and pathogenic microorganisms) may be more sensitive to the clearing process. Herein, either or both of these hydrogel components may be re-introduced into the hydrogel formulation to increase crosslinking density and thus better stabilize sparse epitopes. However, any increase in the net concentrations of hydrogel monomers will result in slower diffusion of SDS micelles and of antibody-based labels during clearing and immunostaining, respectively.

A4P1, A4P2, A4P4 Monomer Solutions

To preserve a sensitive sample's structural integrity during clearing, prepare a hydrogel solution with the inclusion of 1%, 2%, or 4% PFA, respectively: 4% Acrylamide, (1%, 2%, or 4%) PFA in 1×PBS. For example, for 200 ml of A4P4 hydrogel monomer solution, add 20 ml of 40% (wt/vol) acrylamide, 25 ml of 32% PFA, and 20 ml of 10×PBS to 135 ml ice-cold $dH_2O$. Stir 500 mg thermoinitiator 2,2'-Azobis [2-(2-imidazolin-2-yl)propane]dihydrochloride into ice-cold monomer solution (0.25% wt/vol final concentration). Hydrogel monomer solutions must remain cold prior to use to prevent premature polymerization; we generally prepare solutions fresh on ice, but they may be stored short-term at 4° C. or long-term at −20° C., protected from light.

Detergent for Tissue Clearing

PACT and PARS tissue clearing is accomplished via exposing tissue to an 8% SDS detergent solution, or in special cases (PACT-deCAL, ePACT), to a 10% SDS detergent solution. All initial validation of PACT and PARS was performed using a range of SDS concentrations (4%-16% SDS), prepared in a range of buffers (1×PBS at pH 7.5, 1×PBS at pH 8.0 (for PACT-deCAL), 1×PBS at pH 8.5, and in 0.2 M sodium borate buffer at pH 8.5). Aside from a slight clearing rate enhancement at more alkaline pH's (i.e., 8% SDS-BB and 8% SDS-PBS at pH 8.5) there was no apparent trade-off in the quality or characteristics of cleared soft tissue. Thus PARS and PACT tissue clearing in 1×PBS at pH 7.5 (abbreviated 8% SDS-PBS (pH 7.5)) may hold added convenience for many users. It is suggested to periodically replace the clearing solution if it begins to acidify (i.e. monitor the clearing solution pH with pH indicator strips every 72 hours). It is worthwhile to note that sodium borate buffer possesses anti-microbial and anti-fungal characteristics that make it an ideal buffer for extended tissue incubations. When 1×PBS is used in place of sodium borate, an appropriate antimicrobial agent should be added to the buffer (e.g. a final concentration of 0.01% sodium azide in buffer solutions). We freshly prepare clearing solutions for each round of tissue clearing, with RT storage (up to several weeks) of excess clearing solution for buffer exchanges.

While a clearing solution of 8% SDS is proposed, users may wish to vary the SDS concentration according to their needs. As a starting point, lower SDS concentrations should be used for larger samples as this prevents the detergent-exposed outer layers from overclearing while the sample center remains opaque. Thinner tissue sections (e.g. 250 µm brain slices from electrophysiology) may be cleared rapidly with 10-15% SDS, however overclearing and loss of biomolecules are a greater risk.

Antibody Incubation Buffer (IHC Buffer)

The dilution of antibodies used in PACT and PARS will be highly dependent on, among other things, the quality of the antibody, the size and tissue type of the sample to be labeled, the cellular location and concentration (i.e., expression level) of the target biomolecule, etc. We recommend a starting dilution of ~1:200-400 and/or staining reagents in 1×PBS containing 2% normal donkey serum, 0.1% Triton X-100 and 0.01% (wt/vol) sodium azide, however the exact antibody concentrations will need to be validated on a case-by-case basis. Prepare IHC buffer fresh.

RIMS

For a mounting media with RI=1.47, which is used for all samples presented here unless otherwise noted, dissolve 40 g of Histodenz™ in 30 ml sterile-filtered 0.02 M phosphate buffer. This is most easily accomplished by adding Histodenz™, phosphate buffer, and a magnetic stir bar to the final storage container (e.g. a 125 ml glass jar with lid), sealing the container to minimize evaporation and contamination, and stirring the solution on a stir-plate for approximately 10 minutes, vigorously shaking the closed jar by hand a few times during the stirring process. Once all Histodenz™ has dissolved, add sodium azide to a total concentration of 0.01% and adjust the pH to 7.5 with NaOH. RIMS may be stored at RT for several months; discard if microbial contamination occurs. Do not autoclave any solutions containing sodium azide.

sRIMS

Prepare a 70% sorbitol (wt/vol) solution in 0.02 M phosphate buffer with 0.01% sodium azide (pH adjusted to 7.5 with NaOH); store sRIMS at RT for up to several months, barring microbial contamination. This sorbitol-based mounting media outperforms 80-90% glycerol as a refractive index matching solution for rodent brain samples. At a net cost of ~$0.2/ml, sRIMS offers the greatest cost advantage over commercially marketed RI matching solutions that we have tested, such as FocusClear[8], and without a sacrifice in performance.

cRIMS

Prepare a stock buffer solution of sterile-filtered 0.005 M phosphate buffer. For a mounting media with RI=1.47, dissolve 40 g of Histodenz™ in 30 ml of this stock buffer solution; this is most easily accomplished on a stir-plate (see instructions for RIMS). Once all Histodenz™ has dissolved, add sodium azide to 0.01% and adjust the pH to 7.5 with NaOH. cRIMS may be stored at 4° C. for several months, barring microbial contamination. Samples that require short-term storage at 4° C. may be mounted in cRIMS; whereas RIMS-mounted tissue will become cloudy/turbid if placed at 4° C., the lower salt concentration of cRIMS reduces the appearance of salt precipitate at colder temperatures. Do not autoclave any solutions containing sodium azide.

Equipment Setup

Degassing Container for Hydrogel Polymerization

Glass vacutainers work well for degassing and hydrogel-embedding small rodent organs and tissue samples. However, for rat whole-brains and larger tissue samples, a larger container is sometimes useful. One solution is to purchase rubber stoppers that are compatible with 50 ml conical tubes and replace the conical screw-cap with an air-tight rubber stopper during degassing and hydrogel polymerization steps (see FIG. 2).

PARS Chamber

To perfuse PARS reagents through vasculature in a contained environment, a PARS chamber was constructed using components that are readily found in most biological research laboratories (see FIG. 6). The necessary components of a PARS set-up are: 1) a feeding needle catheter to deliver PARS reagents to vasculature, 2) a perfusate catch-basin (pipette box) where recirculating PARS reagents may pool once they exit the vasculature, 3) Tygon tubing threaded through a peristaltic pump so that pooling reagents may be collected from the catch-basin and recirculated back into a subject's vasculature, 4) Luer-to-tubing couplers, and finally 5) a Ziploc bag to contain the entire PARS chamber set-up. To construct the PARS chamber, drill two ⅛" holes into the front and one ⅛" hole into the left side wall of an empty 1000 µl pipette tip box. The holes are drilled just below the tip wafer (in FIG. 6, the holes are ~2 cm below the top rim). Next, snap ⅛"×⅛" barbed connectors into each of the drilled holes. The outflow line will circulate solvents from the pipette box chamber to the 3-way stopcock. To join the outflow line to a 3-way stopcock, use a 10 cm piece of Tygon tubing and connect one end to the inner left side ⅛"×⅛" barbed connector and tape the other end to the inside bottom of the pipette tip box. Continue this line through a peristaltic pump by using a new piece of Tygon tubing and connect one end to the outer left-side ⅛"×⅛" barbed connector and thread the tubing through a peristaltic pump. Then join the free end to a 3-way stopcock with a 3/32" barbed male Luer with locking nut. The inflow line circulates solvents from the 3-way stopcock to the vasculature. To link the inflow line to the pipette tip box, use a piece of 15 cm Tygon tubing and connect one end to the outer right front ⅛"×⅛" barbed connector and the other end to the 3-way stopcock with a 3/32" barbed male Luer with locking nut. To finish the inflow line, connect a piece of 75 cm Tygon tubing to the inner right front ⅛"×⅛" barbed connector. Then coil the inflow line to the bottom of the pipette tip box. This will equilibrate inflowing solvent to the desired temperature before it enters the subject's vasculature. Tape the coiled tubing to the pipette tip box. To quickly circulate bubbles formed during the changing of solutions without disconnecting the inflow line and for use of bubbling nitrogen gas into the solution during the polymerization step, a line linking the outflow line back to the pipette tip box is connected by joining a piece of 15 cm Tygon tubing to the 3-way stopcock with a full thread ³⁄₃₂" barbed female Luer to the outer left front ⅛"×⅛" barbed connector. This line is continued inside the pipette tip box and taped to the bottom. To finish the chamber, thread the inflow line through the top-left corner of the tip wafer and connect it to a feeding tube with a ⅛" barbed male slip Luer. As a forewarning, SDS and salt precipitate will begin to accumulate within these narrow lines over time. It is important to flush the lines (e.g. with dd $H_2O$) between subjects, and to replace occluded lines with new Tygon tubing (e.g. after every few subjects).

During hydrogel polymerization, the chamber must be enclosed inside a Ziploc freezer bag. To do this, disconnect the outer Tygon tubing that connects to the barbed connectors of the pipette tip box and puncture three holes into the Ziploc bag to accommodate the ⅛"×⅛" barbed connectors. Reconnect the Tygon tubing to their original ⅛"×⅛" barbed connector. To connect a vacuum line to this bagged PARS box for withdrawing oxygen, tape a female Luer tee onto the lid of the pipette box and puncture one hole through the Ziploc. Finally, make the Ziploc airtight by placing clay around the punctured regions in the Ziploc.

As a final note, a 1000 μl tip box has a volume of approximately 750 ml. Thus, during hydrogel polymerization and during clearing, 200-300 ml solution may be placed in the pipet box for recirculation without risk of the pipet box overflowing, or solution splashing out during its transport. Likewise, to conserve reagents during PARS clearing and immunostaining of smaller samples, a 200 μl tip box may be used to construct the PARS chamber; only 100 ml reagent is necessary to fill such chamber ~⅓ full (see FIG. 6).

Light Sheet Microscope

The light sheet microscope we use was built based on the laser-scanning single-side illumination method (see Huisken, J. & Stainier, D. Y. R. Selective plane illumination microscopy techniques in developmental biology. *Development* 136, 1963-1975 (2009)). Key to the design are objectives that offer a long working distance of eight millimeters while maintaining numerical aperture (N.A.) of 1.0 (e.g. CLARITY objectives). The system described below provides a cost-effective and relatively easy-to-replicate alternative to COLM (see Tomer, R., Ye, L., Hsueh, B. & Deisseroth, K. Advanced CLARITY for rapid and high-resolution imaging of intact tissues. *Nat. Protoc.* 9, 1682-1697 (2014)), a recently introduced light sheet microscope for CLARITY. We used cost-effective optical components, especially when creating, shaping and projecting the illumination light sheet. The immersion chamber and sample holder are printed with a 3D printer. The list of components can be found in Table 7.

The microscope is built onto a 4×6 foot optical table (see FIG. 8B). The various lasers are combined using dichroic filters, to one beam which is then expanded using a Galilean telescope, and shaped with an iris to match the Galvanometer scanner mirror size (6 mm in diameter). The Galvanometer scanner, coupled with a f-theta lens, is then used to generate the scanning light sheet, which is projected to the sample holder using two achromatic doublet lenses. The resulting light sheet has a full-width-half-maximum of 5-7 μm, depending on the wavelength of illumination (473-632 nm).

The detection objective lens (25×, 1.0 N.A. CLARITY objective, Olympus) is inserted into the immersion chamber. To prevent medium leakage from the chamber, we sealed the gap between the chamber and the objective with an O-ring and a flexible latex film, where only the tip of the detection objective is immersed. This setting allows the objective to move uninterruptedly during data acquisition yet making a sealed connection. The immersion chamber is printed using a 3D printer (ABS plastic) and is filled with glycerol to prevent evaporation-induced aberrations in RIMS medium.

Adjacent to the detection objective, we use tube lenses with different focal lengths to change the magnification of the light sheet microscope and consequently, its field-of-view. Higher magnification is used to digitally sample the acquired images in lieu with the high NA of the detection lens. We typically use magnification values between 25×-55×, with the corresponding field-of-view of 0.28-0.06 $mm^2$. To acquire the images, a camera with a light sheet mode feature is used (Zyla 4.2 sCMOS, Andor), where the scanning light sheet and the camera pixel readout are synchronized to improve the signal to noise ratio (see Baumgart, E. & Kubitscheck, U. Scanned light sheet microscopy with confocal slit detection. *Opt. Express* 20, 21805-21814 (2012)).

In order to rapidly scan large volumes, the sample is constantly translated using a xyz-theta stage, while the light sheet remains stationary. The xyz-theta stage is mounted on heavy-duty stainless steel bars to prevent sample vibration during data acquisition. To connect the sample holder to the xyz-theta stage we first place the sample in a quartz cuvette filled with RIMS solution. The cuvette is then attached to a 3D printed cap that has a Luer lock female connector mounted on top, and laboratory parafilm is used to seal the connector-cuvette interface. The sample holder is then attached to a xyz-theta stage via the Luer lock male connector.

To automatically scan large volumes using the microscope, we wrote a MATLAB program, which runs Micromanager (see Edelstein, A. D. et al. Advanced methods of microscope control using Micro-Manager software. *J. Biol. Methods* 1, DOI: 10.14440/jbm.12014.14436 (2014)) and serial communication, both controlling and synchronizing the various mechanical components. This program finds the synchronization parameters to run the camera in a light sheet mode, performs autofocus for the detection objective, and optimizes the lateral position of the illumination light sheet. To this end, both the illumination lens and the detection objective are mounted on computer-controlled linear stages.

Computer for Visualization Workflow

Visualization workflows were performed for a sample single channel, 8-bit, 30 GB image on a 64 bit Windows 8 machine with Intel i7-3770 CPU and 16 GB of RAM.

Procedure

Tissue Preparation for PACT and PARS

1. Prepare the perfusion and hydrogel monomer solutions, including 1×PBS containing 0.5% $NaNO_2$ (optional, for vasodilation) and 10 U/ml heparin (optional, for anti-coagulation) (hPBS), 4% PFA in 1×PBS, and the A4P0 hydrogel solution. 4% PFA should be prepared fresh. A4P0 may be prepared fresh or stored at −20° C. until use. For the latter, thaw A4P0 on ice prior to use. Perfusion solutions should be ice-cold. Discard PFA and hydrogel stock solutions if precipitate is observed.
2. Anesthetize the animal with an intraperitoneal (ip) injection of Euthasol (100 mg/kg of body mass for mice and rats), or according to institutional guidelines for rodent euthanasia (e.g. carbon dioxide inhalation until loss of consciousness, injection of pentobarbital or like solution).
3. Transcardially perfuse the subject with ice-cold hPBS until the perfusate drains clear from the right atrium (~20 ml at 10 ml/min for mice, ~100 ml at 50 ml/min for rats). The perfusion pressure (flow rate) during transcardial perfusion and during PARS (unless otherwise noted) should approximate the physiological pressure of the subject's circulatory system; at night, mice and rats have systolic and diastolic pressures (mm Hg) of approximately 125/90 (mouse) and 121/84 (rat), respectively. When using a peristaltic pump or alternative pressurized system, we suggest a rate of 10 ml/min for mice and ~100 ml/min for rats given that their cardiac output is reported to be ~10-35 ml/min (mouse) and ~50-120 ml/min (rat), respectively, depending on sex, strain, age, etc. If perfusate is observed to leak out of the subject's nostrils, the cerebral vasculature was likely compromised by too high a flow rate; it is not advisable to proceed with PARS-based clearing of this subject as PARS reagents may not reach all tissues; instead, organs of interest can be excised and cleared by PACT. Decrease the perfusion flow rate for all subsequent transcardial perfusions and PARS-based clearing steps. For the initial perfusion-fixation, gravity alone may be used to draw hPBS and PFA through rodent vasculature.
4. Troubleshooting: Without introducing air to the perfusion tubing, continue to perfuse the animal with ice-cold PFA (~50-70 ml at 10 ml/min for mice, ~100 ml at 50 ml/min for rats). While there are several alternative fixatives to 4% PFA, many of them carry consequences that are particularly detrimental to the hydrogel-embedding process and/or subsequent imaging of thick cleared samples. Mechanistically, formaldehyde augments the conjugation of tissue components to the acrylamide scaffold via its formation of methylene bridges between peptide amines and acrylamide, and so fixatives that lack this crosslinking ability will result in limited tissue-hydrogel hybridization. Although glutaraldehyde can penetrate and crosslink tissue more efficiently than formaldehyde, it also generates high autofluorescence that is more difficult to counteract in thicker tissues via standard aldehyde blocking measures.
5. For PACT-based clearing of excised tissue samples, including bones (PACT-deCAL variation), prepare tissue as described in option A. For PARS-based whole-body or whole-organ clearing using continuous perfusion through intact vasculature, proceed to option B. PARS-CSF allows within-skull clearing through the use of an indwelling guide cannula, which was previously inserted for neurobiological or pharmacological studies, or was positioned specifically for PARS-CSF based clearing. For PARS-CSF-based whole-brain or whole-spinal cord clearing using continuous perfusion through an intracranial cannula, proceed to option C. Following perfusion-fixation, all tissue samples that contain endogenous fluorophores must be protected from light. Minimize unnecessary light exposure during long incubations (>1 hour) by, for example, wrapping the sample containers in foil.

(A) Tissue Preparation for PACT
  (i) Carefully excise whole organs and tissues to be PACT processed
  (ii) If appropriate, slice whole organs into thick sections. Alternatively, pliable or fragile organs may be easier to thick-section, if required, immediately after hydrogel embedding, which greatly increases their firmness, before proceeding to clearing (step 7).
  (iii) Post-fix samples in 4% PFA for 1-2 hours at RT with gentle agitation on a rocking platform shaker.

The samples may be post-fixed overnight at 4° C. Fixing samples, especially smaller thinly-sectioned tissues, for longer periods of time may result in over-fixation and antigen masking.

(B) Tissue Preparation for PARS
  (i) Set-up the PARS chamber, tubing, and pump; pre-fill the PARS tubing with PFA so no air bubbles are introduced into tissue/vasculature. Fill the pipette box with PFA until ⅓ to ½ full.
  (ii) Transfer the perfused subject to the PARS chamber, laying the subject on top of the pipette wafer.
  (iii) PARS reagents will be delivered through the same feeding needle catheter used during transcardial perfusion. Thus, after transferring the rodent to the PARS chamber, check the placement of the feeding needle catheter. The catheter should enter the left ventricle. If it sits stably in the ventricle, leave as-is. Otherwise, advance the catheter through the left ventricle and into the aorta, just before the level of the aortic arch. Connect the PARS tubing to the feeding needle catheter. Take caution not to tear mouse vasculature.

Set the peristaltic pump to a flow rate of 1 ml/min and post-fix the subject for 1-2 hours at RT. As 4% PFA is pumped through the feeding needle, PFA perfusate should exit the right atrium and drain into the pipette box. This perfusate is then drawn up through tubing and recirculated through the subject. If necessary, add additional 4% PFA to the pipette box so that there is always enough PFA pooled in the pipette box to be recirculated through the tubing and subject vasculature. The amount of solution required for continuous recirculation will depend on the individual set-up (size of pipette box, liquid volume to fill tubing, evaporation from PARS chamber, species of subject, etc.). To prevent PFA from crosslinking acrylamide within vasculature during subsequent steps, perfuse 1×PBS for 45 minutes at RT.

(C) Tissue Preparation for PARS-CSF
  (i) If an indwelling guide cannula is not present, insert an intracranial brain shunt (e.g. 20 G blunt needle, BD) into the cisterna magna for spinal cord clearing, or lower the cannula through the skull (by drilling a hole in the region of interest and using tweezers to create an opening in the dura), to the level of the subarachnoid space, directly above the dorsal inferior colliculus, (see Yang, B. et al. Single-cell phenotyping within transparent intact tissue through whole-body clearing. *Cell* 158, 945-958 (2014)). Ensure that the cannula, whether newly inserted or existing, is firmly attached to the skull using dental acrylic (C&B-Metabond, Parkell Inc.) and free from blockages.
  (ii) Set-up the PARS chamber, tubing, and pump; pre-fill the PARS tubing with 4% acrylamide monomer solution (A4P0) so that no air bubbles are introduced into tissue/vasculature. Partially fill the pipette box with cold A4P0.
  (iii) Transcardially perfuse with 4% PFA, then briefly perfuse the subject with 1×PBS (≤30-60 ml for mice and rats, respectively) to wash away excess 4% PFA.

(iv) For whole-brain and whole-spinal cord clearing, ligate the arterial circulation, leaving the carotid arteries intact, and for rats or larger rodents, remove tissue not directly perfused by these vessels to conserve reagents. Transfer the subject to the PARS chamber, positioning tissue atop the pipette tip wafer. For whole-brain clearing alone, if desired, decapitate the subject and transfer only the head to the PARS chamber.

(v) Connect the PARS tubing to the cannula.

Formation of a Tissue-Hydrogel Matrix

The polymerization of tissue components with hydrogel monomers is crucial as it ensures that SDS micelles preferentially solubilize and remove tissue lipids during clearing. We previously demonstrated that a minimal acrylamide-based network, which supports more rapid clearing, was nevertheless sufficient for stabilizing proteins and nucleic acid. To increase the level of crosslinking without the addition of bis-acrylamide or PFA to the hydrogel monomer solution, the hydrogel-infused tissue should be carried through a rigorous degassing step.

6. Infuse sample with A4P0 via passive diffusion for PACT-based clearing (option A), or via continuous perfusion of A4P0 and then thermoinitiator for PARS and PARS-CSF (option B).

(A) Hydrogel-Embedding of PACT Samples (i) Transfer the PFA-fixed samples into a vacutainer or conical tube with rubber stopper; fill the container with ice-cold A4P0 hydrogel solution until the samples are fully submerged. Incubate the samples at 4° C. overnight. Samples may be incubated in A4P0 at 4° C. for 3 days. Once placed in monomer solution, the sample must remain at 2-8° C. Warmer temperatures may cause premature polymerization of hydrogel monomers before they have uniformly diffused throughout the tissue sample.

(ii) Purge the samples and sample container of residual oxygen. Insert one 4"-long hypodermic needle into the stopper so that the needle reaches near the bottom of the container, fully submerged in the hydrogel solution. Insert a second 1"-long needle into the stopper—this needle should not touch the hydrogel solution; its sole purpose is to vent excess gas from the container.

(iii) Connect the hypodermic needle to the nitrogen gas source (see FIG. 2B) and slowly turn on the flow of nitrogen. Allow the nitrogen gas to bubble through the hydrogel monomer solution for 1-10 minutes before turning off the flow of nitrogen and then removing both needles.

To form a more rigid tissue-hydrogel matrix, which imparts superior tissue crosslinking and only minor slowing of clearing and immunostaining steps, perform a more rigorous gas-exchange step. Place the sample container on ice and insert a 1"-long needle into the stopper. Connect the 1"-long needle to the house vacuum line and degas the sample for 5-10 minutes, depending on the sample size and volume of hydrogel. Gently tap or briefly vortex the sample-container every minute to dislodge air bubbles from tissue. Unhook the needle from the vacuum line, leaving the needle inserted in the stopper so that it may serve as a venting needle during nitrogen exchange. Remove the sample-container from ice, insert a 4"-long hypodermic needle that is connected to the nitrogen line into the stopper, and bubble nitrogen gas into the hydrogel monomer solution for 5-10 minutes. Turn off the flow of nitrogen. For larger tissue samples, such as whole rat organs, repeat the degassing process (degassing the sample on ice, and then bubbling nitrogen through the hydrogel solution). When finished, remove both needles and proceed to step (iv).

(iv) Place the sample container in a 37° C. waterbath for 2-3 hours.

With rigorous degassing, the A4P0 solution will form a hydrogel the consistency of honey or tacky silicon sealant that is somewhat difficult to remove from the tissue. With 1-minute nitrogen gas exchange, the A4P0 solution will form a hydrogel the consistency of syrup that may be poured off easily.

(v) Remove the excess hydrogel from the tissue sample. Exercise caution when removing tacky hydrogel from the tissue: cut away excess hydrogel with a scalpel or small surgical scissors and then use a Kimwipe to carefully remove excess hydrogel from tissue. Briefly rinse the samples in 1×PBS to wash away residual syrupy hydrogel from minimally degassed samples.

(vi) Hydrogel-embedded samples will have increased rigidity and structural integrity, and indeed this may be the primary goal for some users. In this case, it is possible to transfer hydrogel-embedded soft tissues (e.g. pancreas, spleen, thymus) and amorphous biological samples (e.g. sputum, mucus, organoid cell masses) that were prepared in steps 1-6 to other lines of experimental evaluation without proceeding with the PACT clearing protocol. All other users should proceed directly to step 7 for instructions on how to chemically clear PACT samples.

(B) Hydrogel-Embedding of PARS Samples (i) Circulate 4% acrylamide (A4P0) in 1×PBS through PARS tubing at RT overnight. Ensure that there is enough A4P0 pooled in the pipette tip box such that the tubing will not run dry during continuous recirculation.

(ii) Briefly perfuse the sample with 1×PBS to remove A4P0 and any residual PFA from the vasculature.

Use only enough 1×PBS to flush the vasculature of A4P0 (e.g. <5 ml for a mouse; 10 ml for a rat); do not infuse 1×PBS for so long that it displaces the A4P0 from tissue.

(iii) Without disconnecting the perfusion lines, place the PARS chamber into a Ziploc bag and place the bag under nitrogen atmosphere (i.e., fill the bag with nitrogen gas), deflate the bag, refill with nitrogen gas, seal the bag closed around the perfusion, and set aside for a few minutes while performing step iv.

(iv) Prepare 200 ml of 0.25% VA-044 initiator in 1×PBS; degas this solution via bubbling nitrogen gas through the solution for approximately 10 minutes. Add this solution to the pipette box within the Ziploc bag and place the bag-encased pipette box into a 37-42° C. water bath. If necessary, place a lead weight on top of the perfusion chamber to prevent it from tipping over. Turn on the pump so that the initiator circulates through the sample and PARS tubing and allow the sample to incubate for 2-3 hours in the water bath, replacing the solution with freshly "nitrogen-degassed" solution every hour. Alternatively, if the setup permits, the nitrogen gas can be bubbled directly into 200 ml of 0.25% VA-044 initiator in 1× PBS already loaded into the pipette box while slowly degassing the chamber as shown in FIG. 7I. This requires disassembly of the PARS chamber to make an airtight environment with the Ziploc.

Tissue Delipidation with SDS

The rate of tissue clearing depends on several parameters, including the inherent structural and biochemical properties of the tissue sample, the volume of the tissue sample, the hydrogel pore size and the density of tissue-hydrogel crosslinking, and the clearing set-up (SDS concentration, incubation temperature, pH of clearing buffer). It is important for users to determine the clearing parameters for their specific tissue samples empirically, using these guidelines as a starting point for further optimization. Likewise, because the rate of clearing may vary greatly, tissues embedded in minimal hydrogel monomer compositions, such as the A4P0 hydrogel suggested here, are more susceptible to deteriorating when samples are left unattended in SDS.

7. Clear tissue samples at 37-42° C. using either gentle agitation (PACT, option A; or PACT-deCAL, option B) or perfusion (PARS, option C), which accelerates micelle diffusion for rapid whole-body clearing. While 8% SDS is sufficient to solubilize lipids in soft tissue, 10% SDS and EDTA are required to clear and decalcify bone (PACT-deCAL, option B).

(A) PACT Clearing
   (i) Place each tissue-hydrogel sample into a 50 ml conical containing clearing buffer; gently rock the sample in a 37-42° C. shaking waterbath until tissue is optically transparent.
   (ii) If using thin organ slices (<1 mm) embedded in A4P0, check clearing progress every hour as they should clear in less than 12 hours. Likewise, porous tissue and samples with a high surface area to volume ratio or may clear in less than 24 hours. It is recommend that new users monitor the increasing transparency of such samples every 1-2 hours during initial test runs. Once a sample's time-to-clear is determined empirically by the user, stringent monitoring is no longer necessary. Dense, highly myelinated, or thick-sectioned (1-4 mm) tissue and whole organs should be checked daily during clearing and may require >96 hours.

Overclearing. For certain organs, and for brain tissue in particular, variations in cell density and myelination cause specific regions to clear at different rates. Thus, some regions will become transparent while the more slowly clearing regions will only be semi-translucent. Continuing to clear samples until all regions are uniformly transparent may lead to hydrogel softening, protein solubilization, and/or structural deformity in the rapidly clearing areas. In addition, overclearing is deleterious to endogenous fluorescence. Since tissue mounting in RIMS will lend an additional degree of optical transparency to tissues, it is crucial to remove tissues from SDS when the majority of tissue, or the portion of interest, is transparent, even if some regions appear under-cleared. This will help to ensure that the tissue macromolecular content is preserved. Alternatively, as opposed to terminating the incubation of tissue in 8% SDS prematurely, one may lower the percentage of SDS (e.g. from 8% to 4% SDS) in clearing buffer at the final stages of clearing.

Once the appropriate region of tissue appears optically transparent, wash tissue extensively at RT with gentle shaking. For rapid tissue processing, conduct a minimal wash step of 4-5 buffer exchanges in 1×PBS over a 12-24 hour period. Herein, residual SDS may precipitate, causing tissue cloudiness. To achieve more thorough removal of SDS, or to wash larger tissue blocks, wash the samples in either BBT or PBST for 1-2 days, with 4-5 buffer exchanges over the course of washing.

It is almost always preferable to perform wash steps of cleared samples at RT. We have found that additional 37° C. incubations of cleared tissue, or in particular, alternating between RT and 37° C. incubations, are hazardous to tissue structural integrity as cleared tissue lacks the structural support previously offered by lipids and thus must be handled with care. However, a single 37° C. sample wash after clearing and/or a final 37° C. sample wash that precedes sample mounting (step) may be beneficial to accelerating the diffusion of residual SDS from tissue and/or removing SDS precipitate, respectively.

Cleared and washed samples can be stored in 1×PBS (or PBST) containing 0.01% sodium azide at RT for 1-2 days. Tissues may become cloudy from salt precipitate, in which case wash with a few changes of PB.

(B) PACT-deCAL

The following steps have been optimized for clearing the dissected tibia of an adult mouse. It is important to tune the parameters of PACT-deCAL, such as the duration of bone incubations in clearing and decalcifying buffers, and the concentration of EDTA. Temperature fluctuations (e.g. from performing SDS or EDTA buffer changes with RT solutions rather than with pre-warmed 37° C. solutions, or from a waterbath that is unable to maintain a constant 37° C. environment) may adversely affect bone tissue morphology.

i. Place each bone-hydrogel sample into a 50 ml conical containing 10% SDS-PBS (pH 8.0) clearing buffer; gently rock the sample in a 37° C. shaking waterbath for 2 days.
   ii. Transfer the sample into 0.1 M EDTA in 1×PBS, pH 8.0, and incubate for ≥2 days in the 37° C. shaking waterbath.
   iii. Replace the EDTA-PBS with fresh 10% SDS-PBS (pH 8.0) and continue to clear the sample in a 37° C. shaking waterbath for 2 days.
   iv. Wash the sample in an excess volume of 1×PBS (pH 7.4) for 24 hours, performing 3-4 buffer exchanges.

(C) PARS Clearing

After polymerization, wash the perfusion lines with 1×PBS. Then replace the wash buffer with 8% SDS-PBS (pH 7.5) clearing buffer. This procedure can be accomplished easily via removing the PARS chamber from the shaking water bath (optional), turning off the pump, removing excess initiator buffer from the PARS chamber, and replacing it with 100 ml of 1× PBS to perform the wash. Circulate the wash buffer through the sample for 10 minutes. Afterwards, replace the buffer with 8% SDS-PBS (pH 7.5). Place the chamber back into the Ziploc bag and into the 37-42° C. water bath. Allow the SDS clearing buffer to recirculate through the system for 24 hours. Perform a buffer exchange with fresh 8% SDS-PBS (pH 7.5) clearing buffer daily until the recirculated fluid is no longer yellowish, after which the SDS solution can be refreshed less frequently (every 48-72 hours).

Whole organs are rapidly cleared in situ using PARS. However, if the user requires a time delay between clearing and immunostaining steps or must discontinue the PARS procedure, hydrogel-perfused whole organs may be excised following hydrogel polymerization (step 6B) or following the initiation of PARS clearing (step 7C(i)), and then stored in 4-8% SDS at 37° C. for up to one month. This allows whole organs to clear slowly during storage; their clearing progress must be monitored, albeit infrequently (e.g. weekly), as smaller, porous organs may become completely transparent in less than one month, wherein they should be transferred into 1×PBS (or PBST or BBT) containing 0.01% sodium azide at RT. Ensure that all storage solutions contain 0.01% sodium azide, and when ready to resume processing tissue, follow the protocol steps for PACT-based clearing and labeling (step 7A). Although this PACT-based clearing of PARS prepared whole organs conserves reagents and minimizes the constant oversight required during PARS clearing, it negates the principal benefits of PARS: efficiency and uniform sample preparation.

Check on the clearing progress daily; add additional SDS buffer to the PARS chamber if necessary, as depending on how well the Ziploc bag is sealed around the perfusion tubing, some buffer may evaporate over time.

The sample can be continuously perfused for up to 2 weeks until all desired organs have cleared, even if some organs appear clear within the first 24-48 hours. Alternatively, if all but one or two organs appear sufficiently transparent after a few days, one may proceed directly to step (iv) to flush SDS from tissue, and then excise all organs. The 1-2 semi-opaque excised organs are transferred into 8% SDS to finish clearing via PACT (see step 7A), while the organs that cleared more rapidly are immediately promoted to passive immunostaining (optional) and mounting (step 10) without further delay.

As with PACT-clearing, it is possible to overclear PARS samples, wherein protein and other tissue components are solubilized and the stabilizing hydrogel matrix begins to disintegrate. However, unlike PACT, connective tissue and bone structure provide additional structural support to organs as they are cleared. Generally, most major organs are cleared within a similar timeline of 24-48 hours, while the whole brain can take 1-2 weeks.

Once tissue appears optically transparent, perfuse 8 buffer changes of 200 ml BBT or 1× PBS with 0.01% sodium azide (pH 7.4) over a 2-day period in the 37-42° C. waterbath.

8. For samples that will be immunolabeled following clearing, the hydrogel matrix will be required to support the cleared tissue for several rounds of washing and multi-day incubations with gentle shaking. If the already delicate tissue-hydrogel matrix seems precariously fragile after clearing (this usually only occurs with thin-sectioned tissue), it is advisable to repeat the hydrogel embedding and polymerization steps (step 5 option A). This will stabilize tissue architecture during immunolabeling, prevent tissue loss or disintegration, and counteract expansion in mounting media. For cleared samples that will not undergo any immunohistochemical labeling steps prior to imaging, skip steps 8-9.

Single-Cell Phenotyping of Cleared Tissues

PACT and PARS prepared tissues are amenable to most standard immunohistochemical protocols; a list of validated small-molecule dyes, primary antibodies, and secondary fluorescent labels is provided in Table 4.

This PARS-histology protocol is sufficient to label molecular targets in the peripheral organs of mice and rats, with antibody amounts adjusted for body size. Individual users may need to adjust the incubation times and/or lengthen wash steps.

9. Prepare the primary antibody cocktail in IHC buffer. An antibody dilution of 1:200-400 is recommended, however a more or less concentrated antibody dilution may be required, depending on the tissue identity and bimolecular target. Perform passive labeling (option A) or perfusion-assisted labelling (option B). For passive labeling schemes (option A), thick-sectioned tissues should be incubated in enough of the antibody cocktail to fully bathe all surfaces, usually a few milliliters of antibody cocktail or less, if the tissue is placed in a minimally-sized container. For example, 1.5-5 ml Eppendorf tubes are recommended. For perfusion-assisted labeling using the PARS set-up (option B), approximately 20-100 ml primary antibody cocktail or labeling solution is required, depending on the tissue volume to be perfused and the total volume of the perfusion system (PARS tubing volume plus an additional amount of solution to partially fill the perfusion chamber).

(A) Passive Histology
   (i) Incubate the tissues in the primary antibody cocktail at RT with shaking for 3-7 days. For small-molecule stains or fluorescent dyes, a 1-3 day incubation is usually sufficient, and thin tissue sections (<500 um) may be stained within a few hours.

Figure 4B:
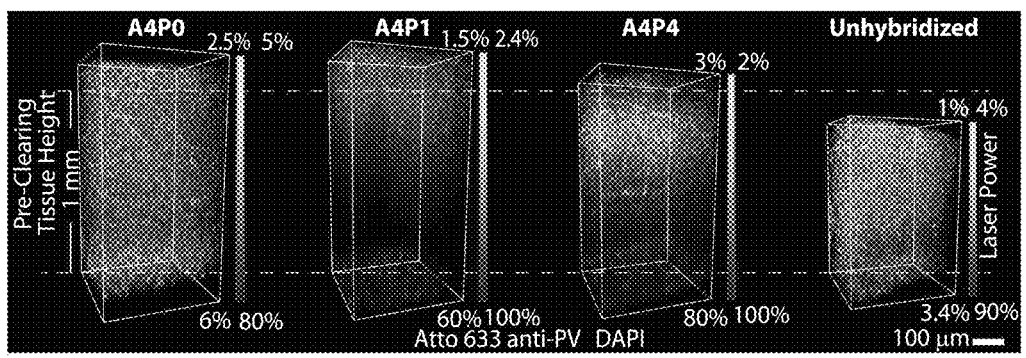
Figure 4C:
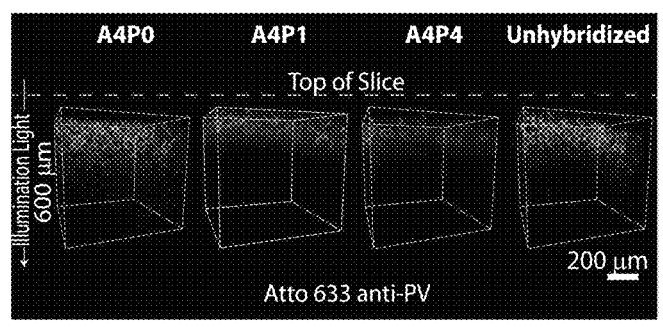
Figure 4D:
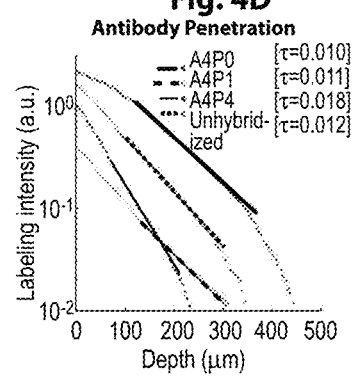
Figure 6A:
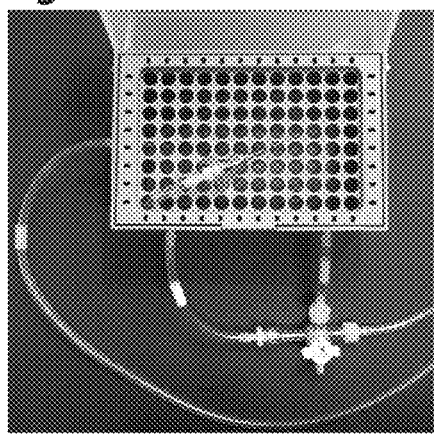
FIGS. 6A-6I depict, in accordance with various embodiments of the invention, assembling and working with the PARS chamber.
Figure 6B:
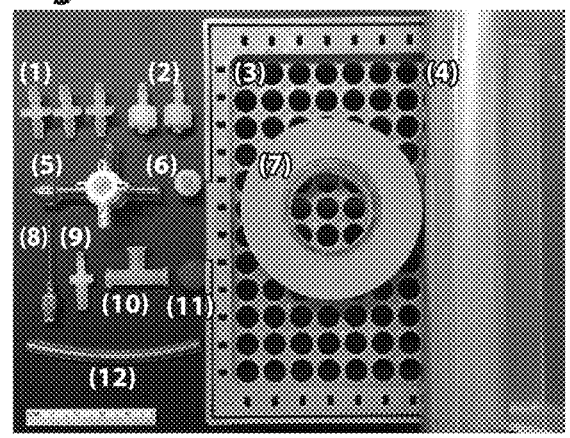
Figure 6C:
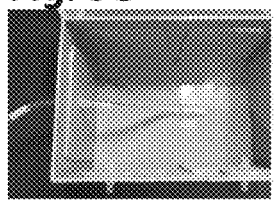
Figure 6D:
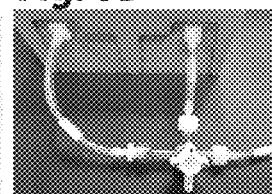
Figure 6E:
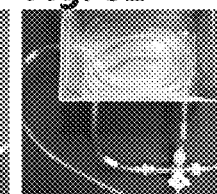
Figure 6F:
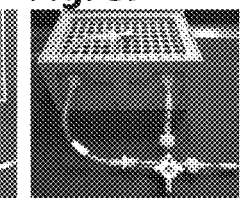
Figure 6G:
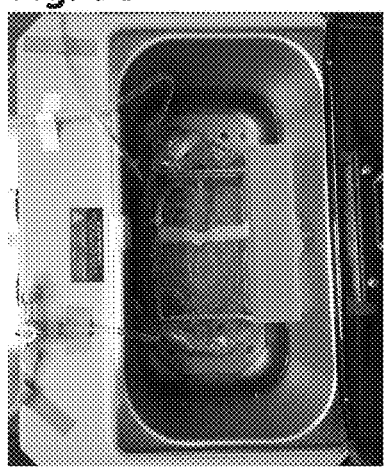
Figure 6H:
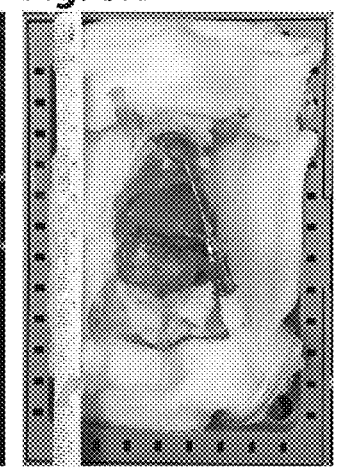
Figure 6I:
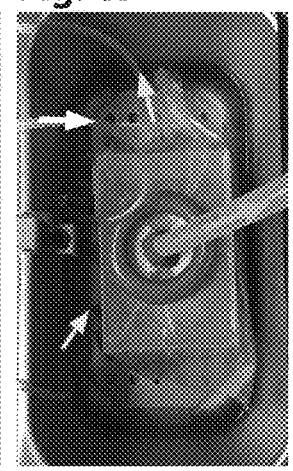

The duration of primary antibody incubation must be determined on a case-specific basis (see antibody penetration guidelines, FIG. 4D). It is highly recommended to use smaller antibody formats for thick-tissue staining, when available. For A4P0-embedded rodent brain tissue, a full IgG will penetrate approximately 500 µm over a 3-day incubation at RT with shaking. This length of time is often sufficient for 1 mm tissue slices if the tissue can be imaged from either side. For A4P4-embedded rodent brain tissue, a full IgG will penetrate approximately 200 µm over a 3-day incubation at RT with shaking.

(ii) To remove unbound antibody or stain, wash the samples in an excess volume of 1× PBS buffer: transfer the samples to a larger container (e.g. a 15-50 ml conical tube) and perform 4-5 1×PBS buffer exchanges over the course of one day. Larger tissue blocks, PACT-cleared whole organs, and samples in which high background or non-specific antibody binding are common, should be washed for 2 days in PBST, with 4-5 buffer exchanges.
   (iii) Prepare the secondary antibody cocktail (1:200-400 recommended dilution) in IHC buffer. Fab fragment secondary antibodies are preferred.
   (iv) Incubate washed samples in the secondary antibody cocktail for 2-5 days at RT and with shaking. Again, samples may be transferred to 1.5-5 ml Eppendorf tubes in order to accomplish staining with a minimal volume of antibody.
   (v) Wash labeled samples with 4-5 buffer exchanges of 1×PBS over 1 day.

Perfusion-Assisted Labeling
   (i) Replace the PBST in the perfusion tubing and PARS chamber with the primary antibody cocktail or stain and continuously perfuse the sample for 3 days.
   (ii) Exchange the antibody cocktail for 1×PBS and wash the sample through perfusing 4 buffer changes of 200 ml 1×PBS over the course of 1 day.
   (iii) Prepare the secondary antibody cocktail (1:200-400 recommended dilution) in IHC buffer. Again, Fab secondary antibodies are preferred.
   (iv) Replace the 1×PBS in the perfusion tubing and PARS chamber with the secondary antibody cocktail (or stain), and continuously perfuse the sample for 3 days.
   (v) Exchange the antibody cocktail for 1×PBS and wash the sample through perfusing 4 buffer changes of 200 ml 1×PBS over the course of 1 day.

RIMS (Refractive Index Matching Solutions) for PACT and PARS Samples

10. Calculate the refractive index (RI) of the tissue to be mounted and imaged. Use a refractometer to measure the sample RI according to the manufacturer's instructions.

11. Prepare a sample-optimized RIMS formulation by adjusting the amount of Histodenz™ dissolved in 0.02 M phosphate buffer. For most tissues, a RIMS formulation with RI~1.46-1.47 is optimal. For bone, prepare a graded series of RIMS formulations: RIMS with RI~1.42, RIMS with RI~1.46, and RIMS with RI~1.48-1.49. For imaging thick tissue using immersion objectives corrected for immersion media with a refractive index between 1.38-1.42, it is sometimes beneficial to match the refractive index of RIMS to that of the immersion media. For example, when using the LD-Plan Apochromat 20×1.0 N.A. Scale objective (Zeiss), RIMS with RI~1.42 will help to reduce image distortion in the Z-direction.

As discussed in the Experimental Design section, different mounting solutions can be substituted for RIMS.

12. Submerge the sample in excess RIMS (i.e. in a capped 15, 50 ml conical tube or in a 5 ml Eppendorf tube, filled ~¾ full with RIMS) and incubate at RT until it reaches the desired transparency. While thin tissue sections may become transparent in less than a single day, a whole rat brain requires a 1-week incubation in RIMS to achieve thorough RI homogenization throughout the sample. These incubation times may be shortened significantly by placing samples on a nutating mixer. Bone should be carried through a graded series of RIMS incubations, spending one day in each of RIMS-1.42, RIMS-1.46, and RIMS-1.48-9. Likewise, perform a graded series of RIMS incubations for very fragile tissues, as this will prevent the unlikely event of tissue damage from rapid shrinking-swelling.

Samples may be stored long-term (~3 months) in RIMS. Herein, RIMS-submerged samples should be kept in an airtight container at RT and protected from light. Alternatively, when short-term sample storage at 4° C. is mandatory, samples may be mounted in cRIMS; store in a dry, air-tight container.

Upon RIMS immersion, cleared tissue will shrink over the course of a few hours (e.g. A4P0-embedded coronal mouse brain sections shrink ~20%, size fluctuations are reduced in samples embedded in PFA-containing hydrogels). Continued incubation in RIMS will lead to gradual tissue expansion back to its starting size as RIMS penetrates the tissue. These size changes may confound the visualization of sub/cellular morphology or introduce apparent tissue deformities. Thus, imaging should not be undertaken before the sample has equilibrated in RIMS. However, if the goal is coarse cellular phenotyping and/or rapid tissue visualization, a much shorter RIMS incubation may be performed (1-4 hours, or until the sample is sufficiently transparent).

13. Transfer the refractive-index homogenized tissue into an airtight container (e.g. vacutainers or conical with rubber stopper) and fill the container with fresh RIMS (or with an alternative mounting media such as sRIMS or 87% (vol/vol) glycerol) until it just covers the sample. Insert a 1"-long needle into the rubber stopper, connect the needle to the house vacuum line, and degas the sample for 5-10 minutes. When ready to image, proceed to next step for mounting instructions.

Although RIMS outperforms sRIMS in our hands, the primary ingredient of sRIMS—sorbitol not only offers a cost advantage over Histodenz™, but it is also commonly available in research laboratories owing to its broad use as a cell culture reagent. Importantly, sRIMS grants superior imaging resolution over glycerol.

For fine-scale analyses (e.g. of subcellular morphology) or long image acquisitions, do NOT image samples immediately following their placement in RIMS. Wait until their initial expansion after RIMS-mounting has plateaued (e.g. several days after mounting 1 mm slices).

It is important that RIMS or other mounting media be prepared with 0.01% sodium azide to prevent microbial growth in mounted tissue. Limit the number of air bubbles in sealed slides.

Acquisition

14. Mount and image tissues with a confocal microscope (option A) or with a light sheet fluorescence microscope (option B).
    A. Confocal Imaging
    (i) Prepare glass slides with appropriately sized tissue wells, such as 0.5-1.0 mm thick iSpacers, which may be stacked to create deeper wells, or silicon sheets, which may be cut to size. If the silicone spacer is adhesive free, apply vacuum grease to the edge of the spacer. Place samples inside the spacer. Slightly overfill the spacer with RIMS and place a coverslip on top of the spacer. Gently press down to seal the coverslip. Remove overflow RIMS with a Kimwipe.
    (ii) Place RI-homogenized, thick-sectioned tissues and small whole-organs on a glass slide: place the tissue inside the sample well; overfill the well with fresh, degassed RIMS of an appropriate RI such that it forms a convex meniscus. Take care not to introduce bubbles into RIMS, or between the tissue and slide.
    (iii) Place a coverglass over the sample well, using vacuum grease or nail polish to seal the coverglass onto the well edges. Again, avoid sealing bubbles into the sample well; if this occurs, remove the coverglass and repeat this step, adding more RIMS to the well as necessary.
    (iv) To image PACT and PARS-cleared samples with a standard microscopy set-up (e.g. a single-photon confocal microscope), use a multi-immersion objective with a refractive index correction collar to match the RI of the mounted sample: RI~1.46-1.47 for most tissues, or ~1.48-1.49 for bone. For immersion media, use glycerol with the same RI as the mounting RIMS.
    (v) Determine optimum acquisition parameters, and apply these. Acquisition parameters (e.g. PMT gain, laser power and scanning speed) need to be optimized for each sample based on the desired final image quality.

To allow for accurate stitching, acquisition software should be set to acquire tiles with overlap (>10%). If the microscope has the option, it is useful to use the auto Z brightness correction (see FIG. 4B). In Zen (Zeiss), Auto Z provides an automatic gradual adjustment of the detector gain, amplifier offset, amplifier gain, and laser intensity setting between the first and last optical slice of a Z Stack. This will help to insure that signal intensity is uniform throughout the sample since even clear tissue will scatter at depth.

(B) Light Sheet Microscopy
  i. Mix the glycerol in the immersion chamber using a pipette tip (see FIG. 8) to prevent optical aberrations due to inhomogeneous media and let the glycerol settle for ~1 hour.
  ii. Stabilize the sample in a quartz cuvette by submerging the sample in RIMS within the cuvette and arranging gel pieces around the sample. We use 1% low-melt agarose gel.
  iii. Position the cuvette on the custom sample-holder, which may be 3D-printed, as in FIG. 8B, and attach it to the sample translation stage.

Make sure that the cuvette is properly sealed (e.g. with parafilm, see FIG. 8B), as evaporation of water from RIMS will cause severe aberrations.

iv. Before lowering the sample in the immersion chamber verify that the light sheet is centered in the field-of-view and that the objective lens is in focus.
  v. Lower the sample into the immersion chamber.
  vi. Readjust the light sheet position to the center of the field-of-view and re-focus the objective lens.

vii. Change the settings of the camera to a light sheet mode, activate the driving voltage of the galvo scanner via the function generator and trigger the camera using the external trigger. The delay between the galvo scanner and the camera's external trigger signal should be fine-tuned in order to achieve optimal synchronization; here we used a custom automatic MATLAB program to find the optimum delay, the software is available on demand.

viii. Set the image acquisition parameters (e.g. laser power, scan depth and the scan resolution in Z) and initiate the acquisition sequence.

3D Image Visualization

We outline workflows for tracing a visualization using tools summarized in Table 3. Interactive processing and visualization software will perform best on a workstation with substantial RAM (>16 GB) and GPU memory (>=1 GB). The tools mentioned are multi-threaded and can often exploit multi-core processors to further speed up computations.

15. For the volumetric visualization of large images that do not fit in RAM, select one of the following workflows: (option A) using Imaris (BitPlane), (option B) using TeraStitcher and Vaa3D TeraFly, or (option C) using Vaa3D TeraConvert plugin and Vaa3D TeraFly. Estimated timing is based on tests with a 30 GB image stack visualized on a 64 bit Windows 8 machine with Intel i7-3770 CPU and 16 GB of RAM.

(A) Imaris (v7.7.1)
  (i) Stitch image tiles using acquisition software
  (ii) Open raw image stack (Timing: 12 minutes)
  (iii) Save loaded image in Imaris .ims format (Timing: 24 minutes). This is useful to streamline future loading and visualization. Reloading the resulting .ims file thereafter takes a few seconds.
  (iv) Visualize using Imaris volumetric view Surpass, annotate and perform additional image processing using Imaris XTensions.

(B) TeraStitcher and Vaa3D TeraFly Plugin (v2.921/v0.999)
  Stitch tiles and save a multi-res volume using TeraStitcher (steps (i)-(iii), also see protocol), visualize the resulting image using Vaa3D TeraFly plugin in steps (iv)-(v).
  (i) Store individual fields of view as separate .tif stacks in a hierarchical set of subdirectories as used by TeraStitcher using the layout specified in https://github.com/abria/TeraStitcher/wiki/User's-guide.
  (ii) Stitch images using either the TeraStitcher standalone program or the Vaa3D plugin-in (Plug-In>image_stitching>TeraStitcher>tera stitcher). TeraStitcher requires that the user specify the voxel dimensions, tile size and tile overlap used during acquisition.
  (iii) Save the stitched output as a tiled, multi-resolution volume.
  (iv) In Vaa3D, start the TeraFly plugin (Plug-In>Teramanager>TeraFly) and select the directory containing the exported multi-res tiled volume.
  (v) The 3D view window will now display the whole image dataset and progressively load in higher resolution sub-volumes as the user zooms in to particular parts of the image. Utilize Vaa3D's color map, annotation and analysis tools on selected sub-volumes.

(C) Vaa3D TeraConvert and TeraFly Plugin (v2.921/v0.999)
  Use the Vaa3D TeraConvert plugin to convert an already stitched image to tiled, multi-res format (steps (i)-(ii)) and then use the Vaa3D TeraFly plugin to visualize the resulting image by following steps (iii)-(iv).
  (i) Stitch images using acquisition software. Save individual z-sections as a numbered sequence of files in a single directory using either acquisition software export options or by using the BioFormats importer plugin in Fiji to load as a Virtual Stack and then using the BioFormats exporter plugin to save as an OME-TIFF file (see http://www<dot>openmicroscopy<dot>org/site/support/ome-model/ome-tiff/), selecting the option to save each channel and z-section in a separate file.
  (ii) Use TeraConvert plugin (Plug-In>Teramanager>TeraConverter) to convert the stored images into a multi-resolution tiled volume by specifying the location of the image series and specifying Vaa3D raw tiled format and an output directory.
    Pay attention to Estimated RAM usage in the TeraConvert plugin window. To reduce the memory needed by TeraConvert, deselect the checkboxes next to the lowest resolution output formats (starting from the one with the smallest x,y,z values) until the "estimated RAM" is less than the available RAM.
  (iii) In Vaa3D, start the TeraFly plugin (Plug-In>Teramanager>TeraFly) and select the directory containing the exported multi-res tiled volume.
  (iv) The 3D view window will now display the whole image dataset and progressively load in higher resolution sub-volumes as the user zooms in to particular parts of the image. Utilize Vaa3D's color map, annotation and analysis tools on selected sub-volumes.

3D Image Analysis

A typical workflow is to first run automated tracing to generate initial estimates of morphology and then perform more detailed semi-automated editing to refine the tracing. Automated tracing is computationally intensive so it is essential to restrict processing to small regions-of-interest (ROIs) or cropped out sub-volumes and manually merge the traces afterwards. Also, it is worth noting that semi-automated and manual editing of traces can be greatly accelerated by taking time to learn keyboard shortcuts for a given software tool rather than clicking on graphical user interface elements such as menus or buttons.

Automate the tracing of relevant image elements using either Imaris (option A) or neuTube (option B). Alternatively, one may perform tracing using the Vaa3D-Neuron2 plugin, which has been reviewed previously. The sample workflows in options A-B and the times reported, vida infra, are based on our tracing of the test image shown in FIG. 9, which consists of two labeled neurons in mouse striatum imaged over two fields of view on an LSM 780 @ 25× magnification and stitched in Zen (Zeiss) to produce a single channel, 8-bit, 300 MB image stack of size: 1024×2048×150=$3.15 \times 10^8$ voxels covering 480×960×175 $um^3$~0.08 $mm^3$ of tissue.

(A) neuTube (v1.0)
  (i) Load image into neuTube. For commercial image formats not recognized by neuTube, use Fiji Bioformats Importer and exporter plugins to convert to .tif
  (ii) Select View>3D View to visualize a volumetric rendering. Click the Transfer Function under Control and Settings panel to adjust contrast in the 3D view (see FIG. 9A.1, FIG. 16A). In a large volume containing many cells, center the cursor on a region of interest and right click and select >Open Zoom In View to show only image data for a sub-region.
  (iii) Left-click on a cell body and select >Trace to automatically trace a neurite from that point. Successively visit remaining untraced neurites associated with the cell and click Trace on each (see FIG. 9A2). (Timing: 3 minutes)

neuTube includes a fully automatic tracing option but we found a semi-automatic tracing approach (which requires 1-2 clicks per neurite) to be faster and more stable.

(B) Imaris (v7.7.1)
  (i) Load image file. Make sure that voxel dimensions are correct via the Edit>Image Properties . . . menu and correct if necessary and use Display Adjustment to adjust contrast.
  (ii) Add a new Filament to the Surpass Scene session
  (iii) In the AutoPath tracing wizard, select the AutoPath algorithm and select the ROI checkbox.

Specify the smallest possible ROI enclosing each neuron of interest to assure fast processing (see FIG. 9.B1, FIG. 16B).

(iv) Adjust thresholds for automatic detection of starting points (i.e., soma) and seed points. (see FIG. 9.B2) The goal is to have seed points distributed along the neurites but avoid extra seed points in the background which will slow tracing and produce errors that need to be corrected later. Depending on background noise and morphological complexity it may be faster to identify starting and seed points by manual shift+clicking. The Autopath wizard will then find paths connecting seed points into a tree of neurite segments.

Within the same program (neuTube or Imaris, respectively), manually refine the automated tracing results that were that were generated in 16. Stepwise instructions are presented for both neuTube (option A) and Imaris (option B).

We believe that the following guidelines for manipulating automated results will be broadly applicable to a variety of tracing projects. However, they do not represent an exhaustive list of the capabilities of the softwares and the user should not feel limited to this set of keystrokes.

(A) neuTube (v1.0)
  (i) After initial tracing yields good coverage of neurites, select and delete erroneous nodes, add connections and extend fibers by selecting nodes and using the right-click context menu (see FIG. 9.A3-A4). See extensive tutorial on editing at http://www.<dot>neutracing<dot>com/manual
  (ii) To save tracing results use File>Save SWC. Alternately, File>Export Scaled SWC . . . allows the user to specify the relative scaling of XY and Z-axes in to match acquisition parameters and produce SWC data in physical units.

(B) Imaris (v7.7.1)
  (i) Manually refine the automatically traced result from AutoPath. For example, users can extend individual traced paths by adding seed points and manually editing to correct errors.
  (ii) If necessary, remove incorrect branches using the branch select mode and delete key. To split branches, use the node select mode and delete individual nodes. Select a pair of endpoints and the Join option to find a path between them (see FIG. 9.B3).
  (iii) To extend neurites using the AutoPath method select the filament corresponding to the traced component to be extended and choose "Selection as Starting Point" to perform shortest path computation. Once the computation is done (Timing: 10 minutes for whole test image, less for smaller ROIs), the AutoPath mode will interactively trace from the cursor position back to the selected component. Shift+clicking will add the displayed candidate path (see FIG. 9.B4).
  (iv) If necessary, use the filament editing tools to perform additional operations such as smoothing filaments, estimating neurite diameter, detection and annotation of spines, and fully manual tracing (refer to user manual for details).
  (v) Visualize the resulting traces using Imaris Vantage or export tracing geometry in NEURON .hoc file format (for up-to-date list of NEURON .hoc resources: http://www<dot>neuron<dot>yale<dot>edu/neuron/publications) for use in other analysis tools.

Troubleshooting

See Table 5 for troubleshooting guidance.

Anticipated Results

PACT, PARS and RIMS collectively form a tissue clearing toolkit that is versatile, user-friendly and sample-friendly across tissue types. Building on past research, we detail here how both PACT and PARS methodologies are amenable to rapid, high-throughput histopathology of rodent (FIG. 1A-E) and human (FIG. 1F-G) tissue samples alike, whether through the visualization of natively expressed fluorescent markers (FIG. 1A-E, FIG. 5C, FIG. 8C, and FIG. 12D-E) or through immunolabeling whole-organ and thick tissue samples (FIG. 1F-G, FIG. 4B-C, FIG. 5D, FIG. 6A, and FIG. 15B) after clearing. Furthermore, the formation of a cross-linked, tissue-hydrogel matrix allows for rigorous detergent-based clearing with only minimal leaching of proteins into clearing buffer (FIG. 3A, FIG. 11A-B) and no detectable loss in YFP fluorescence between uncleared and cleared samples. In addition to its refractive index matching capability, RIMS also serves to preserve the molecular content of mounted samples: no protein was measured to leach out of mounted samples after a one week incubation and YFP fluorescence was readily detected in cleared samples that were stored in RIMS for 3 months. The enhanced optical transparency of delipidized and refractive-index matched tissues permits high-resolution detection of endogenously expressed fluorescent proteins, antibody-labeled proteins, and nucleic acid transcripts at the single molecule level (FISH), usually with similar intensity and lower background signals than are seen in uncleared tissues (FIG. 5C-D, confocal images for control versus cleared samples; FIG. 13).

Amongst the recently developed PACT variations summarized here are dedicated protocols for specialty cases within tissue clearing. These include PACT-processing of fragile tissue samples (see A4P1-A4P4 conditions in FIG. 3, 4, 5A-C), pre-PACT tissue staining with Sudan Black B to mask autofluorescence in thick tissues (FIG. 12, Supplementary Methods), PACT-deCAL for clearing and imaging fluorescently-labeled bone, and ePACT for tissue clearing through expansion (FIG. 13, Supplementary Methods). With respect to the latter, PACT tissues have previously been carried through to FISH studies, where clearing and slight tissue swelling benefited the visualization of single, labeled transcripts. In ePACT, cellular components that were once poorly resolved in uncleared sections become visible (FIG. 13B). Combining these techniques offers the potential to optically distinguish multiple transcripts within the expanded sample space of a cell.

To accompany these methods for chemically clearing a variety of tissue types, we extended our RIMS formulation guidelines to include recipes for different tissue types (i.e., to better match the refractive indices of different samples. Since PACT and PARS have now been optimized to clear a wide variety of tissues, the method can further benefit from exploring alternative labeling schemes for visualizing protein and nucleic acid targets in thick tissues (FIG. 15). Although traditional antibody-based labeling methods have been used very effectively to illuminate cell phenotype and tissue morphology (FIG. 1G, FIG. 5D, and previous work), they can be both cumbersome and costly. The slow penetration of full-format immunoglobulins in thick tissue necessitates long incubations (FIG. 4B-D), to the detriment of sample integrity. Herein, camelid nanobodies (FIG. 15) and protein affinity tags (i.e., SNAP-tag (see Keppler, A. et al. A general method for the covalent labeling of fusion proteins with small molecules in vivo. *Nat. Biotechnol.* 21, 86-89 (2003)), Halo-tag (see Los, G. V. et al. HatoTag: A novel protein labeling technology for cell imaging and protein analysis. *ACS Chem. Biol.* 3, 373-382 (2008)), CLIP-tag (see Gautier, A. et al. An engineered protein tag for multi-protein labeling in living cells. *Chem. Biol.* 15, 128-136 (2008)), and TMP-tag (see Miller, L. W., Cai, Y. F., Sheetz, M. P. & Cornish, V. W. In vivo protein labeling with trimethoprim conjugates: a flexible chemical tag. *Nat. Methods* 2, 255-257 (2005)) present chemically stable and potentially cost-effective alternatives. With the ability to easily penetrate thick tissue, these reagents can recognize and bind their respective targets, either a cognate antigen or tagged protein, with high specificity and rapid kinetics. Also, by using dyes that are several-fold brighter, highly photostable, and easier to separate spectrally than fluorescent proteins, protein affinity reagents can provide an excellent signal-to-noise ratio in labeled tissues (see Kohl, J. et al. Ultrafast tissue staining with chemical tags. *Proc. Natl. Acad. Sci. USA* 111, E3805-E3814 (2014)).

Two major bottlenecks in the translation of fixed, unprocessed tissue banks into analyzable image databases are (1) acquisition time of thick tissues at high-resolution and (2) the computational demands to convert raw image stacks into manageable datasets for morphological study. Light sheet microscopy has recently been applied to imaging large cleared volumes as it substantially reduces the acquisition time. Here we provide a basic scheme for relatively inexpensive design of a light sheet microscope that enables fast and high-resolution imaging of cleared samples (FIG. 8A-B) and show its compatibility with PACT. A representative volume (1 mm depth) PACT-cleared mouse brain slice imaged at 45 frames per second, can be seen in FIG. 8C. In comparison with traditional confocal microscopes, a frame rate of 45 frames per second shows ~10-100 times improvement in image acquisition speeds and thus allows for rapid imaging of large cleared samples, in addition to its recognized utility for live-cell imaging (see Keller, P. J. & Ahrens, M. B. Visualizing whole-brain activity and development at the single-cell level using light-sheet microscopy. *Neuron* 85, 462-483 (2015)). In addition to increased speed, light sheet microscopy significantly reduces photobleaching (1/300-1/5000 photon energy exposure), which is critical for imaging dim samples and especially for conducting smFISH experiments, where the 20-100 single fluorophore-labeled probes are used to visualize individual transcripts.

Regardless of the microscopy set-up, image acquisitions for large tissue samples generate raw data files that are on the order of gigabytes or even terabytes in size. These data must be converted into a file format that allows data handling and visualization on computer workstations that are available to standard research laboratories. Many software packages for image analysis were not designed to accommodate such file sizes and inevitably crash partway through the computational process. Thus, we have endeavored to present a broadly applicable workflow for image data handling (see FIG. 9, Table 3), which will guide the user through the process of transferring raw image files into the image analysis software packages that we feel are most capable of performing basic functions such as tract-tracing and cell-mapping.

In summary, we have validated the ability of PACT, PARS and RIMS to prepare a variety of tissue samples for imaging via confocal and light sheet microscopy. With these methods in hand, biologists may tackle the broad spectrum of scientific demands, from the meticulous analysis of isolated cell niches, to the global interrogation of intact biological systems.

TABLE 1

Current and Potential Biomedical Applications of PARS and PACT

| Application | Cleared Tissue |
|---|---|
| Biodistribution of chemicals or biologicals (e.g. virus infectivity, gene therapies) | Whole-body clearing (see FIG. 1A-E) |
| Mapping discrete cellular niches, such as 3D genetic makeup and architecture of tumors, stem cell niches | PACT of tumor biopsies (see Yang, B. et al. Single-cell phenotyping within transparent intact tissue through whole-body clearing. *Cell* 158, 945-958 (2014)) and whole brain, PARS for rodent cancer models |
| Monitoring the progression of cell death and tissue damage (i.e., in stroke, peripheral infarcts), and the corresponding neurogenesis | PARS for whole-body, targeted vasculature fixation and immunolabeling |
| Tract tracing complex long-range fiber bundles (e.g. vagus nerve) and whole body vasculature (i.e., both circulatory and lymphatic systems); Short- and Long-range cellular 3D mapping (see Ross, J.D., Cullen, D.K., Harris, J.P., LaPlaca, M.C. & DeWeerth, S.P.A three-dimensional image processing program for accurate, rapid, and semi-automated segmentation of neuronal somata with dense neurite outgrowth. *Front. Neuroanat.* 9 (2015)) (including via neuronal positioning system, NPS (see Tsuriel, S., Gudes, S., Draft, R.W., Binshtok, A.M. & Lichtman, J.W. Multispectral labeling technique to map many neighboring axonal projections in the same tissue. *Nat. Methods* 12, 547-552 (2015)), and via Brainbow (see Livet, J. et al. Transgenic strategies for combinatorial expression of fluorescent proteins in the nervous system. *Nature* 450, 56-62 (2007)) | PARS with whole-body targeted IHC, PARS-CSF (spinal cord), PACT-deCAL for vertebral column, ePACT for subcellular spectral resolution of overlapping NPS vesicles, Brainbow labeling, and FISH probes |
| Following neurodevelopment (neural stem cell differentiation), neurogenesis, and nerve/axon regeneration | PARS |
| Tracking myelination trajectory over lifetime and demyelination in disease states (autism, traumatic brain injury, multiple sclerosis) | PACT and PARS with IHC for myelin-associated proteins and markers of inflammation (see FIG. 5D) |
| Studying the brain-gut connection, microbiome, blood brain barrier permeability | PARS |
| Assessing the effects of peripheral immunoactivation on cognition and health | PARS with immunohistochemistry (IHC) for cytokines, inflammation, and neuronal markers |
| Imaging through dense, complex tissues (e.g. bone marrow stem cells) | PACT-deCAL for through-bone imaging |
| Exploring topics in microbiology, including biofilms (characterizing biofilm structure and the interaction of different cellular layers), the heterogeneity and distribution of microbes that occupy the same niche | PACT with considerations for fragile samples (e.g. PACT-hydrogel formulated with paraformaldehyde and/or bis-acrylamide) so that bacterial colonies are retained in tissue/biofilm samples during clearing |

TABLE 1-continued

Current and Potential Biomedical Applications of PARS and PACT

| Application | Cleared Tissue |
|---|---|
| Diffusion Tensor Imaging (DTI) (see Basser, P.J., Mattiello, J. & Lebihan, D. MR Diffusion Tensor Spectroscopy and Imaging. *Biophys.* 1 66, 259-267 (1994)) and Spectral Confocal Reflectance Microscopy (SCoRe, for label-free in vivo imaging of myelinated axons) see (Schain, A.J., Hill, R.A. & Grutzendler, J. Label-free in vivo imaging of myelinated axons in health and disease with spectral confocal reflectance microscopy. *Nat. Med.* 20, 443-449 (2014)) | Future potential for ex vivo variation of DTI, wherein PARS-based diffusion of and materials and immunolabels grants whole-organism imaging |

TABLE 2

Methodological comparison and important considerations when choosing a tissue clearing protocol that achieves both macromolecular extraction and optical clarity.

| | Sample Preparation[a] | Chemical Clearing[b] | Optical Clearing[c] | Processing Time[d] | Size Fluctuations | Fluorescence, IHC Compatibility[e] |
|---|---|---|---|---|---|---|
| 3DISCO | Graded tetrahydrofuran | dichloromethane lipid solubilization | dibenzyl ether and/or BABB[f] | <week (1-2 days) | No tissue expansion reported; tissue shrinkage with dehydration | IHC |
| iDISCO | Rounds of dehydration, bleaching, rehydration | | | 2-3 weeks (1-2 days) | | IHC |
| CUBIC | n/a | Aminoalcohol-based tissue decolorization and lipid removal (15% Triton X-100, 25% urea, 25% NNNN'tetrakis(2-hydroxypropyl)ethylenediamine); ≥5 days per organ | Scale-based optical clearing (50% sucrose, 25% urea, 10% nitrilotriethanol, 0.1% Triton X-100); ≥2 days | 2 weeks, 10-14 days (≤10 days) | Transient and reversible | IHC/F |
| CUBIC decolorization | | | | | | IHC/F |
| CLARITY | Formation of tissue - hydrogel hybrid | electrophoretic tissue clearing: lipid removal with SDS | RI matching with Focus Clear or glycerol | 10 days | Transient, reversible tissue expansion during the process | IHC/F |
| Adv. CLARITY | | | | | | IHC/F |
| Passive CLARITY | | | | weeks | | IHC/F |
| PARS | Formation of tissue - hydrogel hybrid | Perfusion-based or passive lipid removal with SDS | RI matching with RIMS, sRIMS, or glycerol | <2 weeks (1 week) | Transient, reversible tissue expansion during the process; gradual tissue expansion in RIMS mounting media | IHC/F |
| PACT | | | | ≥month | | IHC/F |
| ExM | Formation of tissue - hydrogel hybrid | (Proteinase K digestion) | Clearing through water absorption; possible RI homogenization with digestion | <week | 4-5x linear expansion | IHC |

[a]Sample preparation aside from standard fixation and brief post-fixation (e.g. 4% PFA transcardial perfusion)
[b]Chemically/mechanically removing tissue macromolecular components (e.g. lipids, heme) to improve light penetration and reduce light scattering
[c]Homogenizing the refractive indices throughout heterogeneous tissues and at all material interfaces between the sample and objective lens (e.g. tissue, mounting media, coverglass, immersion media) so as reduce light scattering during optical imaging; often involves tissue dehydration and/or immersion in RI matching solution or solvent and/or hyperhydration, but not removal of cellular/macromolecular structures
[d]Processing time is the approximate time from sample collection to sample mounting for a whole adult mouse brain, not including IHC, as based on published reports; the time in parentheses is the approximate clearing time
[e]IHC: Compatible with small-molecule and antibody-based immunohistochemistry, some restrictions in immunofluorescence (e.g. rapid signal decay) and/or some reservations about harsh tissue treatments that may adversely affect tissue integrity or labeling; IHC/F: Compatible with IHC and immunofluorescent labeling, validated for (>0.5 mm) depth of antibody penetration and for a wide range of fluorophore wavelengths; IHC: IHC-compatible, but only with use of custom probes.
[f]BABB: a mixture of benzyl-alcohol and benzyl-benzoate

TABLE 3

Image Analysis and Visualization Tools. A list of image analysis tools appropriate for processing cleared tissue volumes including functionality for stitching, visualization, and tracing.

| Name | Platform | Stitching | Out of core visualization | Semi-automated tracing | Notes |
|---|---|---|---|---|---|
| Imaris (Bitplane) | Commercial Win/Mac | No | Yes | Yes Filament Tracer plugin | Best loading and volumetric rendering of large (out-of-core) images |
| Vaa3D | Open Source Win/Mac/Linux | Yes iStitch or Terastitcher plugin | Yes TeraFly plugin | Yes Vaa3D-Neuron2 plugin | |
| Fiji | Open Source Win/Mac/Linux | Yes Stitching Plugin | Partial Virtual stacks[a] or BigDataViewer[b] | Yes Simple Neurite tracer | |
| neuTube | Open Source Win/Mac/Linux | No | No | Yes | Fastest semi-automated tracing interface |

[a]Data Browser ImageJ plugin (LOCI), see http://loci<dot>wisc<dot>edu/software/data-browser
[b]BigDataViewer, see http://fiji<dot>sc/BigDataViewer

TABLE 4

Antibodies and small-molecule stains validated for cell-phenotyping in PACT- and PARS-processed tissues.

| Label | Supplier and/or Formulation |
|---|---|
| Nucleic acid and molecular labels, cell-type and tissue-type small-molecule stains | |
| DAPI (4',6-Diamidino-2-Phenylindole, Dihydrochloride) | Life technologies (#D-1306), Grand Island, NY 0.1-10 μg/ml |
| Hoechst | Cell signaling |
| NeuroTrace 530/615 Red Fluorescent Nissl Stain | Life Technologies (#N-21482), Grand Island, NY 1:50 dilution |
| SYTO 24 | Life technologies (#S-7559), Grand Island, NY 1:200 dilution |
| DRAQ5 | Cell signaling (#4084) Danvers, MA 1:200 dilution |
| Acridine Orange | Life technologies (#A-1301), Grand Island, NY 100 μg/ml dilution |
| Lectin, DyLight 488 conjugate | Vector laboratories (#L-1174), Burlingame, CA 1:100 dilution |
| Methylene blue | Sigma-Aldrich (#66720) St. Louis, MO 1 μg/ml |
| Atto-565 conjugated phalloidin | Sigma-Aldrich (#94072) St. Louis, MO 1:100 dilution |
| Alexa Fluor ® 647 Phalloidin | Life technologies (#A-22287), Grand Island, NY 0.5 μM in PBS |
| Primary Antibodies [a] | |
| Mouse anti-pan-cytokeratin (AE1/AE3) antibody, Alexa Fluor 488 conjugate | eBiosciences (#53-9003) San Diego, CA 1:100 dilution |
| Synthetic anti-GFAP nanobody, Atto 488 conjugate | GFAP nanobody producing according to published methods 1:100 dilution (Purified GFAP nanobodies were first conjugated to Atto 488 (Sigma-Aldrich), diluted in dH$_2$O to 1 mg/ml stock, and then diluted 1:100 for tissue labeling) |
| Chicken anti-tyrosine hydroxylase (TH) IgY | Aves Labs (#TYH) Tigard, OR 1:400 dilution |
| Chicken anti-glial fibrillary acidic protein (GFAP) IgY | Aves Labs (#GFAP) Tigard, OR 1:400 dilution |
| Rabbit anti-ionized calcium-binding adapter molecule 1 (Iba1) IgG | Biocare medical (#CP 290A) Concord, CA 1:200 dilution |
| Rabbit anti-integrin β4 and anti-integrin β5 IgGs | Santa Cruz Biotechnology (β4: sc-9090, β5: sc-14010) Dallas, TX 1:200 dilution |
| Rabbit anti-n tubulin IgG | Santa Cruz Biotechnology (#sc-9104) Dallas, TX 1:200 dilution |

TABLE 4-continued

Antibodies and small-molecule stains validated for cell-phenotyping in PACT- and PARS-processed tissues.

| Label | Supplier and/or Formulation |
|---|---|
| Rabbit anti-parvalbumin antibody | abcam (ab11427) San Francisco, CA<br>1:200-1:400 dilution |
| Mouse anti-β-spectrin II antibody | BD Biosciences (612563) Franklin Lakes, NJ<br>1:200 dilution |
| Rabbit anti-alpha adducin antibody | abcam (ab51130) San Francisco, CA<br>1:200 dilution |
| Goat anti-myelin basic protein antibody | Santa Cruz Biotechnology (C-16: sc-13914) Dallas, TX<br>1:200 dilution |
| Mouse anti-pan-axonal neurofilament SMI-312 antibody | BioLegend Inc. (SMI-312) San Diego, CA<br>1:500 dilution |
| Guinea pig anti-insulin antibody | DAKO (A0564) Carpinteria, CA<br>1:500 dilution |
| Goat anti-somatostatin antibody | Santa Cruz Biotechnology (sc7819) Dallas, TX<br>1:500 dilution |
| Secondary Antibodies[b] | |
| Donkey anti-chicken IgY, available as Cy2[c], Cy3[d], Cy5[e], Alexa Fluor ® 594[f], Alexa Fluor ® 647[g] conjugates | Jackson ImmunoResearch, where ### = fluorophore code, West Grove, PA<br>1:200 dilution |
| Donkey anti-goat available as Cy2[c], Cy3[d], Cy5[e], Alexa Fluor ® 594[f], Alexa Fluor ® 647[g] conjugates | IgG, Jackson ImmunoResearch (703-###-155), where ### = fluorophore code, West Grove, PA<br>1:200 dilution |
| Donkey anti-guinea pig IgG, available as Cy2[c], Cy3[d], Cy5[e], Alexa Fluor ® 594[f], Alexa Fluor ® 647[g] conjugates | Jackson ImmunoResearch (703-###-155), where ### = fluorophore code, West Grove, PA<br>1:200 dilution |
| Donkey anti-mouse IgG, available as Cy2[c], Cy3[d], Cy5[e], Alexa Fluor ® 594[f], Alexa Fluor ® 647[g] conjugates | Jackson ImmunoResearch (703-###-155), where ### = fluorophore code, West Grove, PA<br>1:200 dilution |
| Donkey anti-rabbit IgG, available as Cy2[c], Cy3[d], Cy5[e], Alexa Fluor ® 594[f], Alexa Fluor ® 647[g] conjugates | Jackson ImmunoResearch (703-###-155), where ### = fluorophore code, West Grove, PA<br>1:200 dilution |
| Reagents for FISH Labeling[h] | |
| 20 mer oligo probes towards β-actin | 1 nM per each of 24 Alexa 594 labeled 20 mer oligo probes towards β-actin prepared in hybridization buffer |
| Slowfade Gold + DAPI | Life technologies (#S-36938), Grand Island, NY<br>Mounting media for smFISH samples |

[a] Atto fluorescent dyes that possess an NHS ester moiety (available from Sigma Aldrich) may be conjugated to the primary antibody; this eliminates the need to perform a secondary antibody incubation when imaging tissues via fluorescence microscopy.
[b] Cyanine dyes are traditionally better able to withstand dehydration and embedding in nonpolar, plastic media, whereas DyLight and Alexa Fluor ® dyes are perceived as brighter than Cyanine dyes in aqueous media. Both seem to work well in labeling thick, cleared tissue samples.
[c] Cy2 code: 225
[d] Cy3 code: 165
[e] Cy5 code: 175
f Alexa Fluor ® 594: 585
g Alexa Fluor ® 647N: 605
[h] see Supplementary Methods for protocol

TABLE 5

Troubleshooting PACT and PARS protocols.

| Step | Problem | Potential Cause | Suggested Solution |
|---|---|---|---|
| Transcardial perfusion (Step 3, 5) | Incomplete exsanguination, or absence of tissue stiffening with PFA perfusion | Catheter is not stably placed in heart in order to deliver solutions into rodent vasculature; vasculature was compromised during initial hPBS flush because perfusion rate | Use a single suture (loop thread around aorta) or clip to secure the feeding needle in place at the level of the aortic arch; start the initial perfusion of hPBS at a slower rate, and flush twice the volume of hPBS through. |

TABLE 5-continued

Troubleshooting PACT and PARS protocols.

| Step | Problem | Potential Cause | Suggested Solution |
|---|---|---|---|
| | | was too high; an insufficient amount of hPBS was pushed through vasculature such that blood remains in smaller vessels | |
| Hydrogel monomer (HM) embedding (Step 6) | Tissue damage during clearing, tissue seems unnecessarily fragile | Inadequate infusion of HM solution throughout tissue | It may be necessary to leave large tissue samples such as whole rat organs in hydrogel monomer for >12 hours so that the monomer may fully penetrate the tissue. |
| | | Tissue is structurally fragile or delicate | Consider including PFA (1-4%) in HM formulation for subsequent sample preparations; extend post-fixation step. |
| | Poor HM polymerization after 37° C. incubation | Inadequate degassing | Repeat degassing step (10 min under vacuum, 10 min of nitrogen-bubbling) and 37° C. incubation. |
| | | Bad reagents | Use fresh PFA for fixation; prepare hydrogel monomer solutions immediately before use and store the thermoinitiator, acrylamide and bis-acrylamide stock solutions at 4° C. |
| | Embedded tissue or biological sample is too fragile for non-clearing applications (e.g. thin-sectioning and imaging) | Insufficient density of tissue crosslinking | Increase the concentration of PFA (1-4%) and/or include bisacrylamide (0.05%) in the hydrogel monomer formulation. |
| Tissue clearing (Step 7) | Clearing rate appears to slow down before the tissue is clear | Clearing may slow down as the clearing buffer acidifies | Buffer-exchange the clearing solution. |
| | | Dense crosslinking | If A4P1-4 was used, remove PFA from PACT hydrogel formulation in subsequent experiments; halve the PFA post-fixation incubation. |
| | | Tissue is dense, highly myelinated and/or otherwise difficult to clear | Continue incubating in clearing buffer while checking periodically. Consider PARS clearing rather than PACT clearing for peripheral organ samples as perfusive force accelerates clearing rate. |
| | Tissue appears to degrade | Bacterial contamination | Buffer-exchange the clearing solution, adding 0.01%-0.05% sodium azide to PBS-based clearing solutions. |
| | | Poor hybridization of tissue to hydrogel monomers | In subsequent clearing experiments, prepare the hydrogel monomer solution with fresh reagents, increase the PFA content by 1%, extend the tissue. Incubation in hydrogel monomer by 12-24 h, and/or prior to polymerizing the tissue-hydrogel, perform two rounds of degassing (where one round equals 10 min under vacuum and 10 min nitrogen-bubbling). |
| | | Poor PFA crosslinking of tissues | Ensure that adequate fixation and post-fixation steps are performed; use fresh 4% PFA. |
| | Hydrogel softening during clearing | Overclearing and/or initial poor hydrogel polymerization | Consider doubling the post-fixation step or including PFA in the hydrogel monomer formulation in subsequent experiments; consider underclearing tissue as RIMS |

TABLE 5-continued

Troubleshooting PACT and PARS protocols.

| Step | Problem | Potential Cause | Suggested Solution |
|---|---|---|---|
| | | | incubation will cause translucent tissues to become transparent. |
| | Difficulty obtaining complete bone decalcification | PACT-deCAL procedure requires further optimization by the user according to the bone size and density (guidelines provided are specific to the mouse femur and tibia) | Experiment with EGTA-based chelation and then 8% SDS clearing. Alternate steps for "7(B) PACT-deCAL" are as follows:<br>(i) Incubate bone-hydrogel in 0.1M EGTA in 1 × PBS (pH 9) for 72 h at 37° C.<br>(ii) Rinse sample in 1 × PBS; clear in 8% SDS-PBS (pH 7.4) for 7 days at 37° C., performing 1 buffer exchange during clearing.<br>(iii) Wash sample as usual: 24-48 h in 3-6 buffer changes of 1 × PBS at RT. |
| | | Dense, fibrous bone or larger samples may be resistant to decalcification by chelating reagents and SDS-based clearing alone | Since bone consists of ~16% collagen, consider incubating bone in collagenase before clearing in order to disrupt collagen matrix. |
| | Tissue becomes turbid; white precipitate appears in tissue | Incomplete washing after clearing, causing SDS and/or salts to precipitate in when it is moved from 37° C. to RT | Double the length of all wash steps, making sure to perform several exchanges of 1 × PBS tissue each day; wash with PBST or BBT instead of 1 × PBS |
| | | Tissue becomes white and nearly opaque upon transfer to 4° C. | Salts and, in particular residual SDS will precipitate in tissue if it is moved to 4° C.; however the precipitate should disappear upon gradual warming of tissue to RT or 37° C. Consider performing more extensive wash steps in future experiments, particularly after SDS clearing. |
| | Slight tissue yellowing during clearing | Use of PFA-containing hydrogels or BB | We have not observed adverse effects from slight tissue yellowing on imaging results-tissue becomes clear upon RIMS mounting. However, very occasionally, some samples become very yellow during the first half of SDS clearing: these samples should be cleared for a longer length of time-until very transparent- or the yellowing will cause high background during imaging. Ensure that only fresh PFA is used in subsequent experiments. |
| | Brain does not become transparent during PARS-based clearing | Insufficient perfusion with clearing buffer | Extend the clearing time: most rodent organs clear within 2 days via PARS, however the brain requires an additional 1-2 weeks to clear. RIMS-mounting will also increase the transparency of "translucent" tissues. |
| | A specific organ does not clear well via whole-body PARS | Vasculature becomes compromised during clearing process | Identify and try to fix leakages in the vasculature; if not successful, tie off the major vessels supplying that organ, excise the organ for PACT clearing, and continue to perform PARS clearing with the remaining body. Starting over with a new |

TABLE 5-continued

Troubleshooting PACT and PARS protocols.

| Step | Problem | Potential Cause | Suggested Solution |
|---|---|---|---|
| | | Poor flow to specific organ due to anatomic reasons (poorly vascularized) | PARS preparation should only be used as the last resort. If PACT is not a desirable option and the organ is sizable with accessible vasculature consider PARS clearing the single organ, akin to published decellularization methods. |
| Histology (Step 9) | Poor Labeling, including faint signal | Shallow antibody penetration | Increase the antibody concentration in the primary antibody cocktail; or, replenish the antibody half-way through extended incubations, by either adding additional antibody directly to the original antibody cocktail, or preparing a fresh antibody dilution. |
| | | Incomplete delipidation, which obstructs labeling | Increase the clearing time. |
| | | High crosslinking density | High crosslink density in A4P1-4-hybridized tissues will slow antibody diffusion-thus antibody incubations should be extended. |
| | | Epitope loss or epitope masking (unlikely if adhering to protocol) | If tissue was damaged due to microbial contamination, consider adding 0.01%-0.05% sodium azide to all buffers/solutions that are used in long incubations; over-fixation may lead to antigen masking-thus decrease post-fixation steps. |
| | | Poor quality of antibody or of dye, which results in weak labeling | Only use high-quality antibodies that have been first verified in standard thin-section immunolabeling; experiment with a different antibody supplier-different antibodies against the same target may vary greatly in their labeling abilities, such as in their binding affinity and in their capacity to access intracellular compartments for cell-filling labeling versus only superficial/extracellular epitope-binding. Finally, it can be helpful to simultaneously prepare a thin section (40-100 um) alongside a thick, cleared section while troubleshooting to ensure that the visualization of a strong signal is possible. |
| | High background and/or autofluorescence | Tissue damage during processing | Review procedure carefully, ensure that no reagents introduced bacterial contamination of sample; lengthen wash steps to remove potential precipitate (SDS, donkey serum-antibody immunocomplexes). |
| | | Sources of autofluorescence-part 1: fixative-induced autofluorescence, elastin, collagen | Many standard histological techniques for reducing autofluorescence, such as tissue bleaching, performing wash steps in PBST containing 100 mM glycine to quench aldehydes, and treating tissue with histology stains that quench or mask autofluorescence, may be |

TABLE 5-continued

Troubleshooting PACT and PARS protocols.

| Step | Problem | Potential Cause | Suggested Solution |
|---|---|---|---|
| | | | adapted to thick-sectioned cleared tissues-typically by performing longer wash steps after the appropriate countermeasure; photobleaching tissue prior to IHC at wavelengths that exhibit the highest autofluorescence may also help. |
| | | Sources of autofluorescence-part 2: heme chromophores, lipofuscins | Thoroughly remove all blood during initial cardiac perfusion; to elute heme, incubate hydrogel-embedded PACT sections and in particular PACT-deCAL sections in CUBIC reagent-1 for 12-24 hours at 37° C. with shaking, then transfer sections directly into 8% SDS for clearing; lipofuscin autofluorescence is partially combatted by tissue clearing, however thick tissue sections may be incubated in 0.2% to 1.0% Sudan Black B for 1-3 hours immediately prior to Step 5 (PACT hydrogel-embedding) in order to reduce high autofluore scent background-tissue clearing will allow Sudan Black B-treated sections to become sufficiently transparent for imaging (see FIG. 12). |
| | High background, but with high signal of correctly labeled epitopes | Nonspecific antibody binding | Extend the wash steps after both primary and secondary antibody incubations an additional day, performing 4-5 buffer exchanges each day, and wash samples in PBST instead of 1 × PBS; in rodent tissue samples, avoid using antibodies that require anti-mouse secondary antibody labeling; also some chicken antibodies show strong staining with high background and/or aggregation-these antibodies should be diluted to 1:400-to-1:1000. |
| Tissue mounting and imaging (Steps 12-13) | Poor image quality and/or poor imaging depth | Tissue is of insufficient transparency for light to penetrate | Extend the tissue incubation time in RIMS to several days before imaging; for bone, incubate for an additional 1 day in RIMS-1.48 or RIMS-1.49 before imaging. |
| | Morphological distortion | Tissue size fluctuations | Immediately prior to RIMS incubation, post-fix cleared, immunolabeled tissue in 4% PFA for a few hours at RT, then wash and incubate in RIMS for at least several days to one week before imaging; consider preparing future samples in hydrogel that contains PFA (e.g. A4P1-A4P4, depending on the degree of swelling) and/or consider a longer post-fixation step after transcardial perfusion. |
| | Bubbles in mounted tissue | Air trapped in tissue or dissolved air in RIMS; sample mounted with insufficient RIMS, | Purge RIMS of excess air via degassing the tissue in fresh RIMS prior to mounting (e.g. using the vacuum line, akin to |

TABLE 5-continued

Troubleshooting PACT and PARS protocols.

| Step | Problem | Potential Cause | Suggested Solution |
|---|---|---|---|
| | | causing the introduction of air bubbles between the RIMS meniscus and coverglass. | the hydrogel polymerization of step 5; do NOT bubble nitrogen through the sample following its placement under vacuum)-use this degassed RIMS to mount the degassed sample. |
| | Sample appears turbid or white | RIMS-mounted sample was placed at 4° C., causing salts/etc. to precipitate | The precipitate should disappear upon gradual warming of tissue to RT or 37° C. Store RIMS-mounted tissue at RT, protected from light, OR mount tissue in cRIMS for cold storage. |
| 3D Image Analysis (steps 15-17) | Imaging software and/or computer crashes; unable to load acquired images | Large images do not fit in RAM | Troubleshoot with a different option in the step 15 workflow: option A using Imaris, option B using TerraStitcher, or option C Vaa3D TerraFly; consider upgrading computer workstation and/or adding RAM and/or new graphics card; down sample the data set (of note, compression cannot be used with Imaris); process the images in tiles (i.e., analyze each tile individually). |

Supplementary Methods
AAV9 Tropism Studies (FIG. 1A-E)

$1\times10^{12}$ vector genomes of AAV9:CAG-GFP-2A-Luc-WPRE-SV40 late poly A (AAV9:CAG-GFP) were administered systemically (via retro-orbital injection) to 6-week-old female C57Bl/6 mice. Three weeks later, mice were perfused and cleared via PARS, and individual organs were harvested and equilibrated in RIMS until clear (up to 7 days) before mounting in fresh RIMS and imaging.

Experiments on vertebrates must conform to all relevant governmental and institutional regulations. Animal husbandry and all experimental procedures involving mice and rats were approved by the Institutional Animal Care and Use Committee (IACUC) and by the Office of Laboratory Animal Resources at the California Institute of Technology.

Quantification of Ab Penetration Through PACT-Cleared Tissues (FIG. 4B-D)

Mouse coronal slices, 1 mm thick cleared with PACT conditions as stated and stained with anti-parvalbumin antibody and DAPI, were used to analyze the rate of diffusion of antibodies and small molecule dyes through cleared tissue. A column through the depth of the tissue was imaged on a Zeiss LSM 780 confocal with the Plan-Apochromat 10×0.45 N.A. M27 air objective (w.d 2.0 mm). Measured image intensities in each channel for each z-section were scaled to correct for varying laser power and yield an estimate of fluorescence. Image stacks were manually cropped (in z) to include only the "upper half" of the tissue section nearest the imaging objective and (in xy) to exclude areas where the top tissue surface was curved, an effect sometimes observed as tissue expands while clearing.

Quantitative image analysis was carried out using a custom MATLAB script. To factor out attenuation loss along the z-axis and account for varying cell density, the antibody fluorescence signal was scaled by the average DAPI intensity and computed perpendicular to the tissue surface to estimate labelling intensity as a function of depth. To fit this signal, we first identified the location of the surface as the point of maximum staining level and the center of the section as the point of minimum staining level. Since the surface is not perfectly flat, we excluded the top 20 µm above the maximum point of the signal from further analysis. Data points plotted in FIG. 4D show the staining level starting 20 µm below the maximum down to the minimum staining level.

To provide a quantitative estimate of diffusion, we fit an exponential model (appropriate for idealized steady state of diffusion-decay into an infinite half-space with fixed boundary concentration) with an additive term to account for background fluorescence:

$$f(x)=a^*\exp(-\text{tau}^*x)+b$$

where the exponent tau is inversely proportional to the square-root of the diffusivity (larger tau=>slower diffusion). If the staining level followed this model we would expect to see linear decay with depth on the semi-log plots shown in FIG. 4D. We observe that staining levels near the surface of the tissue fall below an exponential model (likely due to post stain washing). Similarly, signal near the center of the tissue, where staining is ~1% the level observed on the surface is noisy (e.g., due to imaging noise, stochastic fluctuations at low concentration, not reaching steady state). Therefore we used staining level between 20% and 80% depth to fit the exponential model (this range is indicated by the extent of the straight lines for each sample shown in FIG. 4D).

Cleared Tissue Preparation for Electron Microscopy and Tomography (FIG. 5B)
Background To incorporate high-resolution, subcellular information into lower-resolution tissue maps requires performing correlative studies between light microscopy (LM) and electron microscopy (EM) datasets. While the tandem preparation of individual thin tissue slices for both LM and EM analysis is relatively commonplace, not until recently have scientists envisioned applying this approach to a large spatial extent, such as whole organs. Despite the obvious challenge in reconstructing tissue architecture from nanoscale tiles, this is currently the only viable method for creating comprehensive wiring diagrams. Neither light-microscopic observations nor the (statistical extrapolation) mathematical inference of cellular connectivity can provide high resolution circuit maps with sufficient statistical certainty. Instead, cellular structures and synaptic contacts must be visualized first-hand in order to create valid tissue reconstructions.

Herein, one could envision a cell-mapping methodology in which large tissue blocks were first scanned via LM, and then sub-sectioned for EM analysis. While the former is easily completed by imaging through cleared tissue blocks, the latter faces a few technical challenges. Namely, lipid-extracted tissues make poor subjects for high-resolution EM studies. A fundamental component of tissue clearing, delipidation compromises the structural integrity of remaining subcellular constituents and eliminates a primary source of ultrastructural contrast in EM (i.e., osmium tetroxide based fixation-staining of lipids, and thus of all cell membranes and membrane-enclosed organelles). Without this contrast, the process of identifying fine structures or tracing cellular elements between images, assuming they survive clearing, becomes problematic.

A second concern in the translation of cleared tissues to EM is their method of preparation. Traditionally, tissue that is slated for ultrastructural analysis undergoes a highly regimented fixation, freeze-substitution, and/or immunostaining process to ensure that the subcellular architecture is well-preserved for high-resolution visualization and reliable immunolocalization. The tissue clearing procedure departs from standard EM methods even at its onset: tissues are initially fixed in 4% PFA with no inclusion of glutaraldehyde, a staple in EM fixatives. Similarly, extended incubations at RT-to-37° C. in solutions where pH and osmolarity are imprecisely controlled, are suboptimal conditions for the preservation of fine structures.

Cognizant of these impediments, we hypothesized that ultrastructural analysis of cleared tissue samples through transmission electron microscopy (TEM) would still provide relevant data on the degree of lipid extraction within different samples. By comparing the fine structural preservation in control, A4P0-embedded, and A4P4-embedded tissues, we might make inferences on slight difference in clearing efficiency and hydrogel-based retention of tissue components that are not readily apparent by eye or by LM.

Experimental Methods

Brain tissue samples from each of the clearing conditions were processed simultaneously for subcellular examination via electron tomography. Each sample was placed in a petri dish containing 0.1 M sodium cacodylate trihydrate+5% sucrose. Similar regions were extracted from each sample and cut into 0.50-0.75 mm cubes. These pieces were placed into a brass planchette (Ted Pella, Inc.) prefilled with cacodylate buffer supplemented with 10% Ficoll (70 kD; Sigma-Aldrich) which serves as an extracellular cryoprotectant. The sample was covered with second brass planchette and rapidly frozen with a HPM-010 high-pressure freezer (Leica Microsystems, Vienna), then stored in liquid nitrogen.

Planchettes containing vitrified samples were transferred under liquid nitrogen to cryotubes (Nunc) filled with 2.5% osmium tetroxide, 0.05% uranyl acetate in acetone. Tubes were placed into an AFS-2 freeze-substitution machine (Leica Microsystems) and processed at −90° C. for 48 hours, warmed slowly over 12 hours to −20° C. and further processed at that temperature for 10 hours. The tubes were then warmed to 4° C. for 1 hour and the samples rinsed 4× with cold acetone. Samples were removed from the planchettes, infiltrated into Epon-Araldite resin (Electron Microscopy Sciences, Port Washington Pa.) and flat-embedded between two Teflon-coated glass microscope slides.

Embedded samples were observed with a phase-contrast light microscope and similar portions from each condition was extracted and glued to plastic sectioning stubs. Semithick sections (350 nm) were cut with a UC6 ultramicrotome (Leica Microsystems) and a diamond knife (Diatome-US, Port Washington Pa.). Sections were placed on Formvar-coated copper/rhodium slot grids (Electron Microscopy Sciences) and stained with 3% uranyl acetate and lead citrate. Colloidal gold particles (10 nm) were placed on both sides of the grid to serve as fiducial markers for tomographic image alignment. Grids were placed in a 2040 dual-axis tomography holder (E.A. Fischione Instruments, Inc., Export Pa.) and imaged with a TF30-ST electron microscope at 300 KeV. Montaged overviews and tomographic tilt-series were acquired automatically using the Serial-EM software package. Samples were tilted +/−64° and 2 k×2 k images recorded at 1° intervals with a XP1000 CCD camera (Gatan, Ltd.). Image data was processed and analyzed using the IMOD software package on a MacPro computer (Apple, Inc.).

Anticipated Results

The control sample of this experiment was fixed only by 4% PFA perfusion, akin to cleared samples, and then processed for TEM. Its retention of fine structure was readily apparent (see FIG. 5B, Control), and the level of gross tissue damage was minimal considering the nontraditional method of preparation. Significantly less fine structure was discernable in the cleared samples, as was predicted, and the lipid-containing membranes were fully solubilized or highly ruptured. Of note, the addition of paraformaldehyde to hydrogel formulations served to attenuate lipid extraction and led to greater preservation of neuronal processes (see FIG. 5B, A4P4).

These results highlight the potential for incorporating EM analysis into tissue clearing and LM experiments. A modified perfusion followed by a more aggressive post fixation and/or freeze-substitution might offer some ultrastructural stabilization that persists through clearing. Herein, it would be possible to carry uncleared control samples through to high-resolution tomographic studies, while matched samples were processed for clearing and LM.

Pre-PACT Tissue Staining to Mask Autofluorescence (FIG. 12)

Background

The following protocol summarizes how tissue stains used in traditional histology, and in particular, stains used to quench lipofuscin-derived fluorescent artifacts, may be incorporated into the PACT protocol. Representative results are presented in FIG. 12.

Autofluorescent artifacts and high background pose a greater threat to imaging through thick tissue than through thin sections as they significantly decrease the signal-to-noise ratio, making the distinction between specific labeling and nonspecific autofluorescence difficult. Among the most common causes of autofluorescence in tissue are tissue-aldehyde adducts from aldehyde-based fixatives and catecholamine, collagen, elastin, the heme chromophore, and degradation products of red blood cells (i.e., the lipid peroxidation and protein glycation aggregates, such as lipofuscin, that can accumulate in aging red blood cells). For biological researchers, the latter source of autofluorescence becomes a major concern when working with tissue samples from aged subjects (e.g., old laboratory animals) or with poorly perfused, overfixed samples (e.g. post-mortem or biopsied human tissue). Herein, a few tissue stains, most notably Sudan Black B and cupric sulfate, have been found to mask lipofuscin-like autofluorescence in the histological preparation of thin-sectioned (<0.5 mm) tissues. Thus, we endeavored to test their compatibility with thick, PACT-cleared rodent brain sections (see FIG. 12) according to the experimental methods detailed below.

Reagents
1. Perfusion-fixed (4% PFA) 0.5-1 mm coronal brain slices from Thy1-YFP mice
2. Sudan Black B (Sigma-Aldrich, cat. no. 199664)
3. Ethanol (Sigma-Aldrich, cat. no. E7023; or Fischer Scientific, cat. no. BP2818)
4. Cupric Sulfate (Fisher Scientific, cat. no. 525285A)
5. Ammonium Acetate (Sigma-Aldrich, cat. no. A1542)
6. PACT Hydrogel Monomer (HM) solution (A4P1)
7. PACT Clearing solution: 8% SDS-BB (pH 8.5)
8. Optional: PACT IHC reagents and IHC buffer
9. Refractive Index Matching Solution (RIMS, RI=1.47)
10. 1× Phosphate-buffered saline (1×PBS), pH 7.4
11. 1×PBS with 0.1% (vol/vol) Triton X-100 (PBST)
12. 0.1 M Phosphate buffer (PB), pH 7.4
13. Sodium azide (Fisher Scientific, cat. no. 71448-16)
14. Distilled and deionized water (dd H20)

Equipment
1. Syringe filters (Corning, cat. no. CLS431218)
2. 30 ml Luer-Lok syringes (BD, cat. no. 302832)
3. Hydrogel polymerization equipment and supplies
4. PACT equipment and supplies
5. Sample mounting equipment and supplies Reagent Set-Up
1. Cupric sulfate lipofuscin treatment (CuSO4): Prepare 10 mM cupric sulfate in 50 mM ammonium acetate (CH3COONH4) buffer; adjust the pH=5.0.
2. Sudan Black B lipofuscin treatment (SB): Prepare 0.2% Sudan Black B in 70% ethanol in a sealable container or jar; protect from light. Alternatively, if tissue possesses a high level of lipofuscin, or if tissue will undergo extensive immunolabeling, which can wash off SB staining, prepare 1% SB in 70% ethanol. With the container sealed and wrapped in tin foil, stir the SB solution on a stir-plate at high-speed for 2 hours (or up to overnight). Syringe-filter the SB solution two times and use immediately.

Experimental Methods
Thy1-YFP mice were perfusion-fixed with 4% PFA, and the excised brains were cut into 0.5 mm and 1 mm coronal sections. Upon brief post-fixation, sections were rinsed in 1×PBS and then dd H2O, and then incubated in either 1×PBS (control), 10 mM CuSO4, 0.2% SB, or 1% SB for 2-3 hours at RT with shaking. Sections were then dipped in dd H2O to remove excess stain, briefly rinsed in 1×PBS, and incubated in A4P1 for 48 hours at 4° C. before hydrogel polymerization according to standard PACT procedures. CuSO4 but not SB seemed to interfere with polymerization, as the hydrogel did not fully set. A4P1 sections (see FIG. 12A) were then cleared in 8% SDS-BB (pH 8.5), with all 0.5 mm sections (see FIG. 12B) and the control 1 mm section (see FIG. 12C) becoming translucent after ~12-15 hours. The CuSO4-treated and SB-treated 1 mm sections required an increased (~24-48 hours) time to clear in comparison to the control (see FIG. 12C). All sections were immunostained for parvalbumin (Cy5-conjugated secondary IgG) according to the standard PACT IHC protocol and transferred to RIMS for 24 hours (see FIG. 12B-C), followed by degassing and RIMS-mounting. 0.5 mm thick sections were imaged on a Zeiss LSM 780 confocal with the Plan-Apochromat 10×0.45 N.A. M27 air objective (w.d 2.0 mm) to independently measure the emission profiles generated by excitation with the 561 nm laser (filter bandpass for rhodamine/Cy3) versus by the 488 nm and 633 nm lasers, using filters for YFP and Cy5 fluorescence, respectively.

Anticipated Results

In these experiments, we aimed to assess whether SB or CuSO4 tissue pretreatment could reduce autofluorescent background in brain tissue without masking endogenous fluorescent proteins and immunofluorescent labels (YFP, Cy5-conjugateded secondary antibody). The emission spectra generated by the YFP and Cy5 fluorophores were compared to the autofluorescence spectra within the orange to red wavelengths (rhodamine/Cy3 filter), where the absence of any specific labeling would allow us to clearly observe fluorescent artifacts. The resulting imaging data, which are presented as 500 μm thick maximum intensity projections (MIP) over the cortex for each treatment condition (see FIG. 12D, top row), demonstrate that neither SB nor CuSO4 treatments prevented the visualization of YFP and Cy5 fluorophores (and DAPI, data not shown) in thick cleared sections. Both treatments were effective in reducing autofluorescent background and masking the fluorescence of lipofuscin-like deposits, as shown in the duplicate MIPs for the fluorescence emission collected using the rhodamine/Cy3 bandpass filter (see FIG. 12D, bottom row).

To investigate whether the potential for deep imaging was retained after 0.2% SB treatment (see FIG. 12C), a 1.0 mm thick section was imaged for YFP and Cy5 fluorescence through its entire thickness within a cortical region (see FIG. 12E, left), and a 100 μm thick MIP (see FIG. 12E, right) was generated in order to display the endogenous fluorescence and staining that is visible at depth. While endogenous YFP fluorescence is very bright and of almost uniform intensity throughout the slice, which speaks to the efficacy of PACT clearing in A4P1-embedded slices, immunolabeling intensity suffers at depth, and requires adjustment of signal intensity or laser power for visualization.

ePACT: a Protocol for Enhanced Clearing via Expansion (FIG. 13)

Background

The following protocol, termed ePACT for expansion-enhanced PACT, details the experimental methods used to prepare the cleared and expanded brain sections pictured in FIG. 13.

Reagents
1. Perfusion-fixed 100 μm rodent brain slices
2. (optional) PACT IHC reagents
3. 40% Acrylamide (40% wt/vol; Bio-Rad, cat. no. 161-0140)
4. 2% Bis-acrylamide (2% wt/vol; Bio-Rad, cat. no. 161-0142)
5. Sodium acrylate (Sigma-Aldrich, cat. no. 408220)
6. Sodium chloride (NaCl) (Sigma-Aldrich, cat. no. S5886)
7. 1×PBS
8. 4-hydroxy TEMPO (Sigma-Aldrich, cat. no. 176141)
9. N,N,N',N'-Tetramethylethylenediamine (TEMED, Sigma-Aldrich, cat. no. T9281)
10. Ammonium persulfate (APS, Sigma-Aldrich, cat. no. A1542)
11. Boric acid (Sigma-Aldrich, cat. no. B7901 or B6768)
12. Sodium hydroxide pellets (EMD, cat. no. SX0590-3)

13. Sodium dodecyl sulfate (Sigma-Aldrich, cat. no. L3771) or 20% SDS solution in water (Sigma-Aldrich, cat. no. 05030)
14. 10×PBS
15. Collagenase, crude from *Clostridium histolyticum* (Sigma-Aldrich, cat. no. C0130)
16. Calcium chloride (Sigma-Aldrich, cat. no. C1016)
17. TES (Sigma-Aldrich, cat. no. T5691)
18. distilled/deionized water (dd H2O)
19. Agarose, low melt temperature (Research Products International Corp., cat. no. 9012-36-6)
20. Sodium azide (Fisher Scientific, cat. no. 71448-16)
21. Clear nail polish or Entellan (Electron Microscopy Sciences, cat. no. 14800)

Equipment
1. For hydrogel-embedding: 0.2 mm and 0.5 mm spacers (iSpacer, SunJin Lab Co, cat. no. IS001, IS002), or HybriWell™ Sealing System (GRACE Bio-Labs, cat. no. 611103, 611104, 612106 (select based on sample size and number))
2. (optional) Spacers for enzymatic digestion and/or mounting, order based on sample size): 0.5 mm or 2.5 mm spacers (Silicone Isolator, Electron Microscopy Sciences; or GRACE Bio-Labs), or silicone rubber sheet (any, such as: Press-to-Seal™ Silicone Sheet with Adhesive, Fischer Scientific, cat. no. P-24745)
3. Clear nail polish or Entellan (Electron Microscopy Sciences, cat. no. 14800)
4. Microscope slides (Thermo Scientific, cat. no. 10143352; VWR, cat. no. 48382-173; Brain Research Laboratories, cat. no. 5075-plus)
5. Cover slips (VWR, cat. no. 48404-452, 16004-344, 16004-322; Brain Research Laboratories, cat. no. 4860-1-½)
6. ePACT sample washing and clearing wells, such as 6-well tissue culture plates and/or petri dish
7. Slide humidifier (we use a petri dish with lid containing a moistened Kimwipe)
8. 37° C. incubator or warm-room, with a nutating mixer inside
9. Tools for sample handling (forceps, natural-bristle paintbrush, tweezers: Fine Science Tools; lab spoons, spatulas: any, such as Sigma-Aldrich, cat. no. Z511455)
10. Eppendorf tubes (0.5, 1.5, 2.0 ml volumes)

Reagent Set-Up
1. ePACT acrylate-acrylamide copolymer (AcAm): Combine 2.5% acrylamide, 8.625% sodium acrylate, 0.15% bis-acrylamide in 1×PBS with 2 M NaCl; store at −20° C. prior to use. For tissue embedding, thaw AcAm on ice, and add the following (w/w): 0.01% 4-hydroxy TEMPO, 0.2% TEMED, and 0.2% APS (see FIG. 13D)
2. 0.01 M Phosphate-buffered Saline (PBS): Combine 8 g NaCl, 0.2 g KCl, 1.42 g Na2HPO4, 0.245 g KH2PO4 in distilled H2O (dH2O) to a total volume of 1 L; pH to 7.4, sterile filter or autoclave, and store at 4° C. Alternatively, purchase 1×PBS mix (Sigma Aldrich, cat. no. P5368) or pre-made solution (Lonza, cat. no. 04-409R) from a commercial supplier; adjust the final pH when necessary.
3. Boric acid buffer (BB): Prepare a 1 M boric acid buffer stock solution through stirring 61.83 g boric acid and 10 g NaOH in 900 ml water with gentle heating. Once sodium hydroxide pellets and boric acid are fully dissolved, adjust the pH to 8.5 with NaOH and add distilled and deionized water (dd H2O) to a total volume of 1 L. Dissolve this stock 5-fold for 0.2 M boric acid buffer (BB). To make a boric acid wash buffer (BBT, 0.2 M boric acid buffer with 0.1% Triton X-100 (vol/vol), pH 8.5), dilute the 1 M boric acid stock to 0.2 M boric acid in dd H2O, adding 1 ml of Triton X-100 per liter of BBT.
4. ePACT Clearing solution: For borate-buffered 10% SDS in 0.2 M BB at pH 8.5 (10% SDS-BB), dilute 500 ml 20% SDS and 200 ml 1 M boric acid buffer stock to 1 L with dd H2O; adjust the pH to 8.5, if necessary.
5. TESCA buffer: Prepare 50 mM TES, 0.36 mM Calcium chloride solution, pH 7.4; sterile filter and store at RT.
6. ePACT Digestion solution: 10 mg/mL collagenase in TESCA buffer, prepared fresh
7. Mounting media: 2% low-melt agarose. Expanded samples may be stored at RT for ~72 hours prior to imaging if 0.01% sodium azide is added to the melted agarose solution immediately prior to pouring, and if the cover-slipped sample is sealed with Entellan.

Procedure
The following steps have been optimized for clearing and expanding 100 μm thick rodent brain slices (from wild type rats, Thy1-YFP mice). To perform IHC with full-format antibodies prior to clearing, the tissue must be thoroughly permeabilized to obtain the best results. We suggest freezing in OCT medium, cryotome-sectioning to 100 μm, and performing IHC on free-floating sections according to standard protocols. Alternatively, the post-fixed mouse whole-brain may be vibratome-sectioned to 100 μm thick slices and permeabilized with ≤1% Triton X-100 (1 hour, RT with shaking). Without freeze-thaw permeabilization, antibody labeling may be weaker, and one may encounter difficulties expanding larger tissue samples (e.g., coronal rat brain slices) several-fold without some tissue damage.

Sample Preparation
1. Perfusion-fix the rodent with 4% PFA; excise and post-fix the brain overnight.
2. Prepare 100 μm thick tissue samples via sectioning on cryotome (option A, recommended for most samples) or on vibratome (option B, recommended for rapid visualization of endogenously-labeled small samples such as mouse coronal brain sections).

(A) Sample Preparation via Cryotome-Sectioning
  (i) Cryoprotect the sample in 30% sucrose at 4° C. with shaking; incubate until the sample sinks.
  (ii) Tissue-off the sample, submerge the sample in OCT medium for <5 minutes in a plastic tissue mold, and then snap-freeze in an isopentane-dry ice slurry.
The sample may be stored at −80° C. for up to a few months.
  (iii) Cryotome-cut the frozen sample, collecting sections in PB.
  (iv) Thaw and rehydrate free-floating sections in PB for 20 min at RT to remove OCT medium.
  (v) Permeabilize sections for 1 hour at RT in PBST containing 0.1%-1.0% Triton X-100 and 100 mM glycine; then, rinse in 1×PBS.
Sections may be stored at 4° C. in 1×PBS with 0.01% sodium azide for ~1 day.

(B) Sample Preparation via Vibratome-Sectioning
  (i) Cut 100 μm thick tissue sections on the vibratome according to manufacturer's instructions.
  (ii) Collect sections free-floating into 1×PBS.
  (iii) Permeabilize sections for 1-2 hours at RT in PBST containing 0.1%-1.0% Triton X-100 and 100 mM glycine; then, rinse in 1×PBS.
Sections may be stored at 4° C. in 1×PBS with 0.01% sodium azide for ~1 day.

3. (Optional) Label free-floating tissue sections according to standard IHC protocols. Antibody incubations should be conducted for 24 hours at 4° C. Perform wash steps in PBST. The final wash should be conducted in 1×PBS.

4. (Optional) Image the pre-expanded sample. The section may be mounted on a non-treated glass slide in PB in order to visualize gross tissue morphology and, if applicable fluorescent signal strength. For finer visualization, incubate the section in RIMS for 1-2 hours prior to imaging. After imaging, wash RIMS-infused samples in 1×PBS (3×15 minutes).

ePACT Hydrogel Embedding

5. Thaw ~400 µl AcAm per 1 rat brain section or per 2 mouse brain sections. Add 4-hydroxy TEMPO, TEMED, and APS to half the thawed AcAm in an Eppendorf tube(s) on ice.
6. Immediately transfer the tissue sections into the Eppendorf tube(s) using a paintbrush. Tap the tube(s) to mix, ensuring that the samples are fully submerged in AcAm, and incubate at 4° C. with gentle shaking for 20-30 minutes (depending on the sample size).
7. Place a prepared slide (with a 0.2 mm iSpacer well, or similar alternative) in a petri-dish humidifier (see FIG. 13D, lower left) and pre-chill at 4° C.
8. Add 4-hydroxy TEMPO, TEMED, and APS to the second half of the thawed AcAm in an Eppendorf tube(s) on ice.
9. Transfer the tissues by paintbrush from the Eppendorf to the chilled slide. Pipette the fresh AcAm solution onto the tissues in the iSpacer well, and smooth out the tissues, removing any bubbles that form. Coverslip, and return the sample+petri-dish humidifier to 4° C. for an additional 20-30 minutes.
10. Then, incubate the sample+petri-dish humidifier at 37° C. until the AcAm gel has polymerized (2-4 hours). Ensure that the Kimwipe in the humidifier stays moist during this incubation.
11. (Optional) The AcAm-embedded and polymerized sample may be imaged while it is thus mounted before continuing on to step 12.

ePACT Tissue Clearing

12. Using a razor blade or scalpel, cut around the tissue-hydrogel and carefully remove excess gel. It is important that extra gel be removed or the expanded tissue is very difficult to handle. Slice around the outline of the tissue with the scalpel blade, and carefully roll away the excess gel with a paintbrush. Do not try to remove gel from the flat surface of the brain.
13. Now, carefully remove the AcAm-embedded sample from the slide, and transfer to a sample dish containing 10% SDS-BB (pH 8.5). It is important to handle the tissue with care. Pipette ~0.5 ml clearing buffer onto the sample, and gently slide the paintbrush bristles between the glass slide and sample in order to loosen the AcAm gel's adhesion to the slide. Then, use a spatula to transfer the section between the slide and clearing dish.
14. Clear the tissue overnight at 37° C. with gentle shaking (i.e. on an orbital shaker or nutating mixer placed inside a 37° C. incubator or warm room).
15. Once clear, rinse the sample in BBT and then TESCA buffer for 1-5 minutes each at 37° C. We have found that 6-well plates work well for this process. The tissue may be cleared in ~5 ml 10% SDS-BB (pH 8.5) in the first well, and the next day, transferred into the adjacent well for washing in 5 ml BBT, and then transferred to the adjacent third well for washing in TESCA buffer.
16. Digest the sample in 10 mg/ml collagenase in TESCA buffer for 12-24 hours (i.e. all day for small samples, or all-day and overnight). The tissue should be fully saturated in digestion buffer, however to conserve reagents, it is not necessary to fully submerge the tissue in excess collagenase solution. Small sections (mouse coronal slices) may be transferred back into an iSpacer well (0.5-1 mm) for digestion; coverslip the sample and digest in a petri dish humidifier at 37° C., as in steps 9-10. Larger sections (rat coronal slices) require more space. Transfer these sections into a clean well of a 6-well plate, saturate in digestion buffer (~0.5 ml), parafilm-seal the well/plate, and digest at 37° C. Alternatively, samples may be digested within a larger sample well cut from a silicon matte and adhered onto a slide (see FIG. 13D); coverslip and digest within a petri dish humidifier at 37° C.

Expansion-Based Clearing

17. Soak the digested tissue in dd H2O. This may be accomplished via placing a large, clean slide on the bottom of the petri dish, transferring the section onto the slide, and filling the petri-dish with dd H2O. Incubate in dd H2O at RT and protect from light for 3×15 minutes, or until expanded.

Imaging

18. Mount the tissue-hydrogel for imaging.
The AcAm-embedded section must be mounted in, for example agarose, to prevent sample drift during imaging. Also, the mounted sample must be sealed between the coverslip and glass slide so that the water content of the agarose and of the expanded AcAM tissue-hydrogel remains at a steady-state. Otherwise, the sample will shrink from dehydration and/or expand when it absorbs water from the agarose (i.e. if placed in a humidity chamber).
19. Prepare 2% agarose in dd H2O; cool solution until luke-warm and then add 0.01% sodium azide, if desired, for RT storage up to ~72 hours prior to imaging.
20. Pipette excess dd H2O out of the petri-tissue containing the expanded sample and slide.
21. Center the sample on the large slide (within the petri-dish), and tissue away remaining dd H2O with a Kimwipe.
22. Place a large coverslip on the sample without introducing air bubbles.
23. Pour 2% agarose onto one side of the slide, and allow the agarose to flow by capillary action between the slide and coverslip, encasing the sample. Continue pouring agarose until the sample is fully encased and there is no airspace between the slide and coverslip.
24. Once the agarose has set, use a razor blade or scalpel to slice along the coverslip edge and remove excess agarose.
25. Thickly paint Entellan or nail polish around the edge of the coverslip along the wall of agarose. This should seal the space between the slide and coverslip so that now air can seep into the agarose-mounted sample. This step is crucial. No water must be able to enter or leave the agarose+sample, or the sample's shape and size will fluctuate slowly during imaging. The water absorbed by the acrylate mounted sample must be at steady-state.
26. Once the seal is dry, vacuum grease may be used to reinforce the seal.
27. Image the cleared sample; if necessary, samples may be stored short-term at 4° C.

Anticipated Results

Tissue size fluctuations can place undue stress upon cellular architecture, causing concern about utilizing tissue clearing procedures like ePACT. Indeed, we provide conclusive evidence that fine processes are compromised with unchecked expansion (see FIG. 13A-B, item 3). However, we have also found that tissue swelling may be used to great advantage in certain applications. As an example, certain cell populations are difficult to study due to their high density. To determine virus infectivity for AAV vector engineering or the expression level and coverage of an optogenetic construct, accurate and time-intensive cell-counting must often be performed in discrete tissue regions. For dense cell populations, such as the dopaminergic neurons of the ventral tegmental area and substantia nigra pars compacta, or the cells in the dentate gyms, it may become difficult to distinguish and count fluorescently-labeled cells by hand, and the overlap of labeled cells makes automation of this process nontrivial. Finally, for circuit mapping according to the newly developed neuronal positioning system (NPS)[21], complications arise when there is spatial overlap of fluorescent NPS vesicles at the cell soma or poor spectral separation between NPS vesicles and endogenous Brainbow[22] labeling; the resolution and fluorescence intensity detection offered by confocal microscopy can be insufficient for positive cell identification and accurate projection tracing in these scenarios. The ePACT procedure, by clearing tissue through both SDS-based lipid removal and RI homogenization, can greatly assist in these circumstances. With respect to the latter, enzymatically digesting and inflating the tissue with water, such that proportionally less tissue volume is occupied by heterogeneous cellular components, serves to optically clear the tissue as well as to dilute the fluorescent, nonspecific and/or background signal. In turn, fluorescently labeled targets come into view (see FIG. 13A-B, items 1 and 2), and automated cell counting becomes possible.

Whereas FIG. 13 demonstrates that the ePACT technique is applicable to the "microscale" study of cellular morphology and cell populations, we believe that an additional future value lays in the nanoscale measurement of fluorescent probes in smFISH experiments. Our previous research revealed that, even with the 1.5× expansion conveyed by standard PACT, single labeled transcripts were more readily discernable in PACT tissue than in the customary thin sections due to both lower background and their expansion-based separation. Instead, by utilizing the 4× tissue expansion conferred by ePACT to further enlarge the optical space within a cell (see FIG. 13C), quantitative analysis of multiple transcripts isolated to their subcellular locations can be more easily performed.

TABLE 6

Troubleshooting ePACT

| Step | Problem | Potential Cause | Suggested Solution |
|---|---|---|---|
| Expansion | The section ripples or puckers while expanding | Collagenase digestion was insufficient | Rinse the section in TESCA, and repeat step 16. Prepare fresh collagenase to ensure full enzyme activity, and replace collagenase digestion buffer with fresh, halfway through the digestion |
| | The sections begins to crack during expansion | Insufficient clearing, such that collagenase cannot access all tissue during digestion | Transfer the section back to 10% SDS-BB (pH 8.5) and clear for several hours as in steps 13-15. If tissue begins to expand evenly during washing-proceed to step 17. If not, repeat the collagenase digestion step 16, too |
| | | Insufficient tissue permeabilization (step 2A.v or 2B.iii), which impedes the diffusion of SDS micelles during clearing | Perform a more rigorous permeabilization step after fixing the tissue (PB ST with 1% Triton X-100); always perform a freeze-thaw step as part of the permeabilization regimen |

PACT Clearing as Applied to RNA FISH (Table 4)
Background

The following protocol briefly summarizes the application of PACT-cleared 100 μm thick tissues to RNA fluorescence in-situ hybridization studies (FISH), which was first presented in Yang et al. It should be noted that there are several well-written and detailed articles on FISH and single-molecule (sm) FISH within *Nature Protocols* and *Nature Methods* that discuss the specifics of smFISH (optimized for different model systems, for probe design and for target, for methods of analysis, etc.).

Reagents
1. 100 μm PACT-cleared tissue sections
2. PBS, pH 7.4, RNase-free, 10× (Life Technologies, cat. no. AM9625)
3. Ethanol, absolute (J.T. Baker, cat. no. 8025)
4. Sodium borohydride (Sigma-Aldrich, cat. no. 213462, or Santa Cruz biotechnology, cat. no. CAS 16940-66-2).
5. Sodium borohydride is highly flammable when in contact with moisture and is very toxic to the skin. Do not leave the flask uncapped. Prepare dilutions fresh, on ice, in fume or chemical hood. Close it tightly after weighing, seal with parafilm, and return to its containment canister (if applicable to institutional laboratory practices).
6. Dextran sulfate (Sigma-Aldrich, cat. no. D8906)
7. Formamide, deionized, nuclease-free (EMD Millipore, cat. no. 344206; or Life Technologies, cat. no. AM9342)
8. Saline sodium citrate (SSC), RNase-free, 20× (Life Technologies, cat. no. AM9763)
9. Sodium chloride (Sigma-Aldrich, cat. no. S3014)
10. RNase-free sterile H2O (Life Technologies, cat. no. 10977-015)
11. FISH probes: 20mer oligo probes, 1 nM each per hybridization reaction and labeled with Alexa 594
12. (see main protocol for extended reagents list for PACT-related experiments)

Equipment
1. Microscope: Nikon Ti Eclipse microscope with an Andor Ikon-M camera and an Plan-Apo 60×1.4 N.A. 1 oil objective (w.d 0.13 mm) with an additional 1.5× magnification.
2. Excitation lasers: (589 nm (SDL-589-XXXT), 532 nm (SDL-532-200TG) and 405 nm (SDL-405-LM-030), all manufactured by Shanghai Dream Laser
3. Aminosilane-treated coverslips: Coverslips were sequentially transferred between and sonicated in three solutions: first 1M NaOH, then 100% EtOH, and finally acetone. The cleaned coverslips were immediately submerged into a 2% solution of (3-Aminopropyl) triethoxysilane (Sigma 440140) in acetone for two minutes. Amine-modified coverslips were rinsed and stored in ultrapure water at RT.[189]
4. (see main protocol for extended equipment list for PACT-related experiments)

Reagent Set-Up
1. Ethanol dilutions: Prepare graded dilutions of 100%, 95%, 70% ethanol in RNase-free sterile H2O.
2. Permeabilization Buffer: Prepare a solution of 0.5% sodium borohydride (wt/vol) in 70% ethanol.
3. 2×SSC: For 2×SSC, combine 100 ml 20×SSC with 850 ml RNase-free sterile H2O, pH to 7.0, then add H2O to a total volume of 1 L.
4. 30% Formamide in 2×SSC: For 500 ml, combine 150 ml formamide with 50 ml 20×SSC and 300 ml RNase-free sterile H2O, pH to 7.0.
5. Hybridization buffer: Prepare 10% dextran sulfate (wt/vol, Sigma D8906), 10% formamide (vol/vol) in 2×SSC.

Procedure
Sample Permeabilization Prior to Hybridization
1. Adhere PACT-cleared tissue sections to aminosilane-treated coverslips by dehydrating for 1 hour under light vacuum.
2. Wash samples twice in 100% ethanol for 10 minutes at RT.
3. Wash samples in 95% ethanol for 10 minutes at RT.
4. Incubate samples in 70% ethanol for 2 hours at 4° C.
5. After incubation, place tissue in a 0.5% sodium borohydride (wt/vol) in 70% ethanol solution for 10 minutes at RT.
6. Rehydrate the tissue with 3 washes of 1×PBS.

Sample Hybridization
7. Perform overnight hybridizations at 37° C. in a hybridization buffer containing 1 nM per each of 24 Alexa 594 labeled 20mer oligo probes towards l3-actin.
8. Wash samples in 30% formamide 2×SSC at RT for 30 minutes, followed by 4 washes with 2×SSC.

Sample Imaging
9. Mount the sample between two coverslips with Slowfade Gold+DAPI.
10. Image the sample. For example, 30 μm Z-stacks can be acquired with a 0.5 μm step size.

Image Analysis
11. Analyze the acquired datasets using custom image analysis scripts written in MATLAB.
   (A) Determine the average background of the sample. For example, the images were median filtered using a 50×50 pixel kernel and the average pixel intensity of the center 200×200 pixel sub-image was used as the average background value of the image.
   (B) To detect smFISH dots, apply a Laplacian of Gaussian filter, thresholding the image based on the average background value and comparing the resulting image with a dilated image to find local maxima.
   (C) Calculate the error bars using the standard deviation of the resulting measurements.

TABLE 7

LSFM Parts List

| Part | Vendor | Description | Catalog # |
|---|---|---|---|
| Laser | Changchun New Industries Optoelectronics Technology | Solid state laser 473 nm, 100 mW | MBLIII473 |
| Laser | Thorlabs | HeNe laser 633 nm, 21 mW | HNL210L |
| Mirror | Thorlabs | 1" broadband dielectric mirror, 400-750 nm | BB1-E02 |
| Lens 1 | Thorlabs | 1/2" concave achromatic f = −50 mm doublet | ACN127-050-A |
| Lens 2 | Thorlabs | 1" convex achromatic f = 150 mm doublet | AC254-150-A |
| Beam expander | Thorlabs | 3X beam expander 400-640 nm | BE03M-A |
| Shutter | Uniblitz | Shutter 6 mm diameter | LS6T2 |
| Shutter controller | Uniblitz | Shutter drive unit | VCM-DI |
| Galvanometer scanner | Cambridge Technology | XY galvanometer scanner with 6 mm mirrors | 6215HSM40B |
| F-theta lens | Edmund Optics | Telecentric F-theta lens, 633 nm, 99.1 mm WD | NT64-426 |
| Lens 3 | Thorlabs | 2" convex achromatic doublet f = 100 mm | AC508-100-A |
| Lens 4 | Thorlabs | 1" convex achromatic doublet f = 40 mm | AC254-040-A |
| Sample translation stage | ASI Imaging | MS2000 XYZ-theta motion stage, depth axis with linear encoder | XY 531121010FT, ZLS-50 |
| Objective translation stage | Newport | XYZ ULTRAlign precision stage | 561D-XYZ |
| Motorized translation stage actuator | Newport | 12 mm range DC servo motor | TRB12CC |
| Actuator controller | Newport | DC servo controller | CONEX-CC |
| Objective lens | Olympus | 25 × 1.0 NA multi-immersion | XLSLPLN25XGMP |

TABLE 7-continued

LSFM Parts List

| Part | Vendor | Description | Catalog # |
|---|---|---|---|
| Tube lens | Thorlabs | 2" Achromatic doublet, various focal lengths | e.g. AC508-400-A-ML |
| sCMOS camera | Andor | Light-sheet mode camera | Zyla 4.2 |
| Oscilloscope | Tektronix | Oscilloscope 4-channels, 100 MHz | TDS2014C |
| Function generator | Tektronix | Dual-channel arbitrary function generator | AFG3022B |
| 3D printer | Makerbot | Dual extrusion | Replicator 2X |

The examples and description above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for clearing and expanding tissue, the method comprising the steps of:
   (1) applying a fixing solution to the tissue, thereby forming fixed-tissue;
   (2) applying a surfactant to the fixed-tissue, thereby forming permeabilized-tissue;
   (3) incubating the permeabilized-tissue in a solution comprising acrylate-acrylamide copolymer (AcAm) and one or more polymerizing agent;

(4) incubating the tissue in a solution comprising sodium dodecyl sulfate (SDS), thereby forming SDS-treated cleared tissue;

(5) incubating the SDS-treated cleared tissue in a solution comprising 1-10 mg/mL collagenase or amounts between and for 1-48 hours, thereby forming collagenase-treated tissue; and (6) incubating the collagenase-treated tissue in water, thereby forming cleared and expanded tissue.

2. The method of claim 1, wherein the fixing solution is comprised of 1-15% paraformaldehyde (PFA) and/or 0.1-5% glutaraldehyde.

3. The method of claim 1, further comprising applying a quenching solution to the fixed tissue.

4. The method of claim 3, wherein the quenching solution comprises glycine.

5. The method of claim 1, wherein the surfactant comprises Triton X-100.

6. The method of claim 1, wherein the solution comprising surfactant further comprises phosphate buffered saline (PBS).

7. The method of claim 1, wherein the solution comprising AcAm comprises 0-4% acrylamide, 4-10% sodium acrylate, and 0-1% bis-acrylamide.

8. The method of claim 1, wherein the solution comprising SDS comprises SDS at a concentration of 4-10%.

9. The method of claim 1, wherein the pH of the solution comprising SDS is 6.5-9.5.

10. The method of claim 1, wherein the tissue comprises animal tissue.

11. The method of claim 10, wherein the tissue comprises mammalian tissue.

12. The method of claim 11, wherein the tissue comprises brain tissue.

13. The method of claim 1, wherein the tissue is immunolabeled and/or fluorescently labeled.

14. The method of claim 1, further comprising incubating the tissue in a refractive index matching solution (RIMS).

15. A method for visualizing and/or imaging a cleared and expanded tissue, comprising utilizing a microscope to visualize and/or image a tissue treated according to claim 1.

16. The method of claim 15, wherein the tissue comprises fluorescently labeled cells.

17. The method of claim 15, wherein the refractive index of the tissue has been homogenized.

18. The method of claim 16, further comprising counting the fluorescently labeled cells.

19. The method of claim 18, wherein the fluorescently labeled cells are automatically counted.

20. The method of claim 15, wherein one or more nucleic acids within the tissue are labeled with a marker that can be visualized and/or imaged with a microscope.

21. The method of claim 20, wherein one or more of the nucleic acids is mRNA.

22. The method of claim 21, wherein the one or more nucleic acids are labeled using single molecule fluorescence in-situ hybridization (smFISH).

23. The method of claim 22, further comprising quantifying one or more species of mRNA in the tissue based on a unique fluorescent signature.

24. The method of claim 1, wherein incubating the SDS-treated cleared tissue in a solution comprises a solution with greater than 2 mg/mL collagenase for more than 2 hours.

25. The method of claim 1, wherein incubating the SDS-treated cleared tissue in a solution comprising about 10 mg/mL collagenase comprises incubation for at least 12-24 hours.

26. The method of claim 25, wherein incubating the SDS-treated cleared tissue in a solution comprises incubation at less than 40° C.

* * * * *

UNITED STATES PATENT AND TRADEMARK OFFICE
CERTIFICATE OF CORRECTION

PATENT NO. : 10,794,802 B2
APPLICATION NO. : 15/239724
DATED : October 6, 2020
INVENTOR(S) : Viviana Gradinaru et al.

Page 1 of 1

It is certified that error appears in the above-identified patent and that said Letters Patent is hereby corrected as shown below:

In the Specification

In Column 1, Lines 24-27, under GOVERNMENT RIGHTS, cancel the text:
"This invention was made with government support under Grant Nos. OD017782-01 and AG047664-01 awarded by the National Institutes of Health. The government has certain rights in the invention"

And insert the following:
--This invention was made with government support under Grant Nos. OD017782 and AG047663 awarded by the National Institutes of Health. The government has certain rights in the invention--

Signed and Sealed this
Tenth Day of November, 2020

Andrei Iancu
*Director of the United States Patent and Trademark Office*